US008481678B2

(12) United States Patent
Anton et al.

(10) Patent No.: US 8,481,678 B2
(45) Date of Patent: Jul. 9, 2013

(54) PEPTIDE-BASED TOOTH WHITENING REAGENTS

(75) Inventors: Douglas Robert Anton, Wilmington, DE (US); Scott D. Cunningham, Chadds Ford, PA (US); Stephen R. Fahnestock, Wilmington, DE (US); Kari A. Fosser, Wilmington, DE (US); Hong Wang, Kennet Square, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 653 days.

(21) Appl. No.: 12/698,172

(22) Filed: Feb. 2, 2010

(65) Prior Publication Data

US 2010/0247457 A1    Sep. 30, 2010

Related U.S. Application Data

(60) Provisional application No. 61/164,476, filed on Mar. 30, 2009.

(51) Int. Cl.
| A61K 8/37 | (2006.01) |
| A61Q 11/00 | (2006.01) |
| C07K 14/00 | (2006.01) |
| C07K 9/00 | (2006.01) |
| C07K 7/08 | (2006.01) |
| C07K 7/06 | (2006.01) |
| C08B 1/00 | (2006.01) |
| C08H 1/00 | (2006.01) |

(52) U.S. Cl.
USPC ............ 530/322; 424/55; 530/325; 530/326; 530/327; 530/328; 530/329; 536/56; 526/238.1

(58) Field of Classification Search
None
See application file for complete search history.

(56) References Cited

U.S. PATENT DOCUMENTS

| 3,961,975 | A | 6/1976 | Zannucci et al. |
| 4,494,994 | A | 1/1985 | Cioca et al. |
| 5,085,698 | A | 2/1992 | Ma et al. |
| 5,124,438 | A | 6/1992 | Brueckmann et al. |
| 5,231,131 | A | 7/1993 | Chu et al. |
| 5,451,390 | A | 9/1995 | Hartmann et al. |
| 5,519,085 | A | 5/1996 | Ma et al. |
| 5,672,330 | A | 9/1997 | Hartmann et al. |
| 5,762,914 | A | 6/1998 | Hartmann et al. |
| 6,264,925 | B1 | 7/2001 | Fuglsang et al. |
| 6,706,256 | B2 | 3/2004 | Lawlor |
| 6,740,311 | B2 | 5/2004 | White et al. |
| 7,220,405 | B2 | 5/2007 | Huang et al. |
| 7,285,264 | B2 | 10/2007 | O'Brien et al. |
| 7,309,482 | B2 | 12/2007 | Buse-Williams et al. |
| 2002/0098524 | A1 | 7/2002 | Murray et al. |
| 2003/0152976 | A1 | 8/2003 | Janssen et al. |
| 2003/0185870 | A1 | 10/2003 | Grinstaff et al. |
| 2004/0232377 | A1 | 11/2004 | Nigam |
| 2005/0054752 | A1 | 3/2005 | O'Brien et al. |
| 2005/0069501 | A1 | 3/2005 | Ibrahim et al. |
| 2005/0226839 | A1 | 10/2005 | Huang et al. |
| 2006/0073111 | A1 | 4/2006 | O'Brien et al. |
| 2006/0199206 | A1 | 9/2006 | Wang et al. |
| 2006/0222609 | A1 | 10/2006 | O'Brien et al. |
| 2007/0065387 | A1* | 3/2007 | Beck et al. .................. 424/70.13 |
| 2007/0110686 | A1 | 5/2007 | Lowe et al. |
| 2007/0141628 | A1 | 6/2007 | Cunningham et al. |
| 2007/0141629 | A1 | 6/2007 | Cunningham et al. |
| 2007/0196305 | A1 | 8/2007 | Wang et al. |
| 2007/0261775 | A1 | 11/2007 | Cunningham et al. |
| 2007/0264720 | A1 | 11/2007 | Cunningham et al. |
| 2007/0265431 | A1 | 11/2007 | Cunningham et al. |
| 2008/0107614 | A1 | 5/2008 | Fahnestock et al. |
| 2008/0152600 | A1 | 6/2008 | Huang et al. |
| 2008/0175798 | A1 | 7/2008 | Beck et al. |
| 2008/0207872 | A1 | 8/2008 | Cunningham et al. |
| 2008/0280810 | A1* | 11/2008 | O'Brien et al. .................... 514/2 |
| 2009/0043075 | A1 | 2/2009 | Alsop et al. |
| 2009/0070944 | A1 | 3/2009 | Benson et al. |

FOREIGN PATENT DOCUMENTS

| EP | 0244118 A1 * | 11/1987 |
| JP | 02616786 B2 | 6/1997 |
| WO | 0107009 A1 | 2/2001 |
| WO | 2004048399 A2 | 6/2004 |
| WO | WO 2006028503 A1 * | 3/2006 |
| WO | 2006068011 A1 | 6/2006 |

OTHER PUBLICATIONS

Binz, H. Kaspar et al. (2005) Nature Biotechnology 23, 1257-1268.
Adey, Nils B. (1995) Gene 156, 27-31.
U.S. Appl. No. 61/164,476, filed Mar. 30, 2009 to Fahnestock et al.
International Search Report and Written Opinion for International Application No. PCT/US2010/022804.

* cited by examiner

Primary Examiner — Robert A Wax
Assistant Examiner — William Craigo

(57) ABSTRACT

Peptide-based reagents comprising at least one tooth surface-binding peptide for delivery of at least one polymer-coated white colorant to the surface of teeth are provided. The peptide-based reagent may comprise at least one tooth-binding peptide coupled to, either directly or through one or more spacers, a polymer-binding peptide capable of binding to the polymeric coating on a polymer-coated white colorant. Methods of delivering a polymer-coated white colorant to a tooth surface are also provided as well as oral care compositions comprising the present peptide-based reagents. The peptide-based reagents may be used in conjunction with at least one polymer-coated white colorant to improve the cosmetic appearance of teeth.

9 Claims, No Drawings

SEQUENCE LISTING

<160> NUMBER OF SEQ ID NOS: 191

<210> SEQ ID NO 1
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 1

Ile Pro Trp Trp Asn Ile Arg Ala Pro Leu Asn Ala
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 2

Thr Ala Val Met Asn Val Val Asn Asn Gln Leu Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 3

Val Pro Trp Trp Ala Pro Ser Lys Leu Ser Met Gln
1               5                   10

```
<210> SEQ ID NO 4
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 4

Met Val Met Ala Pro His Thr Pro Arg Ala Arg Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 5

Thr Tyr Pro Asn Trp Ala His Leu Leu Ser His Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Polymethymethacrylate-binding Peptide

<400> SEQUENCE: 6

Thr Pro Trp Trp Arg Ile Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Polymethylmethacrylate-Binding Peptide

<400> SEQUENCE: 7

Asp Leu Thr Leu Pro Phe His
1               5

<210> SEQ ID NO 8
<211> LENGTH: 7
<212> TYPE: PRT
<213> ORGANISM: Artificial Sequence
<220> FEATURE:
<223> OTHER INFORMATION: Polymethylmethacrylate-Binding Peptide

<400> SEQUENCE: 8

Gly Thr Ser Ile Pro Ala Met
1               5

<210> SEQ ID NO 9
<211> LENGTH: 7
<212> TYPE: PRT
<213> ORGANISM: Artificial Sequence
<220> FEATURE:
<223> OTHER INFORMATION: Polymethylmethacrylate-Binding Peptide

<400> SEQUENCE: 9

His His Lys His Val Val Ala
1               5

<210> SEQ ID NO 10
<211> LENGTH: 7
```

```
<212> TYPE: PRT
<213> ORGANISM: Artificial Sequence
<220> FEATURE:
<223> OTHER INFORMATION: Polymethylmethacrylate-Binding Peptide

<400> SEQUENCE: 10

His His His Lys His Phe Met
1               5

<210> SEQ ID NO 11
<211> LENGTH: 7
<212> TYPE: PRT
<213> ORGANISM: Artificial Sequence
<220> FEATURE:
<223> OTHER INFORMATION: Polymethylmethacrylate-Binding Peptide

<400> SEQUENCE: 11

His His His Arg His Gln Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Polymethylmethacrylate-Binding Peptide

<400> SEQUENCE: 12

His His Trp His Ala Pro Arg
1               5

<210> SEQ ID NO 13
<211> LENGTH: 12
<212> TYPE: PRT
<213> ORGANISM: Artificial Sequence
<220> FEATURE:
<223> OTHER INFORMATION: Shampoo-resistant, PMMA-binding peptide

<400> SEQUENCE: 13

Ala Pro Trp His Leu Ser Ser Gln Tyr Ser Gly Thr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Shampoo-resistant PMMA-binding peptide

<400> SEQUENCE: 14

Gly Tyr Cys Leu Arg Val Asp Glu Pro Thr Val Cys Ser Gly
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 15

His Ile His Pro Ser Asp Asn Phe Pro His Lys Asn Arg Thr His
1               5                   10                  15

<210> SEQ ID NO 16
<211> LENGTH: 20
<212> TYPE: PRT
<213> ORGANISM: Artificial Sequence
```

```
<220> FEATURE:
<223> OTHER INFORMATION: Shampoo-resistant PMMA-binding peptide

<400> SEQUENCE: 16

His Thr His His Asp Thr His Lys Pro Trp Pro Thr Asp Asp His Arg
1               5                   10                  15

Asn Ser Ser Val
            20

<210> SEQ ID NO 17
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 17

Pro Glu Asp Arg Pro Ser Arg Thr Asn Ala Leu His His Asn Ala His
1               5                   10                  15

His His Asn Ala
            20

<210> SEQ ID NO 18
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 18

Thr Pro His Asn His Ala Thr Thr Asn His His Ala Gly Lys Lys
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 19

Glu Met Val Lys Asp Ser Asn Gln Arg Asn Thr Arg Ile Ser Ser
1               5                   10                  15

<210> SEQ ID NO 20
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 20

His Tyr Ser Arg Tyr Asn Pro Gly Pro His Pro Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 21

Ile Asp Thr Phe Tyr Met Ser Thr Met Ser His Ser
1               5                   10
```

```
<210> SEQ ID NO 22
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 22

Pro Met Lys Glu Ala Thr His Pro Val Pro Pro His Lys His Ser Glu
1               5                   10                  15

Thr Pro Thr Ala
            20

<210> SEQ ID NO 23
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 23

Tyr Gln Thr Ser Ser Pro Ala Lys Gln Ser Val Gly
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 24

His Leu Pro Ser Tyr Gln Ile Thr Gln Thr His Ala Gln Tyr Arg
1               5                   10                  15

<210> SEQ ID NO 25
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 25

Thr Thr Pro Lys Thr Thr Tyr His Gln Ser Arg Ala Pro Val Thr Ala
1               5                   10                  15

Met Ser Glu Val
            20

<210> SEQ ID NO 26
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 26

Asp Arg Ile His His Lys Ser His His Val Thr Thr Asn His Phe
1               5                   10                  15

<210> SEQ ID NO 27
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 27
```

-continued

Trp Ala Pro Glu Lys Asp Tyr Met Gln Leu Met Lys
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Polypropylene-Binding Peptide

<400> SEQUENCE: 28

Thr Ser Asp Ile Lys Ser Arg Ser Pro His His Arg
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Polypropylene-Binding Peptide

<400> SEQUENCE: 29

His Thr Gln Asn Met Arg Met Tyr Glu Pro Trp Phe
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Polypropylene-Binding Peptide

<400> SEQUENCE: 30

Leu Pro Pro Gly Ser Leu Ala
1               5

<210> SEQ ID NO 31
<211> LENGTH: 12
<212> TYPE: PRT
<213> ORGANISM: Artificial Sequence
<220> FEATURE:
<223> OTHER INFORMATION: Polypropylene-Binding Peptide

<400> SEQUENCE: 31

Met Pro Ala Val Met Ser Ser Ala Gln Val Pro Arg
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Polypropylene-Binding Peptide

<400> SEQUENCE: 32

Asn Gln Ser Phe Leu Pro Leu Asp Phe Pro Phe Arg
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Polypropylene-Binding Peptide

<400> SEQUENCE: 33

Ser Ile Leu Ser Thr Met Ser Pro His Gly Ala Thr
1               5                   10

```
<210> SEQ ID NO 34
<211> LENGTH: 12
<212> TYPE: PRT
<213> ORGANISM: Artificial Sequence
<220> FEATURE:
<223> OTHER INFORMATION: Polypropylene-Binding Peptide

<400> SEQUENCE: 34

Ser Met Lys Tyr Ser His Ser Thr Ala Pro Ala Leu
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Polytertrafluoroethylene-Binding Peptide

<400> SEQUENCE: 35

Glu Ser Ser Tyr Ser Trp Ser Pro Ala Arg Leu Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Polytertrafluoroethylene-Binding Peptide

<400> SEQUENCE: 36

Gly Pro Leu Lys Leu Leu His Ala Trp Trp Gln Pro
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Polytertrafluoroethylene-Binding Peptide

<400> SEQUENCE: 37

Asn Ala Leu Thr Arg Pro Val
1               5

<210> SEQ ID NO 38
<211> LENGTH: 7
<212> TYPE: PRT
<213> ORGANISM: Artificial Sequence
<220> FEATURE:
<223> OTHER INFORMATION: Polytertrafluoroethylene-Binding Peptide

<400> SEQUENCE: 38

Ser Ala Pro Ser Ser Lys Asn
1               5

<210> SEQ ID NO 39
<211> LENGTH: 12
<212> TYPE: PRT
<213> ORGANISM: Artificial Sequence
<220> FEATURE:
<223> OTHER INFORMATION: Polytertrafluoroethylene-Binding Peptide

<400> SEQUENCE: 39

Ser Val Ser Val Gly Met Lys Pro Ser Pro Arg Pro
1               5                   10
```

```
<210> SEQ ID NO 40
<211> LENGTH: 12
<212> TYPE: PRT
<213> ORGANISM: Artificial Sequence
<220> FEATURE:
<223> OTHER INFORMATION: Polytertrafluoroethylene-Binding Peptide

<400> SEQUENCE: 40

Ser Tyr Tyr Ser Leu Pro Pro Ile Phe His Ile Pro
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Polytertrafluoroethylene-Binding Peptide

<400> SEQUENCE: 41

Thr Phe Thr Pro Tyr Ser Ile Thr His Ala Leu Leu
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Polytertrafluoroethylene-Binding Peptide

<400> SEQUENCE: 42

Thr Met Gly Phe Thr Ala Pro Arg Phe Pro His Tyr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Polytertrafluoroethylene-Binding Peptide

<400> SEQUENCE: 43

Thr Asn Pro Phe Pro Pro Pro Pro Ser Ser Pro Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 44

Lys Thr Pro Pro Thr Arg Pro
1               5

<210> SEQ ID NO 45
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 45

Val Ile Asn Pro Asn Leu Asp
1               5

<210> SEQ ID NO 46
<211> LENGTH: 7
```

```
<212> TYPE: PRT
<213> ORGANISM: Artificial Sequence
<220> FEATURE:
<223> OTHER INFORMATION: Nylon-Binding Peptide

<400> SEQUENCE: 46

Lys Val Trp Ile Val Ser Thr
1               5

<210> SEQ ID NO 47
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 47

Ala Glu Pro Val Ala Met Leu
1               5

<210> SEQ ID NO 48
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 48

Ala Glu Leu Val Ala Met Leu
1               5

<210> SEQ ID NO 49
<211> LENGTH: 7
<212> TYPE: PRT
<213> ORGANISM: Artificial Sequence
<220> FEATURE:
<223> OTHER INFORMATION: Nylon-Binding Peptide

<400> SEQUENCE: 49

His Ser Leu Arg Leu Asp Trp
1               5

<210> SEQ ID NO 50
<211> LENGTH: 12
<212> TYPE: PRT
<213> ORGANISM: Artificial Sequence
<220> FEATURE:
<223> OTHER INFORMATION: Polyethylene-Binding Peptide

<400> SEQUENCE: 50

His Asn Lys Ser Ser Pro Leu Thr Ala Ala Leu Pro
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Polyethylene-Binding Peptide

<400> SEQUENCE: 51

Leu Pro Pro Trp Lys His Lys Thr Ser Gly Val Ala
1               5                   10

<210> SEQ ID NO 52
<211> LENGTH: 12
<212> TYPE: PRT
<213> ORGANISM: Artificial Sequence
```

```
<220> FEATURE:
<223> OTHER INFORMATION: Polyethylene-Binding Peptide

<400> SEQUENCE: 52

Leu Pro Trp Trp Leu Arg Asp Ser Tyr Leu Leu Pro
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Polyethylene-Binding Peptide

<400> SEQUENCE: 53

Val Pro Trp Trp Lys His Pro Pro Leu Pro Val Pro
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Polyethylene-Binding Peptide

<400> SEQUENCE: 54

His His Lys Gln Trp His Asn His Pro His His Ala
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Polyethylene-Binding Peptide

<400> SEQUENCE: 55

His Ile Phe Ser Ser Trp His Gln Met Trp His Arg
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Polyethylene-Binding Peptide

<400> SEQUENCE: 56

Trp Pro Ala Trp Lys Thr His Pro Ile Leu Arg Met
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Polystyrene-Binding Peptide

<400> SEQUENCE: 57

Thr Ser Thr Ala Ser Pro Thr Met Gln Ser Lys Ile Arg
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Polystyrene-Binding Peptide
```

<400> SEQUENCE: 58

Lys Arg Asn His Trp Gln Arg Met His Leu Ser Ala
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Polystyrene-Binding Peptide

<400> SEQUENCE: 59

Ser His Ala Thr Pro Pro Gln Gly Leu Gly Pro Gln
1               5                   10

<210> SEQ ID NO 60
<211> LENGTH: 20
<212> TYPE: PRT
<213> ORGANISM: artificial sequence
<220> FEATURE:
<223> OTHER INFORMATION: cellulose acetate-binding peptide

<400> SEQUENCE: 60

Ala Thr Thr Pro Pro Ser Gly Lys Ala Ala His Ser Ala Ala Arg
1               5                   10                  15

Gln Lys Gly Asn
            20

<210> SEQ ID NO 61
<211> LENGTH: 15
<212> TYPE: PRT
<213> ORGANISM: artificial sequence
<220> FEATURE:
<223> OTHER INFORMATION: cellulose acetate-binding peptide

<400> SEQUENCE: 61

Asp Thr Ile His Pro Asn Lys Met Lys Ser Pro Ser Ser Pro Leu
1               5                   10                  15

<210> SEQ ID NO 62
<211> LENGTH: 20
<212> TYPE: PRT
<213> ORGANISM: artificial sequence
<220> FEATURE:
<223> OTHER INFORMATION: cellulose aceteate-binding peptide

<400> SEQUENCE: 62

Asn Gly Asn Asn His Thr Asp Ile Pro Asn Arg Ser Ser Tyr Thr Gly
1               5                   10                  15

Gly Ser Phe Ala
            20

<210> SEQ ID NO 63
<211> LENGTH: 15
<212> TYPE: PRT
<213> ORGANISM: artificial sequence
<220> FEATURE:
<223> OTHER INFORMATION: cellulose acetate-binding peptide

<400> SEQUENCE: 63

Ser Asp Glu Thr Gly Pro Gln Ile Pro His Arg Arg Pro Thr Trp
1               5                   10                  15

<210> SEQ ID NO 64
<211> LENGTH: 21

```
<212> TYPE: PRT
<213> ORGANISM: artificial sequence
<220> FEATURE:
<223> OTHER INFORMATION: cellulose acetate-binding peptide
<220> FEATURE:
<221> NAME/KEY: MISC_FEATURE
<222> LOCATION: (21)..(21)
<223> OTHER INFORMATION: site of biotin attachment

<400> SEQUENCE: 64

Ala Thr Thr Pro Pro Ser Gly Lys Ala Ala His Ser Ala Ala Arg
1               5                   10                  15

Gln Lys Gly Asn Lys
            20

<210> SEQ ID NO 65
<211> LENGTH: 16
<212> TYPE: PRT
<213> ORGANISM: artificial sequence
<220> FEATURE:
<223> OTHER INFORMATION: cellulose acetate-binding peptide
<220> FEATURE:
<221> NAME/KEY: MISC_FEATURE
<222> LOCATION: (16)..(16)
<223> OTHER INFORMATION: site of biotin attachment

<400> SEQUENCE: 65

Asp Thr Ile His Pro Asn Lys Met Lys Ser Pro Ser Ser Pro Leu Lys
1               5                   10                  15

<210> SEQ ID NO 66
<211> LENGTH: 21
<212> TYPE: PRT
<213> ORGANISM: artificial sequence
<220> FEATURE:
<223> OTHER INFORMATION: cellulose acetate-binding peptide
<220> FEATURE:
<221> NAME/KEY: MISC_FEATURE
<222> LOCATION: (21)..(21)
<223> OTHER INFORMATION: site of biotin attachment

<400> SEQUENCE: 66

Asn Gly Asn Asn His Thr Asp Ile Pro Asn Arg Ser Ser Tyr Thr Gly
1               5                   10                  15

Gly Ser Phe Ala Lys
            20

<210> SEQ ID NO 67
<211> LENGTH: 16
<212> TYPE: PRT
<213> ORGANISM: artificial sequence
<220> FEATURE:
<223> OTHER INFORMATION: cellulose acetate-binding peptide
<220> FEATURE:
<221> NAME/KEY: MISC_FEATURE
<222> LOCATION: (16)..(16)
<223> OTHER INFORMATION: site of biotin attachment

<400> SEQUENCE: 67

Ser Asp Glu Thr Gly Pro Gln Ile Pro His Arg Arg Pro Thr Trp Lys
1               5                   10                  15

<210> SEQ ID NO 68
<211> LENGTH: 20
<212> TYPE: DNA
<213> ORGANISM: artificial sequence
<220> FEATURE:
<223> OTHER INFORMATION: Sequencing primer

<400> SEQUENCE: 68
```
ccctcatagt tagcgtaacg 20

<210> SEQ ID NO 69
<211> LENGTH: 20
<212> TYPE: PRT
<213> ORGANISM: artificial sequence
<220> FEATURE:
<223> OTHER INFORMATION: Tooth-binding peptide

<400> SEQUENCE: 69

Ala His Pro Glu Ser Leu Gly Ile Lys Tyr Ala Leu Asp Gly Asn Ser
1               5                   10                  15

Asp Pro His Ala
            20

<210> SEQ ID NO 70
<211> LENGTH: 20
<212> TYPE: PRT
<213> ORGANISM: artificial sequence
<220> FEATURE:
<223> OTHER INFORMATION: Tooth-binding peptide

<400> SEQUENCE: 70

Ala Ser Val Ser Asn Tyr Pro Pro Ile His His Leu Ala Thr Ser Asn
1               5                   10                  15

Thr Thr Val Asn
            20

<210> SEQ ID NO 71
<211> LENGTH: 14
<212> TYPE: PRT
<213> ORGANISM: artificial sequence
<220> FEATURE:
<223> OTHER INFORMATION: Tooth-binding peptide

<400> SEQUENCE: 71

Asp Glu Cys Met Glu Pro Leu Asn Ala Ala His Cys Trp Arg
1               5                   10

<210> SEQ ID NO 72
<211> LENGTH: 14
<212> TYPE: PRT
<213> ORGANISM: artificial sequence
<220> FEATURE:
<223> OTHER INFORMATION: Tooth-binding peptide

<400> SEQUENCE: 72

Asp Glu Cys Met His Gly Ser Asp Val Glu Phe Cys Thr Ser
1               5                   10

<210> SEQ ID NO 73
<211> LENGTH: 14
<212> TYPE: PRT
<213> ORGANISM: artificial sequence
<220> FEATURE:
<223> OTHER INFORMATION: Tooth-binding peptide

<400> SEQUENCE: 73

Asp Leu Cys Ser Met Gln Met Met Asn Thr Gly Cys His Tyr
1               5                   10

<210> SEQ ID NO 74
<211> LENGTH: 14
<212> TYPE: PRT
<213> ORGANISM: artificial sequence
<220> FEATURE:

-continued

<223> OTHER INFORMATION: Tooth-binding peptide

<400> SEQUENCE: 74

Asp Leu Cys Ser Ser Pro Ser Thr Trp Gly Ser Cys Ile Arg
1               5                   10

<210> SEQ ID NO 75
<211> LENGTH: 20
<212> TYPE: PRT
<213> ORGANISM: artificial sequence
<220> FEATURE:
<223> OTHER INFORMATION: Tooth-binding peptide

<400> SEQUENCE: 75

Asp Pro Asn Glu Ser Asn Tyr Glu Asn Ala Thr Thr Val Ser Gln Pro
1               5                   10                  15

Thr Arg His Leu
            20

<210> SEQ ID NO 76
<211> LENGTH: 20
<212> TYPE: PRT
<213> ORGANISM: artificial sequence
<220> FEATURE:
<223> OTHER INFORMATION: Tooth-binding peptide

<400> SEQUENCE: 76

Glu Pro Thr His Pro Thr Met Arg Ala Gln Met His Gln Ser Leu Arg
1               5                   10                  15

Ser Ser Ser Pro
            20

<210> SEQ ID NO 77
<211> LENGTH: 20
<212> TYPE: PRT
<213> ORGANISM: artificial sequence
<220> FEATURE:
<223> OTHER INFORMATION: Tooth-binding peptide

<400> SEQUENCE: 77

Gly Asn Thr Asp Thr Thr Pro Pro Asn Ala Val Met Glu Pro Thr Val
1               5                   10                  15

Gln His Lys Trp
            20

<210> SEQ ID NO 78
<211> LENGTH: 15
<212> TYPE: PRT
<213> ORGANISM: artificial sequence
<220> FEATURE:
<223> OTHER INFORMATION: Tooth-binding peptide

<400> SEQUENCE: 78

Asn Gly Pro Asp Met Val Gln Ser Val Gly Lys His Lys Asn Ser
1               5                   10                  15

<210> SEQ ID NO 79
<211> LENGTH: 15
<212> TYPE: PRT
<213> ORGANISM: artificial sequence
<220> FEATURE:
<223> OTHER INFORMATION: Tooth-binding peptide

<400> SEQUENCE: 79

Asn Gly Pro Glu Val Arg Gln Ile Pro Ala Asn Phe Glu Lys Leu
1               5                   10                  15

```
<210> SEQ ID NO 80
<211> LENGTH: 20
<212> TYPE: PRT
<213> ORGANISM: artificial sequence
<220> FEATURE:
<223> OTHER INFORMATION: Tooth-binding peptide

<400> SEQUENCE: 80

Asn Asn Thr Ser Ala Asp Asn Pro Pro Glu Thr Asp Ser Lys His His
1               5                   10                  15

Leu Ser Met Ser
            20

<210> SEQ ID NO 81
<211> LENGTH: 20
<212> TYPE: PRT
<213> ORGANISM: artificial sequence
<220> FEATURE:
<223> OTHER INFORMATION: Tooth-binding peptide

<400> SEQUENCE: 81

Asn Asn Thr Trp Pro Glu Gly Ala Gly His Thr Met Pro Ser Thr Asn
1               5                   10                  15

Ile Arg Gln Ala
            20

<210> SEQ ID NO 82
<211> LENGTH: 20
<212> TYPE: PRT
<213> ORGANISM: artificial sequence
<220> FEATURE:
<223> OTHER INFORMATION: Tooth-binding peptide

<400> SEQUENCE: 82

Asn Pro Thr Ala Thr Pro His Met Lys Asp Pro Met His Ser Asn Ala
1               5                   10                  15

His Ser Ser Ala
            20

<210> SEQ ID NO 83
<211> LENGTH: 20
<212> TYPE: PRT
<213> ORGANISM: artificial sequence
<220> FEATURE:
<223> OTHER INFORMATION: Tooth-binding peptide

<400> SEQUENCE: 83

Asn Pro Thr Asp His Ile Pro Ala Asn Ser Thr Asn Ser Arg Val Ser
1               5                   10                  15

Lys Gly Asn Thr
            20

<210> SEQ ID NO 84
<211> LENGTH: 15
<212> TYPE: PRT
<213> ORGANISM: artificial sequence
<220> FEATURE:
<223> OTHER INFORMATION: Tooth-binding peptide

<400> SEQUENCE: 84

Asn Pro Thr Asp Ser Thr His Met Met His Ala Arg Asn His Glu
1               5                   10                  15

<210> SEQ ID NO 85
```

```
<211> LENGTH: 14
<212> TYPE: PRT
<213> ORGANISM: artificial sequence
<220> FEATURE:
<223> OTHER INFORMATION: Tooth-binding peptide

<400> SEQUENCE: 85

Gln His Cys Ile Thr Glu Arg Leu His Pro Pro Cys Thr Lys
1               5                   10

<210> SEQ ID NO 86
<211> LENGTH: 14
<212> TYPE: PRT
<213> ORGANISM: artificial sequence
<220> FEATURE:
<223> OTHER INFORMATION: Tooth-binding peptide

<400> SEQUENCE: 86

Thr Pro Cys Ala Pro Ala Ser Phe Asn Pro His Cys Ser Arg
1               5                   10

<210> SEQ ID NO 87
<211> LENGTH: 14
<212> TYPE: PRT
<213> ORGANISM: artificial sequence
<220> FEATURE:
<223> OTHER INFORMATION: Tooth-binding peptide

<400> SEQUENCE: 87

Thr Pro Cys Ala Thr Tyr Pro His Phe Ser Gly Cys Arg Ala
1               5                   10

<210> SEQ ID NO 88
<211> LENGTH: 20
<212> TYPE: PRT
<213> ORGANISM: artificial sequence
<220> FEATURE:
<223> OTHER INFORMATION: Tooth-binding peptide

<400> SEQUENCE: 88

Trp Cys Thr Asp Phe Cys Thr Arg Ser Thr Pro Thr Ser Thr Ser Arg
1               5                   10                  15

Ser Thr Thr Ser
            20

<210> SEQ ID NO 89
<211> LENGTH: 20
<212> TYPE: PRT
<213> ORGANISM: artificial sequence
<220> FEATURE:
<223> OTHER INFORMATION: Tooth-binding peptide

<400> SEQUENCE: 89

Ala Pro Pro Leu Lys Thr Tyr Met Gln Glu Arg Glu Leu Thr Met Ser
1               5                   10                  15

Gln Asn Lys Asp
            20

<210> SEQ ID NO 90
<211> LENGTH: 20
<212> TYPE: PRT
<213> ORGANISM: artificial sequence
<220> FEATURE:
<223> OTHER INFORMATION: Tooth-binding peptide

<400> SEQUENCE: 90

Glu Pro Pro Thr Arg Thr Arg Val Asn Asn His Thr Val Thr Val Gln
```

```
1               5                   10                  15

Ala Gln Gln His
            20

<210> SEQ ID NO 91
<211> LENGTH: 14
<212> TYPE: PRT
<213> ORGANISM: artificial sequence
<220> FEATURE:
<223> OTHER INFORMATION: Tooth-binding peptide

<400> SEQUENCE: 91

Gly Tyr Cys Leu Arg Gly Asp Glu Pro Ala Val Cys Ser Gly
1               5                   10

<210> SEQ ID NO 92
<211> LENGTH: 20
<212> TYPE: PRT
<213> ORGANISM: artificial sequence
<220> FEATURE:
<223> OTHER INFORMATION: Tooth-binding peptide

<400> SEQUENCE: 92

Leu Ser Ser Lys Asp Phe Gly Val Thr Asn Thr Asp Gln Arg Thr Tyr
1               5                   10                  15

Asp Tyr Thr Thr
            20

<210> SEQ ID NO 93
<211> LENGTH: 14
<212> TYPE: PRT
<213> ORGANISM: artificial sequence
<220> FEATURE:
<223> OTHER INFORMATION: Tooth-binding peptide

<400> SEQUENCE: 93

Asn Phe Cys Glu Thr Gln Leu Asp Leu Ser Val Cys Thr Val
1               5                   10

<210> SEQ ID NO 94
<211> LENGTH: 14
<212> TYPE: PRT
<213> ORGANISM: artificial sequence
<220> FEATURE:
<223> OTHER INFORMATION: Tooth-binding peptide

<400> SEQUENCE: 94

Asn Thr Cys Gln Pro Thr Lys Asn Ala Thr Pro Cys Ser Ala
1               5                   10

<210> SEQ ID NO 95
<211> LENGTH: 20
<212> TYPE: PRT
<213> ORGANISM: artificial sequence
<220> FEATURE:
<223> OTHER INFORMATION: Tooth-binding peptide

<400> SEQUENCE: 95

Pro Ser Glu Pro Glu Arg Arg Asp Arg Asn Ile Ala Ala Asn Ala Gly
1               5                   10                  15

Arg Phe Asn Thr
            20

<210> SEQ ID NO 96
<211> LENGTH: 18
<212> TYPE: PRT
```

```
<213> ORGANISM: artificial sequence
<220> FEATURE:
<223> OTHER INFORMATION: Tooth-binding peptide

<400> SEQUENCE: 96

Thr His Asn Met Ser His Phe Pro Pro Ser Gly His Pro Lys Arg Thr
1               5                   10                  15

Ala Thr

<210> SEQ ID NO 97
<211> LENGTH: 14
<212> TYPE: PRT
<213> ORGANISM: artificial sequence
<220> FEATURE:
<223> OTHER INFORMATION: Tooth-binding peptide

<400> SEQUENCE: 97

Thr Thr Cys Pro Thr Met Gly Thr Tyr His Val Cys Trp Leu
1               5                   10

<210> SEQ ID NO 98
<211> LENGTH: 20
<212> TYPE: PRT
<213> ORGANISM: artificial sequence
<220> FEATURE:
<223> OTHER INFORMATION: Tooth-binding peptide

<400> SEQUENCE: 98

Tyr Cys Ala Asp His Thr Pro Asp Pro Ala Asn Pro Asn Lys Ile Cys
1               5                   10                  15

Gly Tyr Ser His
            20

<210> SEQ ID NO 99
<211> LENGTH: 20
<212> TYPE: PRT
<213> ORGANISM: artificial sequence
<220> FEATURE:
<223> OTHER INFORMATION: Tooth-binding peptide

<400> SEQUENCE: 99

Ala Ala Asn Pro His Thr Glu Trp Asp Arg Asp Ala Phe Gln Leu Ala
1               5                   10                  15

Met Pro Pro Lys
            20

<210> SEQ ID NO 100
<211> LENGTH: 20
<212> TYPE: PRT
<213> ORGANISM: artificial sequence
<220> FEATURE:
<223> OTHER INFORMATION: Tooth-binding peptide

<400> SEQUENCE: 100

Asp Leu His Pro Met Asp Pro Ser Asn Lys Arg Pro Asp Asn Pro Ser
1               5                   10                  15

Asp Leu His Thr
            20

<210> SEQ ID NO 101
<211> LENGTH: 14
<212> TYPE: PRT
<213> ORGANISM: artificial sequence
<220> FEATURE:
<223> OTHER INFORMATION: Tooth-binding peptide
```

```
<400> SEQUENCE: 101

Glu Ser Cys Val Ser Asn Ala Leu Met Asn Gln Cys Ile Tyr
1               5                   10

<210> SEQ ID NO 102
<211> LENGTH: 20
<212> TYPE: PRT
<213> ORGANISM: artificial sequence
<220> FEATURE:
<223> OTHER INFORMATION: Tooth-binding peptide

<400> SEQUENCE: 102

His Asn Lys Ala Asp Ser Trp Asp Pro Asp Leu Pro Pro His Ala Gly
1               5                   10                  15

Met Ser Leu Gly
            20

<210> SEQ ID NO 103
<211> LENGTH: 20
<212> TYPE: PRT
<213> ORGANISM: artificial sequence
<220> FEATURE:
<223> OTHER INFORMATION: Tooth-binding peptide

<400> SEQUENCE: 103

Leu Asn Asp Gln Arg Lys Pro Gly Pro Pro Thr Met Pro Thr His Ser
1               5                   10                  15

Pro Ala Val Gly
            20

<210> SEQ ID NO 104
<211> LENGTH: 14
<212> TYPE: PRT
<213> ORGANISM: artificial sequence
<220> FEATURE:
<223> OTHER INFORMATION: Tooth-binding peptide

<400> SEQUENCE: 104

Asn Thr Cys Ala Thr Ser Pro Asn Ser Tyr Thr Cys Ser Asn
1               5                   10

<210> SEQ ID NO 105
<211> LENGTH: 14
<212> TYPE: PRT
<213> ORGANISM: artificial sequence
<220> FEATURE:
<223> OTHER INFORMATION: Tooth-binding peptide

<400> SEQUENCE: 105

Ser Asp Cys Thr Ala Gly Leu Val Pro Pro Leu Cys Ala Thr
1               5                   10

<210> SEQ ID NO 106
<211> LENGTH: 20
<212> TYPE: PRT
<213> ORGANISM: artificial sequence
<220> FEATURE:
<223> OTHER INFORMATION: Tooth-binding peptide

<400> SEQUENCE: 106

Thr Ile Glu Ser Ser Gln His Ser Arg Thr His Gln Gln Asn Tyr Gly
1               5                   10                  15

Ser Thr Lys Thr
            20
```

```
<210> SEQ ID NO 107
<211> LENGTH: 20
<212> TYPE: PRT
<213> ORGANISM: artificial sequence
<220> FEATURE:
<223> OTHER INFORMATION: Tooth-binding peptide

<400> SEQUENCE: 107

Val Gly Thr Met Lys Gln His Pro Thr Thr Thr Gln Pro Pro Arg Val
1               5                   10                  15

Ser Ala Thr Asn
            20

<210> SEQ ID NO 108
<211> LENGTH: 20
<212> TYPE: PRT
<213> ORGANISM: artificial sequence
<220> FEATURE:
<223> OTHER INFORMATION: Tooth-binding peptide

<400> SEQUENCE: 108

Tyr Ser Glu Thr Pro Asn Asp Gln Lys Pro Asn Pro His Tyr Lys Val
1               5                   10                  15

Ser Gly Thr Lys
            20

<210> SEQ ID NO 109
<211> LENGTH: 8
<212> TYPE: PRT
<213> ORGANISM: Artificial Sequence
<220> FEATURE:
<223> OTHER INFORMATION: Caspase 3 cleavage site

<400> SEQUENCE: 109

Leu Glu Ser Gly Asp Glu Val Asp
1               5

<210> SEQ ID NO 110
<211> LENGTH: 37
<212> TYPE: PRT
<213> ORGANISM: Artificial Sequence
<220> FEATURE:
<223> OTHER INFORMATION: Peptide Spacer

<400> SEQUENCE: 110

Thr Ser Thr Ser Lys Ala Ser Thr Thr Thr Ser Ser Lys Thr Thr
1               5                   10                  15

Thr Thr Ser Ser Lys Thr Thr Thr Thr Ser Lys Thr Ser Thr Thr
            20                  25                  30

Ser Ser Ser Ser Thr
        35

<210> SEQ ID NO 111
<211> LENGTH: 22
<212> TYPE: PRT
<213> ORGANISM: Artificial Sequence
<220> FEATURE:
<223> OTHER INFORMATION: Peptide Spacer

<400> SEQUENCE: 111

Gly Gln Gly Gly Tyr Gly Gly Leu Gly Ser Gln Gly Ala Gly Arg Gly
1               5                   10                  15

Gly Leu Gly Gly Gln Gly
            20
```

```
<210> SEQ ID NO 112
<211> LENGTH: 10
<212> TYPE: PRT
<213> ORGANISM: Artificial Sequence
<220> FEATURE:
<223> OTHER INFORMATION: Peptide Spacer

<400> SEQUENCE: 112

Gly Pro Gly Gly Tyr Gly Pro Gly Gln Gln
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Peptide Spacer

<400> SEQUENCE: 113

Gly Gly Gly Cys Gly Gly Gly
1               5

<210> SEQ ID NO 114
<211> LENGTH: 4
<212> TYPE: PRT
<213> ORGANISM: Artificial Sequence
<220> FEATURE:
<223> OTHER INFORMATION: Peptide Spacer

<400> SEQUENCE: 114

Gly Gly Gly Cys
1

<210> SEQ ID NO 115
<211> LENGTH: 5
<212> TYPE: PRT
<213> ORGANISM: Artificial Sequence
<220> FEATURE:
<223> OTHER INFORMATION: Peptide Spacer

<400> SEQUENCE: 115

Gly Gly Pro Lys Lys
1               5

<210> SEQ ID NO 116
<211> LENGTH: 159
<212> TYPE: PRT
<213> ORGANISM: artificial sequence
<220> FEATURE:
<223> OTHER INFORMATION: Synthetic peptide-based tooth whitening reagent

<400> SEQUENCE: 116

Pro His Met Ala Ser Met Thr Gly Gly Gln Gln Met Gly Ser Tyr Ser
1               5                   10                  15

Glu Thr Pro Asn Asp Gln Lys Pro Asn Pro His Tyr Lys Val Ser Gly
                20                  25                  30

Thr Lys Gly Pro Glu Glu Ala Ala Lys Lys Glu Glu Ala Ala Lys Lys
            35                  40                  45

Pro Ala Tyr Ser Glu Thr Pro Asn Asp Gln Lys Pro Asn Pro His Tyr
        50                  55                  60

Lys Val Ser Gly Thr Lys Gly Ser Gly Gly Gly Ser Gly Ser Gly
65                  70                  75                  80

Gly Gly Gly Ser Val Arg Pro Asn Leu His Arg Lys Ala Lys Ala Lys
                85                  90                  95

Pro Asp His Lys Gln Ser Glu Asn Arg Lys Val Pro Phe Tyr Ser His
```

-continued

```
                100              105              110
Gly Ser Ser Gly Gly Gly Val Arg Pro Asn Leu His Arg Lys Ala
            115              120              125
Lys Ala Lys Pro Asp His Lys Gln Ser Glu Asn Arg Lys Val Pro Phe
        130              135              140
Tyr Ser His Gly Ser Ser Gly Gly Gly His His His His His His
145              150              155
```

<210> SEQ ID NO 117
<211> LENGTH: 5214
<212> TYPE: DNA
<213> ORGANISM: artificial sequence
<220> FEATURE:
<223> OTHER INFORMATION: plasmid

<400> SEQUENCE: 117

| | | | | | |
|---|---|---|---|---|---|
| tacctgcctg | acagcatgg | cctgcaacgc | gggcatcccg | atgccgccgg | aagcgagaag | 60 |
| aatcataatg | gggaaggcca | tccagcctcg | cgtcgcgaac | gccagcaaga | cgtagcccag | 120 |
| cgcgtcggcc | gccatgccgg | cgataatggc | ctgcttctcg | ccgaaacgtt | tggtggcggg | 180 |
| accagtgacg | aaggcttgag | cgagggcgtg | caagattccg | aataccgcaa | gcgacaggcc | 240 |
| gatcatcgtc | gcgctccagc | gaaagcggtc | ctcgccgaaa | atgacccaga | gcgctgccgg | 300 |
| cacctgtcct | acgagttgca | tgataaagaa | gacagtcata | agtgcggcga | cgatagtcat | 360 |
| gccccgcgcc | accggaagg | agctgactgg | gttgaaggct | ctcaagggca | tcggtcgatc | 420 |
| gacgctctcc | cttatgcgac | tcctgcatta | ggaagcagcc | cagtagtagg | ttgaggccgt | 480 |
| tgagcaccgc | cgccgcaagg | aatggtgcat | gcaaggagat | ggcgcccaac | agtccccgg | 540 |
| ccacgggcc | tgccaccata | cccacgccga | acaagcgct | catgagcccg | aagtggcgag | 600 |
| cccgatcttc | cccatcggtg | atgtcggcga | tataggcgcc | agcaaccgca | cctgtggcgc | 660 |
| cggtgatgcc | ggccacgatg | cgtccggcgt | agaggatcga | gatctcgatc | ccgcgaaatt | 720 |
| aatacgactc | actatagga | gaccacaacg | gtttccctct | agaaataatt | ttgtttaact | 780 |
| ttaagaagga | gatatacata | tgcacactcc | agaacatatc | accgcagtag | tacagcgttt | 840 |
| tgtggcagct | ctgaacgcgg | gcgagctgga | aggtattgtg | gcgctgttcg | cggaagaagc | 900 |
| caccgtggaa | gaaccggtgg | gttctgaacc | gcgttccggc | accgcagcct | gccgtgaatt | 960 |
| ttacgcaaac | agcctgaagc | tgccgctggc | ggttgaactg | acccaagaat | gtcgtgcggt | 1020 |
| ggctaacgaa | gccgctttcg | cgttcaccgt | gtccttcgaa | taccagggtc | gtaagaccgt | 1080 |
| tgtggcgcca | tgcgaacact | tcgtttcaa | cggcgcaggc | aaagtggttt | ccatccgcgc | 1140 |
| actgttcggt | gaaagaaca | tccatgcttg | tcagggatcc | gaccctggta | tcccgtggtg | 1200 |
| gaacattcgc | gcacctctga | atgctggtgc | tggtattccg | tggtggaaca | tccgtgctcc | 1260 |
| tctgaacgcg | ggtggctccg | gtccgggctc | cggtggcaac | acgagccaac | tgagcaccgg | 1320 |
| tggtggcaac | acttcccagc | tgtccaccgg | cggtccgaaa | agtaataag | gcgcgccgac | 1380 |
| ccagctttct | tgtacaaagt | ggttgattcg | aggctgctaa | caaagcccga | aggaagctg | 1440 |
| agttggctgc | tgccaccgct | gagcaataac | tagcataacc | ccttgggcc | tctaaacggg | 1500 |
| tcttgagggg | ttttttgctg | aaaggaggaa | ctatatccgg | atatccacag | gacgggtgtg | 1560 |
| gtcgccatga | tcgcgtagtc | gatagtggct | ccaagtagcg | aagcgagcag | actgggcgg | 1620 |
| cggccaaagc | ggtcggacag | tgctccgaga | acgggtgcgc | atagaaattg | catcaacgca | 1680 |
| tatagcgcta | gcagcacgcc | atagtgactg | gcgatgctgt | cggaatggac | gatatcccgc | 1740 |
| aagaggcccg | gcagtaccgg | cataaccaag | cctatgccta | cagcatccag | ggtgacggtg | 1800 |

```
ccgaggatga cgatgagcgc attgttagat tcatacacg gtgcctgact gcgttagcaa     1860
tttaactgtg ataaactacc gcattaaagc ttatcgatga taagctgtca acatgagaa     1920
ttcttgaaga cgaaagggcc tcgtgatacg cctattttta taggttaatg tcatgataat    1980
aatggtttct tagacgtcag gtggcacttt tcggggaaat gtgcgcggaa cccctatttg    2040
tttattttc taaatacatt caaatatgta tccgctcatg agacaataac cctgataaat     2100
gcttcaataa tattgaaaaa ggaagagtat gagtattcaa catttccgtg tcgcccttat    2160
tccctttttt gcggcatttt gccttcctgt ttttgctcac ccagaaacgc tggtgaaagt    2220
aaaagatgct gaagatcagt tgggtgcacg agtgggttac atcgaactgg atctcaacag    2280
cggtaagatc cttgagagtt ttcgccccga agaacgtttt ccaatgatga gcacttttaa    2340
agttctgcta tgtggcgcgg tattatcccg tgttgacgcc gggcaagagc aactcggtcg    2400
ccgcatacac tattctcaga atgacttggt tgagtactca ccagtcacag aaaagcatct    2460
tacggatggc atgacagtaa gagaattatg cagtgctgcc ataaccatga gtgataacac    2520
tgcggccaac ttacttctga caacgatcgg aggaccgaag gagctaaccg cttttttgca    2580
caacatgggg gatcatgtaa ctcgccttga tcgttgggaa ccggagctga atgaagccat    2640
accaaacgac gagcgtgaca ccacgatgcc tgcagcaatg gcaacaacgt tgcgcaaact    2700
attaactggc gaactactta ctctagcttc ccggcaacaa ttaatagact ggatggaggc    2760
ggataaagtt gcaggaccac ttctgcgctc ggcccttccg gctggctggt ttattgctga    2820
taaatctgga gccggtgagc gtgggtctcg cggtatcatt gcagcactgg ggccagatgg    2880
taagccctcc cgtatcgtag ttatctacac gacggggagt caggcaacta tggatgaacg    2940
aaatagacag atcgctgaga taggtgcctc actgattaag cattggtaac tgtcagacca    3000
agtttactca tatatacttt agattgattt aaaacttcat ttttaattta aaaggatcta    3060
ggtgaagatc ctttttgata atctcatgac caaaatccct taacgtgagt tttcgttcca    3120
ctgagcgtca gaccccgtag aaaagatcaa aggatcttct tgagatcctt ttttctgcg    3180
cgtaatctgc tgcttgcaaa caaaaaaacc accgctacca gcggtggttt gtttgccgga    3240
tcaagagcta ccaactcttt ttccgaaggt aactggcttc agcagagcgc agataccaaa    3300
tactgtcctt ctagtgtagc cgtagttagg ccaccacttc aagaactctg tagcaccgcc    3360
tacatacctc gctctgctaa tcctgttacc agtggctgct gccagtggcg ataagtcgtg    3420
tcttaccggg ttggactcaa gacgatagtt accggataag gcgcagcggt cgggctgaac    3480
ggggggttcg tgcacacagc ccagcttgga gcgaacgacc tacaccgaac tgagatacct    3540
acagcgtgag ctatgagaaa gcgccacgct tcccgaaggg agaaaggcgg acaggtatcc    3600
ggtaagcggc agggtcggaa caggagagcg cacgagggag cttccagggg gaaacgcctg    3660
gtatctttat agtcctgtcg ggtttcgcca cctctgactt gagcgtcgat ttttgtgatg    3720
ctcgtcaggg gggcggagcc tatggaaaaa cgccagcaac gcggcctttt tacggttcct    3780
ggccttttgc tggccttttg ctcacatgtt ctttcctgcg ttatcccctg attctgtgga    3840
taaccgtatt accgcctttg agtgagctga taccgctcgc cgcagccgaa cgaccgagcg    3900
cagcgagtca gtgagcgagg aagcggaaga gcgcctgatg cggtattttc tccttacgca    3960
tctgtgcggt atttcacacc gcatatatgg tgcactctca gtacaatctg ctctgatgcc    4020
gcatagttaa gccagtatac actccgctat cgctacgtga ctgggtcatg gctgcgcccc    4080
gacacccgcc aacacccgct gacgcgccct gacgggcttg tctgctcccg gcatccgctt    4140
acagacaagc tgtgaccgtc tccgggagct gcatgtgtca gaggttttca ccgtcatcac    4200
```

```
cgaaacgcgc gaggcagctg cggtaaagct catcagcgtg gtcgtgaagc gattcacaga   4260
tgtctgcctg ttcatccgcg tccagctcgt tgagtttctc cagaagcgtt aatgtctggc   4320
ttctgataaa gcgggccatg ttaagggcgg tttttcctg tttggtcact gatgcctccg    4380
tgtaaggggg atttctgttc atgggggtaa tgataccgat gaaacgagag aggatgctca   4440
cgatacgggt tactgatgat gaacatgccc ggttactgga acgttgtgag ggtaaacaac   4500
tggcggtatg gatgcggcgg gaccagagaa aaatcactca gggtcaatgc cagcgcttcg   4560
ttaatacaga tgtaggtgtt ccacagggta gccagcagca tcctgcgatg cagatccgga   4620
acataatggt gcagggcgct gacttccgcg tttccagact ttacgaaaca cggaaaccga   4680
agaccattca tgttgttgct caggtcgcag acgttttgca gcagcagtcg cttcacgttc   4740
gctcgcgtat cggtgattca ttctgctaac cagtaaggca accccgccag cctagccggg   4800
tcctcaacga caggagcacg atcatgcgca cccgtggcca ggaccaacg ctgcccgaga    4860 tgcgccgcgt gcggctgctg gagatggcgg acgcgatgga tatgttctgc caagggttgg   4920
tttgcgcatt cacagttctc cgcaagaatt gattggctcc aattcttgga gtggtgaatc   4980
cgttagcgag gtgccgccgg cttccattca ggtcgaggtg gcccggctcc atgcaccgcg   5040
acgcaacgcg gggaggcaga caaggtatag ggcggcgcct acaatccatg ccaacccgtt   5100
ccatgtgctc gccgaggcgg cataaatcgc cgtgacgatc agcggtccag tgatcgaagt   5160
taggctggta agagccgcga gcgatccttg aagctgtccc tgatggtcgt catc         5214
```

<210> SEQ ID NO 118
<211> LENGTH: 32
<212> TYPE: PRT
<213> ORGANISM: artificial sequence
<220> FEATURE:
<223> OTHER INFORMATION: cellulose acetate-binding peptide

<400> SEQUENCE: 118

Val Arg Pro Asn Leu His Arg Lys Ala Lys Ala Lys Pro Asp His Lys
1               5                   10                  15

Gln Ser Glu Asn Arg Lys Val Pro Phe Tyr Ser His Gly Ser Ser Gly
            20                  25                  30

<210> SEQ ID NO 119
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 119

Asn Gly Asn Asn His Thr Asp Ile Pro Asn Arg Ser Ser Tyr Thr Gly
1               5                   10                  15

Gly Ser Phe Ala
            20

<210> SEQ ID NO 120
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 120

Thr Met Thr Asn His Val Tyr Asn Ser Tyr Thr Glu Lys His Ser Ser
1               5                   10                  15

Thr His Arg Ser
         20

<210> SEQ ID NO 121
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 121

Thr Thr Tyr His Tyr Lys Asn Ile Tyr Gln Glu Ser Tyr Gln Gln Arg
1               5                   10                  15

Asn Pro Ala Val
         20

<210> SEQ ID NO 122
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 122

Val Glu Pro Ala Thr Lys Asn Met Arg Glu Ala Arg Ser Ser Thr Gln
1               5                   10                  15

Met Arg Arg Ile
         20

<210> SEQ ID NO 123
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 123

Tyr Leu Leu Pro Lys Asp Gln Thr Thr Ala Pro Gln Val Thr Pro Ile
1               5                   10                  15

Val Gln His Lys
         20

<210> SEQ ID NO 124
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 124

Ala Ser Asn Leu Asp Ser Thr Phe Thr Ala Ile Asn Thr Pro Ala Cys
1               5                   10                  15

Cys Thr

<210> SEQ ID NO 125
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 125

Glu Phe Pro Tyr Tyr Asn Asp Asn Pro Pro Asn Pro Glu Arg His Thr
1               5                   10                  15

Leu Arg

<210> SEQ ID NO 126
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 126

Gly Met Pro Thr Arg Tyr Tyr His Asn Thr Pro Pro His Leu Thr Pro
1               5                   10                  15

Lys Phe

<210> SEQ ID NO 127
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 127

His Lys Asn Ala Ile Gln Pro Val Asn Asp Ala Thr Thr Leu Asp Thr
1               5                   10                  15

Thr Met

<210> SEQ ID NO 128
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 128

Ala Val Val Pro Ala Asp Leu Asn Asp His Ala Asn His Leu Ser
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 129

Asp Leu Gly Thr Phe Pro Asn Arg Thr Leu Lys Met Ala Ala His
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 130

Phe Asp Gly Ile Gly Leu Gly Thr Ala Thr Arg His Gln Asn Arg
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 131

```
Gln Ala Ala Gln Val His Met Met Gln His Ser Arg Pro Thr Thr
1               5                   10                  15
```

<210> SEQ ID NO 132
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 132

```
Ser Glu Ala Arg Ala Arg Thr Phe Asn Asp His Thr Thr Pro Met Pro
1               5                   10                  15

Ile Ile
```

<210> SEQ ID NO 133
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 133

```
Glu Leu Asp His Asp Ser Arg His Tyr Met Asn Gly Leu Gln Arg Lys
1               5                   10                  15

Val Thr
```

<210> SEQ ID NO 134
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 134

```
Gly Pro Gln His Val Leu Met Gln Asp Thr His Gln Gly Tyr Ala Phe
1               5                   10                  15

Asp Asn
```

<210> SEQ ID NO 135
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 135

```
Thr Thr Gly Ser Ser Ser Gln Ala Asp Thr Ser Ala Ser Met Ser Ile
1               5                   10                  15

Val Pro Ala His
            20
```

<210> SEQ ID NO 136
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 136

```
Lys Ala Pro Ile Ala Asn Met Leu Gln Pro His Ser Tyr Gln Tyr Ser
1               5                   10                  15

Val Ala
```

```
<210> SEQ ID NO 137
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 137

Thr Tyr Gln Gly Val Pro Ser Trp Pro Ala Val Ile Asp Asp Ala Ile
1               5                   10                  15

Arg Arg

<210> SEQ ID NO 138
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 138

Val Asn Pro Asn Trp Val Glu Thr Gln Ala Leu His Gln Pro Pro Gly
1               5                   10                  15

Asn Thr

<210> SEQ ID NO 139
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 139

Asp His Asn Asn Arg Gln His Ala Val Glu Val Arg Glu Asn Lys Thr
1               5                   10                  15

His Thr Ala Arg
            20

<210> SEQ ID NO 140
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 140

Ile Tyr Pro Asn Glu Ser Met Ser Thr Ser Asn Val Arg Gly Pro Tyr
1               5                   10                  15

His Pro

<210> SEQ ID NO 141
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 141

His Asp Pro Asn His Leu Thr His Gln Ala Arg Thr Ile Tyr Arg Asn
1               5                   10                  15

Ala Asn His Thr
            20

<210> SEQ ID NO 142
<211> LENGTH: 15
<212> TYPE: PRT
```

```
<213> ORGANISM: Artificial Sequence
<220> FEATURE:
<223> OTHER INFORMATION: Synthetic oral-surface binding peptide

<400> SEQUENCE: 142

Ser Asn Ala Thr Met Tyr Asn Ile Gln Ser His Ser His His Gln
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 143

Ala Asn Glu Leu Ser Thr Tyr Ala Gln Thr Asn Pro Gly Ser Gly
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 144

Asp Thr Ile His Pro Asn Lys Met Lys Ser Pro Ser Ser Pro Leu
1               5                   10                  15

<210> SEQ ID NO 145
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 145

Ala Pro Pro Thr Tyr Gln Thr Ala Ser Tyr Pro His Asn Leu Pro Ser
1               5                   10                  15

Lys Arg Lys Met
            20

<210> SEQ ID NO 146
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 146

Gln Val Pro Asp Tyr Leu Ser Pro Thr His Gln Lys Lys Ala Phe Leu
1               5                   10                  15

Glu Ile Pro Thr
            20

<210> SEQ ID NO 147
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 147

Thr Asn Asp Leu His Ala Asn Pro Phe Thr Gly Thr Tyr Ile Ala Pro
1               5                   10                  15
```

```
Asp Pro Thr Ser
        20

<210> SEQ ID NO 148
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 148

His Lys Asn Glu Asn Ile Met Gln Tyr Asn Val Asn Asp Arg Trp His
1               5                   10                  15

Ile Thr Pro Ala
        20

<210> SEQ ID NO 149
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 149

Ile Asp Gly Pro His His Ser Pro Val His Arg Tyr His Thr Pro Ser
1               5                   10                  15

Ile Thr

<210> SEQ ID NO 150
<211> LENGTH: 15
<212> TYPE: PRT
<213> ORGANISM: Artificial Sequence
<220> FEATURE:
<223> OTHER INFORMATION: Synthetic peptide

<400> SEQUENCE: 150

Ile Pro Trp Trp Asn Ile Arg Ala Pro Leu Asn Ala Gly Gly Gly
1               5                   10                  15

<210> SEQ ID NO 151
<211> LENGTH: 4
<212> TYPE: PRT
<213> ORGANISM: artificial sequence
<220> FEATURE:
<223> OTHER INFORMATION: synthetic construct

<400> SEQUENCE: 151

Ser Ser Arg Pro
1

<210> SEQ ID NO 152
<211> LENGTH: 25
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (25)..(25)
<223> OTHER INFORMATION: Site for Biotin attachment

<400> SEQUENCE: 152

Ser Ser Arg Pro Asn Gly Asn Asn His Thr Asp Ile Pro Asn Arg Ser
1               5                   10                  15

Ser Tyr Thr Gly Gly Ser Phe Ala Lys
        20                  25
```

```
<210> SEQ ID NO 153
<211> LENGTH: 25
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (25)..(25)
<223> OTHER INFORMATION: Site for Biotin attachment

<400> SEQUENCE: 153

Ser Ser Arg Pro Thr Met Thr Asn His Val Tyr Asn Ser Tyr Thr Glu
1               5                   10                  15

Lys His Ser Ser Thr His Arg Ser Lys
            20                  25

<210> SEQ ID NO 154
<211> LENGTH: 25
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (25)..(25)
<223> OTHER INFORMATION: Site for Biotin attachment

<400> SEQUENCE: 154

Ser Ser Arg Pro Thr Thr Tyr His Tyr Lys Asn Ile Tyr Gln Glu Ser
1               5                   10                  15

Tyr Gln Gln Arg Asn Pro Ala Val Lys
            20                  25

<210> SEQ ID NO 155
<211> LENGTH: 25
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (25)..(25)
<223> OTHER INFORMATION: Site for Biotin attachment

<400> SEQUENCE: 155

Ser Ser Arg Pro Val Glu Pro Ala Thr Lys Asn Met Arg Glu Ala Arg
1               5                   10                  15

Ser Ser Thr Gln Met Arg Arg Ile Lys
            20                  25

<210> SEQ ID NO 156
<211> LENGTH: 25
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (25)..(25)
<223> OTHER INFORMATION: Site for Biotin attachment

<400> SEQUENCE: 156

Ser Ser Arg Pro Tyr Leu Leu Pro Lys Asp Gln Thr Thr Ala Pro Gln
1               5                   10                  15

Val Thr Pro Ile Val Gln His Lys Lys
            20                  25
```

```
<210> SEQ ID NO 157
<211> LENGTH: 23
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (23)..(23)
<223> OTHER INFORMATION: Site for Biotin attachment

<400> SEQUENCE: 157

Ser Ser Arg Pro Glu Phe Pro Tyr Tyr Asn Asp Asn Pro Pro Asn Pro
1               5                   10                  15

Glu Arg His Thr Leu Arg Lys
            20

<210> SEQ ID NO 158
<211> LENGTH: 20
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (20)..(20)
<223> OTHER INFORMATION: Site for Biotin attachment

<400> SEQUENCE: 158

Ser Ser Arg Pro Asp Leu Gly Thr Phe Pro Asn Arg Thr Leu Lys Met
1               5                   10                  15

Ala Ala His Lys
            20

<210> SEQ ID NO 159
<211> LENGTH: 20
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (20)..(20)
<223> OTHER INFORMATION: Site for Biotin attachment

<400> SEQUENCE: 159

Ser Ser Arg Pro Phe Asp Gly Ile Gly Leu Gly Thr Ala Thr Arg His
1               5                   10                  15

Gln Asn Arg Lys
            20

<210> SEQ ID NO 160
<211> LENGTH: 20
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (20)..(20)
<223> OTHER INFORMATION: Site for biotin attachment

<400> SEQUENCE: 160

Ser Ser Arg Pro Gln Ala Ala Gln Val His Met Met Gln His Ser Arg
1               5                   10                  15

Pro Thr Thr Lys
            20
```

```
<210> SEQ ID NO 161
<211> LENGTH: 23
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (23)..(23)
<223> OTHER INFORMATION: Site for biotin attachment

<400> SEQUENCE: 161

Ser Ser Arg Pro Ser Glu Ala Arg Ala Arg Thr Phe Asn Asp His Thr
1               5                   10                  15

Thr Pro Met Pro Ile Ile Lys
            20

<210> SEQ ID NO 162
<211> LENGTH: 23
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (23)..(23)
<223> OTHER INFORMATION: Site for biotin attachment

<400> SEQUENCE: 162

Ser Ser Arg Pro Glu Leu Asp His Asp Ser Arg His Tyr Met Asn Gly
1               5                   10                  15

Leu Gln Arg Lys Val Thr Lys
            20

<210> SEQ ID NO 163
<211> LENGTH: 23
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (23)..(23)
<223> OTHER INFORMATION: Site for biotin attachment

<400> SEQUENCE: 163

Ser Ser Arg Pro Gly Pro Gln His Val Leu Met Gln Asp Thr His Gln
1               5                   10                  15

Gly Tyr Ala Phe Asp Asn Lys
            20

<210> SEQ ID NO 164
<211> LENGTH: 25
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (25)..(25)
<223> OTHER INFORMATION: Site for biotin attachment

<400> SEQUENCE: 164

Ser Ser Arg Pro Thr Thr Gly Ser Ser Gln Ala Asp Thr Ser Ala
1               5                   10                  15

Ser Met Ser Ile Val Pro Ala His Lys
            20                  25
```

```
<210> SEQ ID NO 165
<211> LENGTH: 23
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (23)..(23)
<223> OTHER INFORMATION: Site for biotin attachment

<400> SEQUENCE: 165

Ser Ser Arg Pro Thr Tyr Gln Gly Val Pro Ser Trp Pro Ala Val Ile
1               5                   10                  15

Asp Asp Ala Ile Arg Arg Lys
            20

<210> SEQ ID NO 166
<211> LENGTH: 23
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (23)..(23)
<223> OTHER INFORMATION: Site for biotin attachment

<400> SEQUENCE: 166

Ser Ser Arg Pro Val Asn Pro Asn Trp Val Glu Thr Gln Ala Leu His
1               5                   10                  15

Gln Pro Pro Gly Asn Thr Lys
            20

<210> SEQ ID NO 167
<211> LENGTH: 23
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (23)..(23)
<223> OTHER INFORMATION: Site for biotin attachment

<400> SEQUENCE: 167

Ser Ser Arg Pro Ile Tyr Pro Asn Glu Ser Met Ser Thr Ser Asn Val
1               5                   10                  15

Arg Gly Pro Tyr His Pro Lys
            20

<210> SEQ ID NO 168
<211> LENGTH: 25
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (25)..(25)
<223> OTHER INFORMATION: Site for biotin attachment

<400> SEQUENCE: 168

Ser Ser Arg Pro His Asp Pro Asn His Leu Thr His Gln Ala Arg Thr
1               5                   10                  15

Ile Tyr Arg Asn Ala Asn His Thr Lys
            20                  25
```

```
<210> SEQ ID NO 169
<211> LENGTH: 25
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (25)..(25)
<223> OTHER INFORMATION: Site for biotin attachment

<400> SEQUENCE: 169

Ser Ser Arg Pro Ala Pro Pro Thr Tyr Gln Thr Ala Ser Tyr Pro His
1               5                   10                  15

Asn Leu Pro Ser Lys Arg Lys Met Lys
            20                  25

<210> SEQ ID NO 170
<211> LENGTH: 25
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (25)..(25)
<223> OTHER INFORMATION: Site for biotin attachment

<400> SEQUENCE: 170

Ser Ser Arg Pro Gln Val Pro Asp Tyr Leu Ser Pro Thr His Gln Lys
1               5                   10                  15

Lys Ala Phe Leu Glu Ile Pro Thr Lys
            20                  25

<210> SEQ ID NO 171
<211> LENGTH: 25
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (25)..(25)
<223> OTHER INFORMATION: Site for biotin attachment

<400> SEQUENCE: 171

Ser Ser Arg Pro His Lys Asn Glu Asn Ile Met Gln Tyr Asn Val Asn
1               5                   10                  15

Asp Arg Trp His Ile Thr Pro Ala Lys
            20                  25

<210> SEQ ID NO 172
<211> LENGTH: 20
<212> TYPE: PRT
<213> ORGANISM: artificial sequence
<220> FEATURE:
<223> OTHER INFORMATION: synthetic construct

<400> SEQUENCE: 172

Ala Ile Glu Tyr Gln His Ser Ala Thr Thr Pro Trp Thr Met Arg Thr
1               5                   10                  15

Arg Leu Pro Pro
            20

<210> SEQ ID NO 173
<211> LENGTH: 20
<212> TYPE: PRT
```

<213> ORGANISM: artificial sequence
<220> FEATURE:
<223> OTHER INFORMATION: synthetic construct

<400> SEQUENCE: 173

Glu Phe Tyr Pro Phe Ala Glu Val Pro Pro Glu Lys Ser Gly Ile Gly
1               5                   10                  15

Arg Gln Val Phe
            20

<210> SEQ ID NO 174
<211> LENGTH: 20
<212> TYPE: PRT
<213> ORGANISM: artificial sequence
<220> FEATURE:
<223> OTHER INFORMATION: synthetic construct

<400> SEQUENCE: 174

Gly Val His Gln Tyr Ser Arg Pro Thr Val Pro Ser Tyr Leu Trp Thr
1               5                   10                  15

Ser Gly Gln His
            20

<210> SEQ ID NO 175
<211> LENGTH: 20
<212> TYPE: PRT
<213> ORGANISM: artificial sequence
<220> FEATURE:
<223> OTHER INFORMATION: synthetic construct

<400> SEQUENCE: 175

Gly Tyr Gln Pro His Tyr Val Asp His Thr Ile Gly Trp Gln Pro Met
1               5                   10                  15

Ile Arg Pro Asn
            20

<210> SEQ ID NO 176
<211> LENGTH: 20
<212> TYPE: PRT
<213> ORGANISM: artificial sequence
<220> FEATURE:
<223> OTHER INFORMATION: synthetic construct

<400> SEQUENCE: 176

Gln Phe Asn Gln Thr Ser His Ser Phe Met His Gly Thr Ser Gly Tyr
1               5                   10                  15

Val Pro Gly Lys
            20

<210> SEQ ID NO 177
<211> LENGTH: 20
<212> TYPE: PRT
<213> ORGANISM: artificial sequence
<220> FEATURE:
<223> OTHER INFORMATION: synthetic construct

<400> SEQUENCE: 177

Ser Phe Ser Trp His Arg Gly Asp Trp Glu Leu Gly His Gln Ser Lys
1               5                   10                  15

Thr Met Gly Met
            20

<210> SEQ ID NO 178
<211> LENGTH: 20
<212> TYPE: PRT

<213> ORGANISM: artificial sequence
<220> FEATURE:
<223> OTHER INFORMATION: synthetic construct

<400> SEQUENCE: 178

Ser Met Trp His Asp Ile Thr Lys Arg Tyr Arg Asn Pro Ser Glu Met
1               5                   10                  15

Val Ser Ala Tyr
            20

<210> SEQ ID NO 179
<211> LENGTH: 20
<212> TYPE: PRT
<213> ORGANISM: artificial sequence
<220> FEATURE:
<223> OTHER INFORMATION: synthetic construct

<400> SEQUENCE: 179

Thr His Gly Asn Lys His Gln Ser Trp Thr Tyr Pro Ser Glu Ile Asn
1               5                   10                  15

His Lys Asn Tyr
            20

<210> SEQ ID NO 180
<211> LENGTH: 20
<212> TYPE: PRT
<213> ORGANISM: artificial sequence
<220> FEATURE:
<223> OTHER INFORMATION: synthetic construct

<400> SEQUENCE: 180

Trp His Glu Pro His Gln Phe Ser Gly Glu Asn Thr Asp Tyr Ser Ser
1               5                   10                  15

Ser Met Gly Thr
            20

<210> SEQ ID NO 181
<211> LENGTH: 20
<212> TYPE: PRT
<213> ORGANISM: artificial sequence
<220> FEATURE:
<223> OTHER INFORMATION: synthetic construct

<400> SEQUENCE: 181

Thr His Gly Asn Lys His Gln Ser Trp Thr Tyr Pro Ser Glu Ile Asn
1               5                   10                  15

His Lys Asn Tyr
            20

<210> SEQ ID NO 182
<211> LENGTH: 16
<212> TYPE: PRT
<213> ORGANISM: artificial sequence
<220> FEATURE:
<223> OTHER INFORMATION: synthetic construct

<400> SEQUENCE: 182

Asp Gly Tyr Lys Leu Gln Thr Ser Leu Asp Trp Gln Met Trp Asn Pro
1               5                   10                  15

<210> SEQ ID NO 183
<211> LENGTH: 16
<212> TYPE: PRT
<213> ORGANISM: artificial sequence
<220> FEATURE:
<223> OTHER INFORMATION: synthetic construct

<400> SEQUENCE: 183

Phe Pro Ser Lys Trp Tyr Asn His His Arg His Ile Thr Gly His Val
1               5                   10                  15

<210> SEQ ID NO 184
<211> LENGTH: 16
<212> TYPE: PRT
<213> ORGANISM: artificial sequence
<220> FEATURE:
<223> OTHER INFORMATION: synthetic construct

<400> SEQUENCE: 184

Gly Gly Met Gly Ala Leu Glu Ser Tyr Arg Gln Trp Asn His Leu Ala
1               5                   10                  15

<210> SEQ ID NO 185
<211> LENGTH: 16
<212> TYPE: PRT
<213> ORGANISM: artificial sequence
<220> FEATURE:
<223> OTHER INFORMATION: synthetic construct

<400> SEQUENCE: 185

Gly Ile Asn Lys Gly Gln Arg Pro Pro Trp Glu Ser Trp His Glu Asn
1               5                   10                  15

<210> SEQ ID NO 186
<211> LENGTH: 16
<212> TYPE: PRT
<213> ORGANISM: artificial sequence
<220> FEATURE:
<223> OTHER INFORMATION: synthetic construct

<400> SEQUENCE: 186

Gly Tyr Gly Gln Tyr Val Ser Gln Gln Thr Trp Ala His Ser Asn Lys
1               5                   10                  15

<210> SEQ ID NO 187
<211> LENGTH: 16
<212> TYPE: PRT
<213> ORGANISM: artificial sequence
<220> FEATURE:
<223> OTHER INFORMATION: synthetic construct

<400> SEQUENCE: 187

His Asp His Leu Ser Trp Trp Gly Gln Phe Asp Arg Gln Asn Leu Leu
1               5                   10                  15

<210> SEQ ID NO 188
<211> LENGTH: 16
<212> TYPE: PRT
<213> ORGANISM: artificial sequence
<220> FEATURE:
<223> OTHER INFORMATION: synthetic construct

<400> SEQUENCE: 188

Met Pro Gly His Gln Glu Ser Ile Lys Val Gln Asn Trp Asn Arg Val
1               5                   10                  15

<210> SEQ ID NO 189
<211> LENGTH: 16
<212> TYPE: PRT
<213> ORGANISM: artificial sequence
<220> FEATURE:
<223> OTHER INFORMATION: synthetic construct

<400> SEQUENCE: 189

-continued

```
Asn Leu His Ser Pro Trp Pro Ser His Ala Ala His His Trp Ser Thr
1               5                   10                  15

<210> SEQ ID NO 190
<211> LENGTH: 16
<212> TYPE: PRT
<213> ORGANISM: artificial sequence
<220> FEATURE:
<223> OTHER INFORMATION: synthetic construct

<400> SEQUENCE: 190

Asn Gln Gln Met Lys Leu Val Pro Gln His Trp His Arg Ala Gln Pro
1               5                   10                  15

<210> SEQ ID NO 191
<211> LENGTH: 16
<212> TYPE: PRT
<213> ORGANISM: artificial sequence
<220> FEATURE:
<223> OTHER INFORMATION: synthetic construct

<400> SEQUENCE: 191

Ser Glu Lys Trp Phe Asn Pro Gly Pro Trp Pro Lys Leu Ala Thr Gln
1               5                   10                  15
```

PEPTIDE-BASED TOOTH WHITENING REAGENTS

This application claims the benefit of U.S. Provisional Patent Application U.S. Provisional Patent Application No. 61/164,476, filed Mar. 30, 2009.

FIELD OF THE INVENTION

The invention relates to the use of peptide-based reagents to improve the cosmetic appearance of teeth. More specifically, peptide-based reagents that couple polymer-coated white colorants to teeth are provided. Oral care compositions comprising the present peptide-based reagents are also provided.

BACKGROUND OF THE INVENTION

The cosmetic appearance of teeth is of great importance to many individuals. These individuals typically desire a "bright" smile and white teeth. Unfortunately, the surface color of teeth generally dulls and discolors over time due to the absorbent nature of dental material.

Tooth coloration is influenced by a combination of intrinsic, such as age and genetics, and extrinsic factors, such as staining caused by various foods, beverages, medications, and tobacco use. Even with regular brushing and flossing, exposure to staining and discoloring substances over many years can cause noticeable discoloration. As such, there is a need for products and processes to quickly and safely whiten teeth.

One solution to the problem of tooth discoloration is the application of veneer facings made of porcelain, composites or ceramic. However, the application of veneer facings is expensive and requires the assistance of trained dental professional.

Bleaching agents may also be used to whiten teeth. The application of the bleaching agent may also require the assistance of a dental professional (i.e., application of concentrated oxidizing agents) and/or multiple applications and may not achieve the desired degree of whitening. Over-the-counter bleaching products typically use lower concentrations of the bleaching agent(s) and often require repeated application of the product. However, the use of bleaching agents has been associated with several undesirable side effects including chemical burns, irritation to the gums, and an increase in tooth sensitivity.

White colorants may also be used to whiten teeth. The non-toxic colorants are typically white pigments or a combination of white pigments with other non-white pigments to achieve a more "natural" white appearance. However, the use of pigments to improve the cosmetic appearance of teeth generally lacks the required durability to achieve the desired cosmetic effect.

There have been various attempts to enhance the binding durability of tooth whitening agents. U.S. Patent Application Publication No. 2005-0069501 to Ibrahim et al. describes the use of a siloxane adhesive and a whitening particulate (hydroxyapatite powder) as a tooth whitening composition. PCT publication WO2006/068011 by Shimako et al. discloses a tooth whitening composition comprising (A) one or more pigments, (B) pullulan, and (C) one or more members selected from lysozyme, cationized cellulose and poly lysine, wherein the components (B) and (C) are used to attach the metal oxide powder on the tooth surface. Neither reference discloses a tooth whitening system comprising a peptide-based reagent suitable for enhancing the durability of a polymer-coated white colorant.

Short peptides having strong affinity for various body surfaces have been identified using a biopanning technique, such as phage display (U.S. Pat. Nos. 7,220,405; 7,309,482; and 7,285,264; U.S. Patent Application Publication Nos. 2005-0226839; 2007-0196305; 2006-0199206; 2007-0065387; 2008-0107614; 2007-0110686; and 2006-0073111; and published PCT applications WO2008/054746; WO2004/048399, and WO2008/073368). However, peptide-based reagents comprising at least one portion having affinity for a tooth surface and at least one portion having affinity for a polymer-coated whitening agent are not described.

U.S. Patent Application Publication No. 2007/0065387 to Beck et al. describes the use of peptide-based reagent comprising at least one portion having strong affinity for hair or skin and at least one portion having affinity for a polymer-coated colorant. Oral care compositions comprising a peptide-based reagent and at least one polymer-coated white colorant are not provided. No tooth-binding peptides or cellulose acetate-binding peptides are described.

The problem to be solved is to provide compositions and methods for delivery of a polymer-coated white colorant to a tooth surface for whitening teeth.

SUMMARY OF THE INVENTION

Peptide-based reagents and methods of using the present reagents to whiten teeth are provided. The peptide-based reagents may be used in conjunction with at least one polymer-coated white colorant to whiten teeth.

Oral care compositions comprising at least one of the present peptide-based reagents are also provided. In a preferred embodiment, the oral care compositions further comprise at least one polymer-coated white colorant, such as a polymer-coated white pigment.

In one embodiment, a peptide-based reagent is provided selected from the group consisting of:

a) a peptide-based reagent having the general structure:

$[(TBP)_m\text{-}(PBP)_n]_x$; and b) a peptide-based reagent having the general structure:

$[[(TBP)_y\text{-}S_q]_m\text{-}[(PBP)_z\text{-}S_r]_n]_p$;

wherein
i) TBP is a tooth-binding peptide;
ii) PBP is a polymer-binding peptide;
iii) S is a spacer;
iv) m, n, x, y and z independently range from 1 to about 10;
v) p is from 1 to 5; and
vi) q an r are each independently 0 or 1, provided that both q and r may not be 0.

In one aspect, the present peptide-based reagents comprise polymer-binding peptides ranging from 7 amino acids to 50 amino acids in length and the tooth-binding peptides ranging from 7 to 50 amino acids in length. In a preferred embodiment, the tooth-binding peptide is from about 7 to about 25 amino acids in length and has a binding affinity for a tooth surface, measured as an MB50 value, equal to or less than $10^{-5}$ M.

In another aspect, the present peptide peptide-based reagents comprise at least one tooth-binding peptide having an amino acid sequence selected from the group consisting of SEQ ID NOs: 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, and 108.

In another aspect, the present peptide-based reagents comprise at least one tooth-binding peptide having an amino acid sequence selected from the group consisting of SEQ ID NOs: 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, and 191.

In another aspect, the present peptide-based reagent comprises a polymer-binding peptide the binds to a polymer selected from the group consisting of cellulose acetate, polyacrylates, polymethacrylates, polymethylmethacrylates, polycarbonates, polystyrene, polypropylene, polyethylene terephthalate, polyurethanes, polypeptides, lignin, polysaccharides, modified polysaccharides, polyamides, polyimides, polyaramides, polyethers, silicones, methicones, dimethicones and copolymers comprising at least one monomer from methacylates, acrylates or styrene.

In a preferred aspect, the polymer-binding peptide comprises an amino acid sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, and 118.

In another aspect, the polymer-coated white colorant may be coupled directly to at least one of the above tooth-binding peptides. As such, a peptide-based reagent having the following structure is also provided:
a) $(TBP)_k$-PCWC, wherein
  i) TBP is a tooth-binding peptide;
  ii) PCWC is a polymer-coated white colorant; and
  iii) k ranges from 1 to about 10,000; and
b) $[(TBP)_v\text{-}L]_k$-PCWC, wherein
  i) TBP is a tooth-binding peptide;
  ii) PCWC is a polymer-coated white colorant;
  iii) L is a spacer;
  iv) v ranges from 1 to about 50; and
  v) k ranges from 1 to about 10,000.

In another embodiment, a method for whitening teeth is provided comprising:
a) providing at least one polymer-coated white colorant;
b) providing a composition comprising at least one of the present peptide-based reagents; and
c) contacting a tooth surface with the at least one polymer-coated white colorant of (a) and the composition of (b) whereby said tooth surface is whitened.

In another embodiment, a method of delivering a polymer-coated white colorant to a tooth surface is provided comprising:
a) providing at least one polymer-coated white colorant;
b) providing a composition comprising at least one of the present peptide-based reagents; and
c) applying said at least one polymer-coated pigment of (a) with the composition of (b) to a tooth surface for a period of time sufficient for the peptide-based tooth whitening reagent in composition of (b) to bind to the polymer-coated white colorant and the tooth surface.

In a further embodiment, the above methods may further comprise a step (d): applying a composition comprising a polymeric sealant; wherein the polymeric sealant is selected from the group consisting of poly(allylamine), acrylates, acrylate copolymers, polyurethanes, carbomers, methicones, amodimethicones, polyethylenene glycol, beeswax, siloxanes, copolymers of methyl vinyl ether and maleic anhydride, linear and cross linked polyvinylpyrrolidone homopolymers, and combinations thereof.

The present peptide-based reagents may be used in oral care compositions. As such, an oral care composition is also provided comprising at least one of the present peptide based-reagents and at least one polymer-coated white colorant. In a preferred aspect, the oral care composition further comprises at least one of the present peptide-based reagents in an orally-acceptable carrier medium.

In another aspect, a composition comprising at least one cellulose acetate coated pigment is provided. In a preferred aspect, an oral care composition comprising at least one cellulose acetate-coated pigment in an orally-acceptable carrier medium is also provided.

In another aspect, said cellulose acetate-coated pigment may comprise a core pigment particle coated with a first layer of silicon dioxide followed by a second layer applied over the said first layer of silicon dioxide wherein the second layer is cellulose acetate.

In another embodiment, the present peptide-based reagents comprise at least one cellulose acetate-binding peptide having an amino acid sequence selected from the group consisting of SEQ ID NOs: 60, 61, 62, 63, 64, 65, 66, 67, and 118.

BRIEF DESCRIPTION OF THE BIOLOGICAL SEQUENCES

The invention can be more fully understood from the following detailed description and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOS: 1-67 and 118 are the amino acid sequence of polymer-binding peptides. SEQ ID NOs: 1-27 are sequences of peptides that bind to polymethylmethacrylate, SEQ ID NOs: 28-34 are sequences of peptides bind to polypropylene, SEQ ID NOs 35-43 are sequences of peptides that bind to polytetrafluoroethylene, SEQ ID NOs: 44-49 are sequences of peptides that bind to nylon, SEQ ID NOs: 50-56 are sequences of peptides that bind to polyethylene, SEQ ID NOs: 57-59 are sequences of peptides that bind to polystyrene, SEQ ID NOs: 60-67, and 118 are sequences of peptides that bind to cellulose acetate.

SEQ ID NO: 68 is the nucleic acid sequence of an oligonucleotide primer used to sequence phage DNA.

SEQ ID NOs: 69-108 and 119-149 are amino acid sequences of tooth-binding peptides. SEQ ID NOs: 69-88, 109-149, and 152-191 are sequences of peptides that bind to tooth pellicle. SEQ ID NOs: 69-108 are sequences of peptides that bind to tooth enamel.

SEQ ID NO: 109 is the amino acid sequence of the Caspase 3 cleavage site.

SEQ ID NOs: 110-115 are the amino acid sequences of peptide spacers.

SEQ ID NO: 116 is the amino acid sequence of a peptide-based reagent (DE020).

SEQ ID NO: 117 is the nucleic acid sequence of expression vector pKSI(C4)E-HC77643.

SEQ ID NO: 150 is the amino acid sequence of a peptide used as a control in Example 13.

SEQ ID NO: 151 is the amino acid sequence of an N-terminal tag described in Example 14.

DETAILED DESCRIPTION

Provided are peptide-based reagents, oral care compositions comprising one or more of the present reagents, and methods of their use. The peptide-based reagent may comprise a first portion comprising one or more tooth-binding peptides and a second portion comprising one or more polymer-binding peptides. The first and second portions may be optionally separated by one or more spacers. The individual tooth-binding and/or polymer-binding peptides may optionally be separated by one or more spacers.

In another embodiment, peptide-based whitening reagents comprising a polymer-coated white colorant coupled directly, or through an optional spacer, to a tooth-binding peptide are also provided.

The white colorant is coated with a polymer such that peptides having an affinity for the polymer, identified by combinatorial methods as described below, will bind to the polymer coating. The polymer coating may be formed from many different organic and biological polymers including, but not limited to cellulose acetate, polyacrylates, polymethacrylates, polymethylmethacrylates, polycarbonates, polystyrene, polypropylene, polyethylene terephthalate, polyurethanes, polypeptides, lignin, polysaccharides, modified polysaccharides, polyamides, polyimides, polyaramides, polyethers, silicones, methicones, dimethicones and copolymers (e.g., block and graft copolymers) comprising at least one monomer from methacylates, acrylates or styrene.

The following definitions are used herein and should be referred to for interpretation of the claims and the specification.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" refers to modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the term "invention" or "present invention" is a non-limiting term and is not intended to refer to any single embodiment of the particular invention but encompasses all possible embodiments as described in the specification and the claims.

As used herein, the term "peptide" refers to two or more amino acids joined to each other by peptide bonds or modified peptide bonds.

As used herein, "TBP" means tooth-binding peptide. A tooth-binding peptide is a peptide that binds with high affinity to a tooth surface.

The term "tooth surface" will refer to a surface comprised of tooth enamel (typically exposed after professional cleaning or polishing) or tooth pellicle (a surface comprising salivary glycoproteins). Hydroxyapatite can be coated with salivary glycoproteins to mimic a natural tooth pellicle surface (tooth enamel is predominantly comprised of hydroxyapatite).

As used herein, the terms "pellicle" and "tooth pellicle" will refer to the thin film (typically ranging from about 20 nm to about 200 μm thick) derived from salivary glycoproteins which forms over the surface of the tooth crown. Daily tooth brushing tends to only remove a portion of the pellicle surface while abrasive tooth cleaning and/or polishing (typically by a dental professional) will expose more of the tooth enamel surface.

As used herein, the terms "enamel" and "tooth enamel" will refer to the highly mineralized tissue which forms the outer layer of the tooth. The enamel layer is composed primarily of crystalline calcium phosphate (i.e., hydroxyapatite) along with water and some organic material. In one embodiment, the tooth surface is selected from the group consisting of tooth enamel and tooth pellicle.

As used herein, "TSBP" means target surface-binding peptide(s). The target surface-binding peptides described herein may refer to tooth-binding peptides and polymer-binding peptides. The target-surface-binding peptides typically range in size from 7 to about 50 amino acids in length. Individual target surface-binding peptides may be referred to herein as a binding "fingers". Linking together multiple "fingers" forms a binding domain or binding "hand" for the respective target surface. In one embodiment, each "finger" is a combinatorially-generated peptide isolated using biopanning, such as phage display or mRNA display As used herein, the term "tooth-binding peptide" will refer to a peptide that binds to tooth enamel or tooth pellicle. In one embodiment, the tooth-binding peptides are from about 7 amino acids to about 50 amino acids in length, more preferably, from about 7 amino acids to about 25 amino acids in length, most preferably from about 7 to about 20 amino acids in length. In a preferred embodiment, the tooth-binding peptides are combinatorially-generated peptides. The tooth-binding peptides ("fingers") may be linked together to form tooth-binding domains ("hands").

As used herein, "PBP" means polymer-binding peptide. A polymer-binding peptide is a peptide that binds with high affinity to a specified polymer. The polymer is used to coat the white colorant. As such, the polymer coating provides a binding interface between the polymer-binding peptide and the white colorant. The polymer-binding peptide is selected based on the polymer used to coat the white colorant. A non-limiting list of polymer-binding peptides is provided in Table A. In one embodiment, the polymer-binding peptides are from about 7 amino acids to about 50 amino acids in length, more preferably, from about 7 amino acids to about 25 amino acids in length, most preferably from about 7 to about 20 amino acids in length. In one embodiment, the polymer-binding peptide is a combinatorially-generated peptide. The polymer-binding peptides ("fingers") may be linked together to form polymer-binding domains ("hands").

As used herein, "S" and "L" mean spacer. The spacer may be an organic spacer and/or a peptide spacer. In one embodiment, the spacer is selected from the group consisting of ethanolamine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, ethyl alkyl chain, propyl alkyl chain, hexyl alkyl chain, steryl alkyl chains, cetyl alkyl chains, and palmitoyl alkyl chains.

In another embodiment, the spacer is a peptide spacer. In one embodiment, the spacer or linker is a peptide linker. In one aspect, the peptide linker comprises 1 to 50 amino acids in length, preferably 1 to 25 amino acids, and most preferably 1 to 10 amino acids in length. In one aspect, the peptide spacer comprises amino acids selected from the group consisting of proline, lysine, glycine, alanine, serine, threonine, and combinations thereof. In a further aspect, the peptide spacer may have an amino acid sequence selected from the group consisting of SEQ ID NOs: 109-115. Depending upon the location of the peptide spacer in the peptide-based reagent, the peptide spacer may also be referred to as a "peptide linker" or a "peptide bridge". In one embodiment, the "spacer" may be a peptide linker. In another embodiment, the spacer may be a peptide bridge used to separate two or more binding domains.

As used herein, a "polymer" is a natural or synthetic compound of usually high molecular weight consisting of repeated linked units. In one embodiment, the natural polymer used to coat the white colorant is not comprised of polynucleotides, polypeptides or combinations thereof.

As used herein, the terms "polymer-coated white colorant" and "white colorant" are abbreviated as "PCWC" and mean a polymer-coated colorant particle capable of providing a whitening effect when coupled to a tooth surface.

As used herein, the terms "peptide-based reagent" and "peptide-based whitening reagent" will be used to refer to a single chain peptide comprising at least one portion having affinity for a tooth surface and at least one portion having affinity for a polymer comprising an effective amount of the corresponding polymer. The peptide-based reagent may range in size from about 14 to about 600 amino acids in length and is not comprised of an immunoglobulin fold and does not require scaffold-assisted binding (i.e., the present peptide-based reagent is not comprised of a naturally-occurring scaffold protein used in scaffold-assisted binding; See Binz, H. et al. (2005) *Nature Biotechnology* 23, 1257-1268 for a review of various scaffold proteins used in scaffold-assisted binding). In a preferred aspect, the peptide-based reagent is about 14 to about 200 amino acids in length. The peptide-based reagent is typically comprised of a first domain having affinity for a tooth surface and a second domain having affinity for a surface comprising the respective polymer. The peptide-based reagent may further comprise a "peptide bridge" separating the first domain from the second domain. The first and/or second domains may be comprised of a single peptide "finger" or may be comprised of a plurality of target surface-binding peptides, optionally separated with one or more peptide linkers.

As used herein, the term "whitening" refers to a change in visual appearance of a tooth, preferably such that the tooth has a brighter shade. An increase in white can be determined visually or may be measured by colorimetry as described below.

As used herein, the term "pigment" means an insoluble colorant. A wide variety of organic and inorganic pigments alone or in combination may be used in the present invention.

As used herein, the term "pigment lake" or "lake" refers to a pigment manufactured by precipitating a dye with an inert binder, usually a metallic salt.

The terms "coupling" and "coupled" as used herein refer to any chemical association and includes both covalent and non-covalent interactions. In one embodiment, non-covalent interactions are used to couple the polymer-coated white colorant to the tooth surface using the present peptide-based reagents.

The term "stringency" as it is applied to the selection of the target surface-binding peptides (e.g., tooth-binding peptides, polymer-binding peptides), refers to the concentration of the eluting agent (usually detergent) used to elute peptides from the target surface. Higher concentrations of the eluting agent provide more stringent conditions. Many of the present tooth-binding and polymer-binding peptides were selected under highly stringent conditions (i.e. those resistant to washing conditions that included 0.5 wt % TWEEN®).

The term "peptide-tooth complex" means structure comprising a peptide bound to a tooth surface via a binding site on the peptide.

As used herein, the term "peptide-polymer complex" means structure comprising a peptide bound to the surface of a specified polymer via a binding site on the peptide. The polymer may be coated on a solid support, such as a metal oxide pigment.

As used herein, the term "effective amount of polymer" or "effective amount of polymeric coating" refers to an amount of polymer that provides a surface capable of binding to one or more of the present polymer-binding peptides, preferably with strong affinity. One of skill in the art can determine an effective amount by measuring an increase in binding of the polymer-coated white colorant to a tooth surface when used in combination with one or more of the present peptide-based reagents.

The term "$MB_{50}$" refers to the concentration of the binding peptide that gives a signal that is 50% of the maximum signal obtained in an ELISA-based binding assay (see U.S. Published Patent Application No. 2005-0226839; hereby incorporated by reference). The $MB_{50}$ provides an indication of the strength of the binding interaction or affinity of the components of the complex. The lower the value of $MB_{50}$, the stronger the interaction of the peptide with its corresponding substrate.

As used herein, the terms "binding affinity" and "affinity" refer to the strength of the interaction of a binding peptide (such as target surface-binding peptides, target surface-binding domains, and peptide reagents) with its respective substrate. The binding affinity may be reported in terms of the $MB_{50}$ value as determined in an ELISA-based binding assay or as a $K_D$ (equilibrium dissociation constant) value, which may be deduced using surface plasmon resonance (SPR).

As used herein, the terms "strong affinity" and "high affinity" refer to a binding affinity, as measured as an $MB_{50}$ value of $K_D$ value, of $10^{-4}$ M or less, preferably less than $10^{-5}$ M, more preferably less than $10^{-6}$ M, more preferably less than $10^{-7}$ M, even more preferably less than $10^{-8}$ M, and most preferably less than $10^{-9}$ M.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any naturally-occurring amino acid (or as defined herein) | Xaa | X |

"Gene" or genetic construct" refers to a nucleic acid fragment that expresses a specific protein, optionally including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

As used herein, the term "genetic construct" refers to a series of contiguous nucleic acids useful for modulating the genotype or phenotype of an organism. Non-limiting examples of genetic constructs include but are not limited to a nucleic acid molecule, an open reading frame, a gene, a plasmid, and the like.

As used herein, the term "peptide-based" refers to an interfacial material comprised of a compound pertaining to or having the nature or the composition of the peptide class. Interfacial refers to the quality of the peptide-based material described herein as connecting one material to another.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, $5^{th}$ Ed. Current Protocols and John Wiley and Sons, Inc., N.Y., 2002.

Target Surface-Binding Peptides

The present peptide-based reagents are comprised of at least one tooth-binding peptide (TBP). In another embodiment, the peptide-based reagents are comprised of at least one tooth-binding peptide and at least one polymer-binding peptide (PBP). The peptide-based reagents optionally comprise one or more spacers.

Tooth-binding peptides as defined herein are peptide sequences that bind with high affinity to mammalian teeth, preferably human teeth. The tooth surface may be tooth enamel or tooth pellicle, the acquired glycoprotein coating on teeth.

Examples of tooth-binding peptides having been disclosed in co-pending and co-owned U.S. Patent Application Publication No. 2008-0280810 and U.S. Provisional Patent Application No. 61/164,476 and are provided in Table A and Tables 14, 16, and 18. In one embodiment, the tooth-binding peptide comprises an amino acid sequence selected from the group consisting of SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, and 191. In a preferred embodiment, the tooth-binding peptide comprises an amino acid sequence selected from the group consisting of SEQ ID NOs: 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, and 191.

Polymer-binding peptides have been previously reported. Peptides having a binding affinity to polymer and plastic surfaces have been identified using phage display. For example, Adey et al., (Gene 156:27-31 (1995)) describe peptides that bind to polystyrene and polyvinyl chloride surfaces. Cunningham et al. describes in several co-pending and co-owned U.S. patent applications peptides that bind to polymethylmethacrylate ("PMMA"; U.S. App. Pub. No. 2007/0265431), polypropylene (U.S. App. Pub. No. 2007/0264720), nylon (U.S. App. Pub. No. 2007/0141629), polytetrafluoroethylene ("PTFE"; U.S. App. No. 11/607, 734), polyethylene ("PE"; U.S. App. Pub. No. 2007/0141628), and polystyrene ("PS"; U.S. App. Pub. No. 2007/0261775). Additionally, peptides that bind to polyurethane (Murray et al., U.S. App. Pub. No. 2002/0098524), polyethylene terephthalate (O'Brien et al., co-pending and commonly owned U.S. App. Pub. No. 2005/0054752), and polystyrene, polyurethane, polycarbonate, and nylon (Grinstaff et al., U.S. App. Pub. No. 2003/0185870) have also been reported.

In another embodiment, the polymer-binding peptide comprises an amino acid sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, and 118. In one aspect, the white colorant is coated with cellulose acetate. As such, and in another embodiment, the polymer-binding peptide is a cellulose acetate-binding peptide. In a further embodiment, the cellulose acetate-binding peptide comprises an amino acid sequence selected from the group consisting of SEQ ID NOs: 60, 61, 62, 63, 64, 65, 66, 67, and 118. In a preferred embodiment, the cellulose acetate-binding peptide comprises an amino acid sequence selected from the group consisting of SEQ ID NOs: 61, 62, 63, and 118. In a further embodiment, the cellulose acetate-binding peptide comprises the amino acid sequence SEQ ID NO: 118.

Peptides having an affinity for a selected target surface (i.e., "target surface-binding peptides") may be obtained using combinatorial methods or may be empirically generated. The tooth surface-binding peptides may have a binding affinity for a tooth surface, as measured by $MB_{50}$ values, of less than or equal to about $10^{-3}$M, preferably less than or equal to about $10^{-4}$ M, more preferably less than or equal to about $10^{-5}$ M, more preferably less than or equal to about $10^{-6}$ M, even more preferably less than or equal to about $10^{-7}$ M, and even more preferably less than or equal to about $10^{-8}$ M. In one embodiment, the term "high affinity" or "strong affinity" will be used to describe tooth surface-binding peptides or polymer-binding peptides having a binding affinity, as measured by $MB_{50}$ value, of less than or equal to about $10^{-5}$M, preferably less than or equal to about $10^{-6}$ M, more preferably less than or equal to about $10^{-7}$ M, and even more preferably less than or equal to about $10^{-8}$.

The generation of random libraries of peptides is well known and may be accomplished by a variety of techniques including, but not limited to bacterial display (Kemp, D. J.; Proc. Natl. Acad. Sci. USA 78(7): 4520-4524 (1981); yeast display (Chien et al., Proc Natl Acad Sci USA 88(21): 9578-82 (1991)), combinatorial solid phase peptide synthesis (U.S. Pat. No. 5,449,754; U.S. Pat. No. 5,480,971; U.S. Pat. No. 5,585,275 and U.S. Pat. No. 5,639,603), phage display technology (U.S. Pat. No. 5,223,409; U.S. Pat. No. 5,403,484; U.S. Pat. No. 5,571,698; and U.S. Pat. No. 5,837,500), ribosome display (U.S. Pat. No. 5,643,768; U.S. Pat. No. 5,658, 754; and U.S. Pat. No. 7,074,557), and mRNA display technology (PROFUSION™; U.S. Pat. No. 6,258,558; U.S. Pat. No. 6,518,018; U.S. Pat. No. 6,281,344; U.S. Pat. No. 6,214, 553; U.S. Pat. No. 6,261,804; U.S. Pat. No. 6,207,446; U.S. Pat. No. 6,846,655; U.S. Pat. No. 6,312,927; U.S. Pat. No. 6,602,685; U.S. Pat. No. 6,416,950; U.S. Pat. No. 6,429,300; U.S. Pat. No. 7,078,197; and U.S. Pat. No. 6,436,665). Techniques to generate such biological peptide libraries are described in Dani, M., J. of Receptor & Signal Transduction Res., 21(4):447-468 (2001). Additionally, phage display libraries are available commercially from companies such as New England BioLabs (Beverly, Mass.).

A preferred method to randomly generate peptides is by phage display. Phage display is an in vitro selection technique in which a peptide or protein is genetically fused to a coat protein of a bacteriophage, resulting in display of the fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

More specifically, after a suitable library of peptides has been generated or purchased, the library is then contacted with an appropriate amount of the test substrate. The library of peptides is dissolved in a suitable solution for contacting the sample. The sample (i.e. target material have a target surface) is typically suspended in solution or may be immobilized on a plate or bead. A preferred solution is a buffered aqueous saline solution containing a surfactant. A suitable solution is Tris-buffered saline (TBS) with 0.5% TWEEN® 20. The solution may additionally be agitated by any means in order to increase the mass transfer rate of the peptides to the target sample/surface, thereby shortening the time required to attain maximum binding.

Upon contact, a number of the randomly generated peptides will bind to the target surface to form a peptide-target surface complex, for example, a peptide-siliceous particle complex. Unbound peptide may be removed by washing. After all unbound material is removed, peptides having varying degrees of binding affinities for the test surface may be fractionated by selected washings in buffers having varying stringencies. Increasing the stringency of the buffer used increases the required strength of the bond between the peptide and target surface in the peptide-target surface complex.

A number of substances may be used to vary the stringency of the washing solution in the peptide selection process including, but not limited to acids (pH 1.5-3.0), bases (pH 10-12.5), salts of high concentrations such as MgCl$_2$ (3-5 M) and LiCl (5-10 M), ethylene glycol (25-50%), dioxane (5-20%), thiocyanate (1-5 M), guanidine (2-5 M), urea (2-8 M), and surfactants of various concentrations such as SDS (sodium dodecyl sulfate), DOC (sodium deoxycholate), Nonidet P-40, Triton X-100, shampoo (useful when selecting peptides for use in personal care compositions, such as a commercial shampoo formulation), TWEEN® 20, wherein TWEEN® 20 is more typical. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that peptides having increasing binding affinities for target surface substrates may be eluted by repeating the selection process using buffers with increasing stringencies. The eluted peptides can be identified and sequenced by any means known in the art.

As many of the peptide-based reagents may be used in personal care products comprising significant amounts of surfactants/detergents (for example, sodium lauryl sulfate (SLS) is commonly used in oral care products such as toothpaste), the stringency of the washing steps may be increased to select only those peptides having the highest binding affinity. In one embodiment, the washing conditions includes a surfactant/detergent, such as a commercially available shampoo. In another embodiment, the washing conditions will include at least 1 wt % surfactant/detergent (e.g. shampoo), preferably at least 5 wt %, even more preferably at least 10 wt %, even more preferably at least 20 wt %, and most preferably at least 30 wt % surfactant/detergent. In one embodiment, peptides that are resistant to washing conditions including a specified surfactant/detergent will be referred to herein as "surfactant/detergent resistant" (or "shampoo resistant" if shampoo formulation used).

Thus, the following method for generating the target surface-binding peptides may be used. A library of combinatorially generated phage-peptides is contacted with the target surface of interest (e.g., a tooth surface or a polymeric surface used to coat the white colorant), to form phage peptide-target surface complexes. The phage-peptide-target surface complex is separated from uncomplexed peptides and unbound substrate, and the bound phage-peptides from the phage-peptide-target surface complexes is eluted from the complex, preferably by acid treatment. Then, the eluted phage-peptides are identified and sequenced. To identify peptide sequences that bind to one substrate but not to another, for example peptides that bind to another surface (i.e., a "non-target" surface; for example, another inorganic material or a body surface such as hair, skin, nail, etc.), a subtractive panning step may be added. Specifically, the library of combinatorially generated phage-peptides is first contacted with the non-target to remove phage-peptides that bind to it. Then, the non-binding phage-peptides are contacted with the desired substrate and the above process is followed. Alternatively, the library of combinatorially generated phage-peptides may be contacted with the non-target and the desired substrate simultaneously. Then, the phage-peptide-target surface complexes are separated from the phage-peptide-non-target complexes and the method described above is followed for the desired phage-peptide-target surface complexes.

In one embodiment, a modified phage display screening method for isolating peptides with a higher affinity for the target surface is used. In the modified method, the phage-peptide-target surface complexes are formed as described above. Then, these complexes are treated with an elution buffer. Any of the elution buffers described above may be used. Preferably, the elution buffer is an acidic solution. Then, the remaining, elution-resistant phage-peptide-target surface complexes are used to directly infect a bacterial host cell, such as E. coli ER2738. The infected host cells are grown in an appropriate growth medium, such as LB (Luria-Bertani) medium, and this culture is spread onto agar, containing a suitable growth medium, such as LB medium with IPTG (isopropyl β-D-thiogalactopyranoside) and S-GAL™. After growth, the plaques are picked for DNA isolation and are sequenced to identify the peptide sequences with a high binding affinity for the target surface of interest.

In another embodiment, PCR may be used to identify the elution-resistant phage-peptides from the modified phage display screening method, described above, by directly carrying out PCR on the phage-peptide-target surface complexes using the appropriate primers, as described by Janssen et al. in U.S. App. Pub. No. 2003/0152976, which is incorporated herein by reference.

Examples of various target surface-binding peptides are provided in Table A.

TABLE A

Examples of Target Surface-Binding Peptides

| Surface* | Amino Acid Sequence | SEQ ID NO: | Reference |
|---|---|---|---|
| PMMA | IPWWNIRAPLNA | 1 | US 2007-0265431 |
| PMMA | TAVMNVVNNQLS | 2 | US 2007-0265431 |
| PMMA | VPWWAPSKLSMQ | 3 | US 2007-0265431 |
| PMMA | MVMAPHTPRARS | 4 | US 2007-0265431 |
| PMMA | TYPNWAHLLSHY | 5 | US 2007-0265431 |
| PMMA | TPWWRIT | 6 | US 2007-0265431 |
| PMMA | DLTLPFH | 7 | US 2007-0265431 |
| PMMA | GTSIPAM | 8 | US 2007-0265431 |
| PMMA | HHKHVVA | 9 | US 2007-0265431 |

TABLE A-continued

Examples of Target Surface-Binding Peptides

| Surface* | Amino Acid Sequence | SEQ ID NO: | Reference |
|---|---|---|---|
| PMMA | HHHKHFM | 10 | US 2007-0265431 |
| PMMA | HHHRHQG | 11 | US 2007-0265431 |
| PMMA | HHWHAPR | 12 | US 2007-0265431 |
| PMMA | APWHLSSQYSGT | 13 | US 2007-0065387 |
| PMMA | GYCLRVDEPTVCSG | 14 | US 2007-0065387 |
| PMMA | HIHPSDNFPHKNRTH | 15 | US 2007-0065387 |
| PMMA | HTHHDTHKPWPTDDHRNSSV | 16 | US 2007-0065387 |
| PMMA | PEDRPSRTNALHHNAHHHNA | 17 | US 2007-0065387 |
| PMMA | TPHNHATTNHHAGKK | 18 | US 2007-0065387 |
| PMMA | EMVKDSNQRNTRISS | 19 | US 2007-0065387 |
| PMMA | HYSRYNPGPHPL | 20 | US 2007-0065387 |
| PMMA | IDTFYMSTMSHS | 21 | US 2007-0065387 |
| PMMA | PMKEATHPVPPHKHSETPTA | 22 | US 2007-0065387 |
| PMMA | YQTSSPAKQSVG | 23 | US 2007-0065387 |
| PMMA | HLPSYQITQTHAQYR | 24 | US 2007-0065387 |
| PMMA | TTPKTTYHQSRAPVTAMSEV | 25 | US 2007-0065387 |
| PMMA | DRIHHKSHHVTTNHF | 26 | US 2007-0065387 |
| PMMA | WAPEKDYMQLMK | 27 | US 2007-0065387 |
| PP | TSDIKSRSPHHR | 28 | US 2007-0264720 |
| PP | HTQNMRMYEPWF | 29 | US 2007-0264720 |
| PP | LPPGSLA | 30 | US 2007-0264720 |
| PP | MPAVMSSAQVPR | 31 | US 2007-0264720 |
| PP | NQSFLPLDFPFR | 32 | US 2007-0264720 |
| PP | SILSTMSPHGAT | 33 | US 2007-0264720 |
| PP | SMKYSHSTAPAL | 34 | US 2007-0264720 |
| PTFE | ESSYSWSPARLS | 35 | US 11/607,734 |
| PTFE | GPLKLLHAWWQP | 36 | US 11/607,734 |
| PTFE | NALTRPV | 37 | US 11/607,734 |
| PTFE | SAPSSKN | 38 | US 11/607,734 |
| PTFE | SVSVGMKPSPRP | 39 | US 11/607,734 |
| PTFE | SYYSLPPIFHIP | 40 | US 11/607,734 |
| PTFE | TFTPYSITHALL | 41 | US 11/607,734 |
| PTFE | TMGFTAPRFPHY | 42 | US 11/607,734 |
| PTFE | TNPFPPPPSSPA | 43 | US 11/607,734 |
| nylon | KTPPTRP | 44 | US 2007-0141629 |
| nylon | VINPNLD | 45 | US 2007-0141629 |
| nylon | KVWIVST | 46 | US 2007-0141629 |
| nylon | AEPVAML | 47 | US 2007-0141629 |

TABLE A-continued

Examples of Target Surface-Binding Peptides

| Surface* | Amino Acid Sequence | SEQ ID NO: | Reference |
|---|---|---|---|
| nylon | AELVAML | 48 | US 2007-0141629 |
| nylon | HSLRLDW | 49 | US 2007-0141629 |
| PE | HNKSSPLTAALP | 50 | US 2007-0141628 |
| PE | LPPWKHKTSGVA | 51 | US 2007-0141628 |
| PE | LPWWLRDSYLLP | 52 | US 2007-0141628 |
| PE | VPWWKHPPLPVP | 53 | US 2007-0141628 |
| PE | HHKQWHNHPHHA | 54 | US 2007-0141628 |
| PE | HIFSSWHQMWHR | 55 | US 2007-0141628 |
| PE | WPAWKTHPILRM | 56 | US 2007-0141628 |
| PS | TSTASPTMQSKIR | 57 | US 2007-0261775 |
| PS | KRNHWQRMHLSA | 58 | US 2007-0261775 |
| PS | SHATPPQGLGPQ | 59 | US 2007-0261775 |
| CA | ATTPPSGKAAAHSAARQKGN | 60 | Disclosed herein |
| CA | DTIHPNKMKSPSSPL | 61 | Disclosed herein |
| CA | NGNNHTDIPNRSSYTGGSFA | 62 | Disclosed herein |
| CA | SDETGPQIPHRRPTW | 63 | Disclosed herein |
| CA | ATTPPSGKAAAHSAARQKGNK | 64 | Disclosed herein |
| CA | DTIHPNKMKSPSSPLK | 65 | Disclosed herein |
| CA | NGNNHTDIPNRSSYTGGSFAK | 66 | Disclosed herein |
| CA | SDETGPQIPHRRPTWK | 67 | Disclosed herein |
| CA | VRPNLHRKAKAKPDHKQSENRKVPFYSHGSSG | 118 | US 60/972,307 |
| Tooth (pellicle) | AHPESLGIKYALDGNSDPHA | 69 | US 11/877,692 |
| Tooth (pellicle) | ASVSNYPPIHHLATSNTTVN | 70 | US 11/877,692 |
| Tooth (pellicle) | DECMEPLNAAHCWR | 71 | US 11/877,692 |
| Tooth (pellicle) | DECMHGSDVEFCTS | 72 | US 11/877,692 |
| Tooth (pellicle) | DLCSMQMMNTGCHY | 73 | US 11/877,692 |
| Tooth (pellicle) | DLCSSPSTWGSCIR | 74 | US 11/877,692 |
| Tooth (pellicle) | DPNESNYENATTVSQPTRHL | 75 | US 11/877,692 |
| Tooth (pellicle) | EPTHPTMRAQMHQSLRSSSP | 76 | US 11/877,692 |
| Tooth (pellicle) | GNTDTTPPNAVMEPTVQHKW | 77 | US 11/877,692 |
| Tooth (pellicle) | NGPDMVQSVGKHKNS | 78 | US 11/877,692 |
| Tooth (pellicle) | NGPEVRQIPANFEKL | 79 | US 11/877,692 |

TABLE A-continued

Examples of Target Surface-Binding Peptides

| Surface* | Amino Acid Sequence | SEQ ID NO: | Reference |
|---|---|---|---|
| Tooth (pellicle) | NNTSADNPPETDSKHHLSMS | 80 | US 11/877,692 |
| Tooth (pellicle) | NNTWPEGAGHTMPSTNIRQA | 81 | US 11/877,692 |
| Tooth (pellicle) | NPTATPHMKDPMHSNAHSSA | 82 | US 11/877,692 |
| Tooth (pellicle) | NPTDHIPANSTNSRVSKGNT | 83 | US 11/877,692 |
| Tooth (pellicle) | NPTDSTHMMHARNHE | 84 | US 11/877,692 |
| Tooth (pellicle) | QHCITERLHPPCTK | 85 | US 11/877,692 |
| Tooth (pellicle) | TPCAPASFNPHCSR | 86 | US 11/877,692 |
| Tooth (pellicle) | TPCATYPHFSGCRA | 87 | US 11/877,692 |
| Tooth (pellicle) | WCTDFCTRSTPTSTSRSTTS | 88 | US 11/877,692 |
| Tooth (enamel) | APPLKTYMQERELTMSQNKD | 89 | US 11/877,692 |
| Tooth (enamel) | EPPTRTRVNNHTVTVQAQQH | 90 | US 11/877,692 |
| Tooth (enamel) | GYCLRGDEPAVCSG | 91 | US 11/877,692 |
| Tooth (enamel) | LSSKDFGVTNTDQRTYDYTT | 92 | US 11/877,692 |
| Tooth (enamel) | NFCETQLDLSVCTV | 93 | US 11/877,692 |
| Tooth (enamel) | NTCQPTKNATPCSA | 94 | US 11/877,692 |
| Tooth (enamel) | PSEPERRDRNIAANAGRFNT | 95 | US 11/877,692 |
| Tooth (enamel) | THNMSHFPPSGHPKRTAT | 96 | US 11/877,692 |
| Tooth (enamel) | TTCPTMGTYHVCWL | 97 | US 11/877,692 |
| Tooth (enamel) | YCADHTPDPANPNKICGYSH | 98 | US 11/877,692 |
| Tooth (enamel) | AANPHTEWDRDAFQLAMPPK | 99 | US 11/877,692 |
| Tooth (enamel) | DLHPMDPSNKRPDNPSDLHT | 100 | US 11/877,692 |
| Tooth (enamel) | ESCVSNALMNQCIY | 101 | US 11/877,692 |
| Tooth (enamel) | HNKADSWDPDLPPHAGMSLG | 102 | US 11/877,692 |
| Tooth (enamel) | LNDQRKPGPPTMPTHSPAVG | 103 | US 11/877,692 |
| Tooth (enamel) | NTCATSPNSYTCSN | 104 | US 11/877,692 |

TABLE A-continued

Examples of Target Surface-Binding Peptides

| Surface* | Amino Acid Sequence | SEQ ID NO: | Reference |
|---|---|---|---|
| Tooth (enamel) | SDCTAGLVPPLCAT | 105 | US 11/877,692 |
| Tooth (enamel) | TIESSQHSRTHQQNYGSTKT | 106 | US 11/877,692 |
| Tooth (enamel) | VGTMKQHPTTTQPPRVSATN | 107 | US 11/877,692 |
| Tooth (enamel) | YSETPNDQKPNPHYKVSGTK | 108 | US 11/877,692 |

*PMMA means polymethylmethacrylate, PP means polypropylene, PTFE means polytetrafluoroethylene, PE means polyethylene, PS means polystyrene, CA means cellulose acetate.

Tooth Surfaces

The tooth surface is a natural surface on mammalian teeth that can serve as a substrate for a binding peptide. In one embodiment, the tooth surface is selected from tooth enamel and tooth pellicle.

Samples of tooth surfaces are available from a variety of sources. For example, extracted mammalian teeth, such as bovine and/or human teeth are commercially available. Extracted human teeth (with or without a pellicle coating) may also be obtained from dental offices. Additionally, hydroxyapatite, available in many forms, for example, from Berkeley Advanced Biomaterials, Inc. (San Leandro, Calif.), may be used (preferably coated with salivary glycoproteins to form an acquired pellicle surface) as a model for studying teeth-binding peptides (see co-owned and co-pending U.S. application Ser. No. 11/877,692).

White Colorants

The present invention is based on the use of a polymer-coated white colorant. Any number of orally-acceptable white colorants may be used. In one embodiment, the white colorant is a white pigment.

A wide variety of organic and inorganic pigments alone or in combination may be used in the present invention, so long as the colorant or combination of colorants result in the desired cosmetic effect (i.e. whiter teeth). Pigments for use in personal care products are well known in the art (see for example Green et al. (WO 0107009), *CFTA International Color Handbook*, 2$^{nd}$ ed., Micelle Press, England (1992) and *Cosmetic Handbook*, US Food and Drug Administration, FDA/IAS Booklet (1992)), and are available commercially from various sources (for example Bayer, Pittsburgh, Pa.; Ciba-Geigy, Tarrytown, N.Y.; ICI, Bridgewater, N.J.; Sandoz, Vienna, Austria; BASF, Mount Olive, N.J.; and Hoechst, Frankfurt, Germany).

The size (as defined the average equivalent diameter or "average diameter") of the polymer-coated pigments may vary. In one embodiment the average diameter will range from about 10 nanometers (nm) to about 50 micrometers (μ), preferably about 10 nm to about 20 μm, more preferably 50 nm to about 20 μm, and most preferably about 100 nm to about 2 μm. The pigments can be partially or completely coated in the desired polymer and may be porous or non-porous. The polymer coating thickness on the white colorant may vary. Typically, the coating thickness ranges from about 2 nm to about 50 nm, preferably about 5 nm to about 20 nm.

In a preferred embodiment, the polymer-coated white colorant is a polymer-coated white pigment. However, to achieve a more natural appearance it may be necessary to also include one or more non-white pigments. As such, any of the following pigments or combinations thereof may also be used.

Exemplary pigments may include, but are not limited to, D&C Red No. 36, D&C Red No. 30, D&C Orange No. 17, Green 3 Lake, Ext. Yellow 7 Lake, Orange 4 Lake, and Red 28 Lake; the calcium lakes of D&C Red Nos. 7, 11, 31 and 34, the barium lake of D&C Red No. 12, the strontium lake D&C Red No. 13, the aluminum lakes of FD&C Yellow No. 5, of FD&C Yellow No. 6, of FD&C No. 40, of D&C Red Nos. 21, 22, 27, and 28, of FD&C Blue No. 1, of D&C Orange No. 5, of D&C Yellow No. 10, the zirconium lake of D&C Red No. 33; CROMOPHTAL® Yellow 131 AK (Ciba Specialty Chemicals), SUNFAST® Magenta 122 (Sun Chemical) and SUNFAST® Blue 15:3 (Sun Chemical), iron oxides, calcium carbonate, calcium phosphate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide, silicon dioxide, black titanium dioxide, titanium dioxide nanoparticles, zinc oxide, aluminum oxide, tin oxide, calcium oxide, magnesium oxide, barium oxide, ultramarine blue, bismuth citrate, and white minerals such as hydroxyapatite, and Zircon (zirconium silicate), and carbon black particles.

In one embodiment, the white colorant of the polymer-coated white colorant is a white pigment selected from the group consisting of white mineral particles (e.g., calcium phosphate in various structural forms and hydroxyapatite), white metal oxides (e.g., titanium dioxide, titanium dioxide nanoparticles, and zinc oxide), silicon dioxide, zirconium silicate, to name a few. In some embodiments, white mineral particles can comprise a non-toxic mineral or salt that can impart a white color, for example, calcium phosphate in various structural forms, including tetracalcium phosphate, amorphous calcium phosphate, alpha-tricalcium phosphate, beta-tricalcium phosphate and hydroxyapatite. In another embodiment, white metal oxides include any metal oxide that provides a white color, such as titanium oxide, aluminum oxide, tin oxide, calcium oxide, magnesium oxide, barium oxide, zinc oxide or a combination thereof.

In a preferred embodiment, the white colorant of the polymer-coated white colorant is a white pigment selected from the group consisting of calcium phosphate, hydroxyapatite, titanium dioxide, titanium dioxide nanoparticles, zinc oxide, silicon dioxide, zirconium silicate, and a combination thereof. In a more preferred embodiment, the white colorant of the polymer-coated white colorant is a white pigment selected from the group consisting of titanium dioxide, titanium dioxide nanoparticles, zinc oxide, silicon dioxide, zirconium silicate, and a combination thereof. In a further preferred embodiment, the polymer-coated white colorant is a polymer-coated titanium dioxide Pigments, by definition, are substantially insoluble colorants and therefore, are used in dispersed form. The pigment may be dispersed using a dispersant or a self-dispersing pigment may be used. When a dispersant is used to disperse the pigment, the dispersant may be any suitable dispersant known in the art, including, but not limited to, random or structured organic polymeric dispersants, as described below; protein dispersants, such as those described by Brueckmann et al. (U.S. Pat. No. 5,124,438); and peptide-based dispersants, such as those described by O'Brien et al (co-pending and commonly owned U.S. Patent Application Publication No. 2005-0054752). Preferred random organic polymeric dispersants include acrylic polymer and styrene-acrylic polymers. Most preferred are structured dispersants, which include AB, BAB and ABC block copolymers, branched polymers and graft polymers. Preferably the organic polymers comprise monomer units selected from the group consisting of acrylate, methacrylate, butyl methacrylate, 2-ethylhexyl methacrylate, benzyl methacrylate, phenoxyethyl acrylate, ethoxytriethyleneglycol methacrylate, polyethylene glycol methacrylate, polyethylene glycol acrylate, acrylic acid, methacrylic acid, methacrylamide, acrylamide, dimethylaminoethyl methacrylate, hydroxyethyl acrylate, and hydroxyethyl methacrylate, such as those described by Nigan (U.S. Patent Application Publication No. 2004/0232377). Some useful structured polymer dispersants are disclosed in U.S. Pat. No. 5,085,698; EP-A-0556649; and U.S. Pat. No. 5,231,131. Additionally, pigments may be dispersed using a surface active agent comprising lignin sulfonic acids and a polypeptide, as described by Cioca et al. in U.S. Pat. No. 4,494,994.

The pigment may optionally be surface-treated prior to coating with organic polymer. Common surface treatments include, but are not limited to alkyl silane, siloxane, methicone, and dimethicone. Surface treatment increases the range of polymers that can use to coat the pigment surface.

A self-dispersing pigment is a pigment that has been surface modified with chemically attached, dispersibility imparting groups to allow stable dispersion without a separate dispersant. For dispersion in an aqueous carrier medium, surface modification involves addition of hydrophilic groups and most typically ionizable hydrophilic groups. The self-dispersing pigment may be prepared by grafting a functional group or a molecule containing a functional group onto the surface of the pigment, by physical treatment (such as vacuum plasma), or by chemical treatment (for example, oxidation with ozone, hypochlorous acid or the like). A single type or a plurality of types of hydrophilic functional groups may be bonded to one pigment particle. Self-dispersing pigments are described, for example, in U.S. Pat. No. 5,571,311, U.S. Pat. No. 5,609,671, U.S. Pat. No. 5,968,243, U.S. Pat. No. 5,928,419, U.S. Pat. No. 6,323,257, U.S. Pat. No. 5,554,739, U.S. Pat. No. 5,672,198, U.S. Pat. No. 5,698,016, U.S. Pat. No. 5,718,746, U.S. Pat. No. 5,749,950, U.S. Pat. No. 5,803,959, U.S. Pat. No. 5,837,045, U.S. Pat. No. 5,846,307, U.S. Pat. No. 5,895,522, U.S. Pat. No. 5,922,118, U.S. Pat. No. 6,123,759, U.S. Pat. No. 6,221,142, U.S. Pat. No. 6,221,143, U.S. Pat. No. 6,281,267, U.S. Pat. No. 6,329,446, U.S. Pat. No. 6,332,919, U.S. Pat. No. 6,375,317, U.S. Pat. No. 6,287,374, U.S. Pat. No. 6,398,858, U.S. Pat. No. 6,402,825, U.S. Pat. No. 6,468,342, U.S. Pat. No. 6,503,311, U.S. Pat. No. 6,506,245, and U.S. Pat. No. 6,852,156.

Titanium dioxide nanoparticles are described in U.S. Pat. Nos. 5,451,390; 5,672,330; and 5,762,914. Titanium dioxide P25 is an example of a commercial product available from Degussa (Parsippany, N.J.). Other commercial suppliers of titanium dioxide nanoparticles include Kemira (Helsinki, Finland), Sachtleben (Duisburg, Germany) and Tayca (Osaka, Japan).

The titanium dioxide nanoparticles typically have an average particle size diameter of less than 100 nanometers (nm) as determined by dynamic light scattering which measures the particle size distribution of particles in liquid suspension. The nanoparticles are typically agglomerates which may range from about 3 nm to about 6000 nm. In one embodiment, the average particle size of the nanoparticle ranges from about 5 nm to about 100 nm.

Any process known in the art can be used to prepare such particles. The process may involve vapor phase oxidation of titanium halides or solution precipitation from soluble titanium complexes, provided that titanium dioxide nanoparticles are produced. A preferred process to prepare titanium dioxide nanoparticles is by injecting oxygen and titanium halide, preferably titanium tetrachloride, into a high-temperature reaction zone, typically ranging from 400 to 2000° C. Under the high temperature conditions present in the reaction zone, nanoparticles of titanium dioxide are formed having high surface area and a narrow size distribution. The energy source in the reactor may be any heating source such as a plasma torch.

Polymer-Coated White Colorants

The white colorant is coated with a polymeric coating such that peptides having an affinity for the polymer will bind to the polymeric coating. The polymeric coating may be formed from many different organic and biological polymers including, but not limited to cellulose acetate, polyacrylates, polymethacrylates, polymethylmethacrylates, polycarbonates, polystyrene, polypropylene, polyethylene terephthalate, polyurethanes, polypeptides, lignin, polysaccharides, modified polysaccharides, polyamides, polyimides, polyaramides, polyethers, silicones, methicones, dimethicones and copolymers, (e.g., block and graft copolymers) comprising at least one monomer from methacylates, acrylates or styrene. In a preferred embodiment, the polymeric coating is formed from a polymer selected from the group consisting of cellulose acetate, polysaccharides, modified polysaccharides, methacrylates and acrylates.

If a pigment dispersed with a polymeric dispersant, as described above, is used as the white colorant, the polymeric dispersant, may serve as the polymeric coating. The organic polymeric dispersants surrounding the pigment may optionally be cross linked by covalent or ionic bonds, generally after they have been applied to the pigment. Cross-linking increases the permanence and environmental-resistance of the polymeric coating. Any of the polymer dispersants described above may be used. For example, pigments dispersed with a polyacrylate-containing dispersant may be used in conjunction with a polyacrylate-binding peptide. Alternatively, the dispersed pigment may be coated with another polymer as described below.

For pigments and self-dispersing pigments and other particulate white colorants that are not typically used with a polymeric dispersant, the particles may be coated with a polymer using particle coating methods known in the art. Typically, methods used for coating particles are solution-based methods that rely on the application of a polymer solution onto the particle surface, followed by the removal of the solvent. For example, the particulate white colorant may be coated with a polymer by simply mixing the particles with a solution containing the polymer for a time sufficient to coat the particles and then removing the solvent. Additionally, the particulate white colorants may be coated with a polymer using spray coating techniques, such as those described by Guignon et al. (*Drying Technol.* 20:419-447 (2002)). Coatings may also be applied with a Wurster coater (see for example, Cardozo et al., U.S. Patent Application Publication No. 2006-0019860). The white colorants of the invention may also be coated with a polymer using an emulsification-solvent evaporation technique, as described by Rosca et al. (*J. Control Release* 99:271-280 (2004)). Additionally, white colorants may be coated with a polymer using the injector mixer method and apparatus described by Schurr (U.S. Pat. No. 4,430,001 and WO 97/007879). In the injector mixer method, small levels of additives are intensely mixed with powders by simultaneously atomizing the coating liquid and dispersing the particles in a gas injector. The method offers the advantages of low water use and very short contact time, which enables the coating of thermally sensitive materials at high temperatures.

Production of Binding Peptides

The binding peptides (tooth surface-binding peptides, polymer-binding peptides, and the peptide-based reagents) may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the peptides described herein may be prepared using recombinant DNA and molecular cloning techniques. Genes encoding the peptides may be produced in heterologous host cells, particularly in the cells of microbial hosts.

Preferred heterologous host cells for expression of the peptides of the present invention are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species such as *Aspergillus, Trichoderma, Saccharomyces, Pichia, Candida, Yarrowia, Hansenula*, or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*.

A variety of expression systems can be used to produce the peptides of the present invention. Such vectors include, but are not limited to chromosomal, episomal and virus-derived vectors, e.g., vectors derived from bacterial plasmids, from bacteriophage, from transposons, from insertion elements, from yeast episomes, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these could be used to construct chimeric genes for production of the any of the binding peptides of the present invention. These chimeric genes could then be introduced into appropriate microorganisms via transformation to provide high level expression of the peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in *E. coli*.

Initiation control regions or promoters which are useful to drive expression of the chimeric gene in the desired host cell are numerous and familiar to those skilled in the art. Virtually any promoter capable of driving the gene is suitable for producing the binding peptides of the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, pBAD, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

The vector containing the appropriate DNA sequence, as well as an appropriate promoter or control sequence, may be employed to transform an appropriate host to permit the host to express the peptide of the present invention. Cell-free translation systems can also be employed to produce such peptides using RNAs derived from the DNA constructs of the present invention. Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049 and WO 9324631). The secretion signal DNA or facilitator may be located between the expression-controlling DNA and the instant gene or gene fragment, and in the same reading frame with the latter.

Peptide-Based Reagents Comprising at Least One Tooth-Binding Peptide and at Least One Polymer-Binding Peptide Peptide-based reagents are formed by coupling at least one tooth-binding peptide to at least one polymer-binding peptide, either directly or through one or more spacers. The part of the reagent comprising at least one tooth-binding peptide binds strongly to a tooth surface, while the part of the reagent comprising at least one polymer-binding peptide binds strongly to a polymer-coated white colorant, thereby attaching the polymer-coated white colorant to the tooth surface. It is understood that one of skill in the art will select polymer-binding peptides that binds with high affinity to the polymer used to coat the white colorant.

In one embodiment, the peptide-based reagent comprises a peptide having the general structure:

$[(TBP)_m\text{-}(PBP)_n]_x$, wherein a) TBP is a tooth-binding peptide;
b) PBP is a polymer-binding peptide; and
c) m, n, and x independently range from 1 to about 10.

In another embodiment of the peptide described above, m and n are preferably from 1 to about 5, and x may be 1 to about 10.

In another embodiment, the peptide-based reagent comprises a peptide having the general structure:

$[[(TBP)_y\text{-}S_q]_m\text{-}[(PBP)_z\text{-}S_r]_n]_p$, wherein a) TBP is a tooth-binding peptide;
b) PBP is a polymer-binding peptide;
c) S is a spacer;
d) m, n, y and z independently range from 1 to about 10;
e) p is from 1 to 5; and
f) q and r are each independently 0 or 1, provided that both q and r may not be 0.

In a preferred embodiment, m and n independently range from 1 to about 3, and y and z independently range from 1 to about 5.

An example of a peptide-based reagent (peptide conjugate) is provided as SEQ ID NO: 116.

The coupling interaction may be a covalent bond or a non-covalent interaction, such as hydrogen bonding, electrostatic interaction, hydrophobic interaction, or Van der Waals interaction. In the case of a non-covalent interaction, the peptide-based reagents may be prepared by mixing at least one tooth-binding peptide and at least one polymer-binding peptide and the optional spacer (if used) and allowing sufficient time for the interaction to occur. The unbound materials may be separated from the resulting peptide-based reagents using methods known in the art, for example, gel permeation chromatography.

The peptide-based reagents may also be prepared by covalently attaching at least one tooth-binding peptide to at least one polymer-binding peptide, either directly or through a spacer. In this embodiment, the polymer-coated white colorant is delivered to the tooth surface using the non-covalent interact between the polymer-binding peptide and the polymer-coated white colorant.

Any known peptide or protein conjugation chemistry may be used to form the peptide-based reagents of the invention. Conjugation chemistries are well-known in the art (see for example, Hermanson, *Bioconjugate Techniques*, Academic Press, New York (1996)). Suitable coupling agents include, but are not limited to, carbodiimide coupling agents, diacid chlorides, diisocyanates and other difunctional coupling reagents that are reactive toward terminal amine and/or carboxylic acid groups on the peptides. The preferred coupling agents are carbodiimide coupling agents, such as 1-ethyl-3-(3-dimethylaminopropyl)-carbodiimide (EDC) and N,N'-dicyclohexyl-carbodiimide (DCC), which may be used to activate carboxylic acid groups. Additionally, it may be necessary to protect reactive amine or carboxylic acid groups on the peptides to produce the desired structure for the peptide-based reagent. The use of protecting groups for amino acids, such as t-butyloxycarbonyl (t-Boc), are well known in the art (see for example Stewart et al., supra; Bodanszky, supra; and Pennington et al., supra).

The peptide constructs described herein may be prepared using recombinant DNA and molecular cloning techniques described herein. In a preferred embodiment, the peptide-based reagents comprising at least one tooth-binding peptide and at least one polymer-binding peptide (optionally comprising one or more spacers) are prepared using recombinant DNA and molecular cloning techniques described herein.

It may also be desirable to couple the tooth-binding peptide to the polymer-binding peptide via a spacer to form the peptide-based reagent. The spacer serves to separate the binding peptide sequences to ensure that the binding affinity of the individual peptides is not adversely affected by the coupling. The spacer may also provide other desirable properties such as hydrophilicity, hydrophobicity, or a means for cleaving the peptide sequences to facilitate removal of the whitening agent.

The spacer, also referred to herein as the "organic spacer", may be any of a variety of molecules, such as alkyl chains, phenyl compounds, ethylene glycol, amides, esters and the like. Preferred spacers are hydrophilic and have a chain length from 1 to about 100 atoms, more preferably, from 2 to about 30 atoms. Examples of spacers may include, but are not limited to, ethanolamine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl chains, ethyl alkyl chains, propyl alkyl chains, hexyl alkyl chains, steryl alkyl chains, cetyl alkyl chains, palmitoyl alkyl chains, and peptide spacers.

The spacer may be covalently attached to the tooth-binding and polymer-binding peptide sequences using any of the coupling chemistries described above. In order to facilitate incorporation of the spacer, a bifunctional cross-linking agent that contains a spacer and reactive groups at both ends for coupling to the peptides may be used.

Suitable bifunctional cross-linking agents are well known in the art and include, but are not limited to diamines, such a as 1,6-diaminohexane; dialdehydes, such as glutaraldehyde; bis N-hydroxysuccinimide esters, such as ethylene glycol-bis (succinic acid N-hydroxysuccinimide ester), disuccinimidyl glutarate, disuccinimidyl suberate, and ethylene glycol-bis (succinimidylsuccinate); diisocyanates, such as hexamethyl-enediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used.

Examples of heterobifunctional cross-linking agents include, but are not limited to compounds having the following structure:

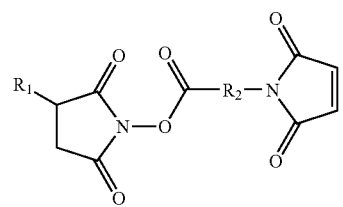

where: $R_1$ is H or a substituent group such as —$SO_3Na$, —$NO_2$, or —Br; and $R_2$ is a spacer such as —$CH_2CH_2$ (ethyl), —$(CH_2)_3$ (propyl), or —$(CH_2)_3C_6H_5$ (propyl phenyl). An example of such a heterobifunctional cross-linking agent is 3-maleimidopropionic acid N-hydroxysuccinimide ester. The N-hydroxysuccinimide ester group of these reagents reacts with amine groups on one peptide, while the maleimide group reacts with thiol groups present on the other peptide. A thiol group may be incorporated into the peptide by adding at least one cysteine group to at least one end of the binding peptide sequence (i.e., the C-terminal end or N-terminal end). Several spacer amino acid residues, such as glycine, may be incorporated between the binding peptide sequence and the terminal cysteine to separate the reacting thiol group from the binding sequence. Moreover, at least one lysine residue may be added to at least one end of the binding peptide sequence, i.e., the C-terminal end or the N-terminal end, to provide an amine group for coupling.

Additionally, the spacer may be a peptide spacer. The preferred peptide spacers comprise the amino acids selected from the group consisting of proline, lysine, glycine, alanine, serine, and mixtures thereof. In addition, the peptide spacer may contain a specific enzyme cleavage site, such as the protease Caspase 3 site, given by SEQ ID NO: 109, which allows for the enzymatic removal of the polymer-coated white colorant from the tooth surface. Examples of peptides spacers include, but are not limited to the sequences given by SEQ ID NOs: 110-115. These peptide spacers may be linked to the binding peptide sequences by any method known in the art. For example, the entire triblock peptide-based reagent may be prepared using the standard peptide synthesis methods described, supra. In addition, the binding peptides and peptide spacer block may be combined using carbodiimide coupling agents, diacid chlorides, diisocyanates and other difunctional coupling reagents that are reactive to terminal amine and/or carboxylic acid groups on the peptides, as described above. Alternatively, the entire triblock peptide-based reagent may be prepared using the recombinant DNA and molecular cloning techniques described supra. The spacer may also be a combination of a peptide spacer and an organic spacer molecule, which may be prepared using the methods described above.

It may also be desirable to have multiple copies of the tooth-binding peptide and the polymer-binding peptide coupled together to enhance the interaction between the peptide-based reagent, the tooth surface, and the polymer-coated white colorant. Either multiple copies of the same tooth-binding peptide and polymer-binding peptide or a combination of different tooth-binding peptides and polymer-binding peptides may be used. The multi-copy peptide-based reagents may comprise various spacers as described above.

In another embodiment, the peptide-based reagent comprises a spacer (S) separating the tooth-binding peptide from the polymer-binding peptide, as described above. Multiple copies of the tooth-binding peptide and the polymer-binding peptide may also be used and the multiple copies of the tooth-binding peptide and the polymer-binding peptide may be separated from themselves and from each other by spacers. In this embodiment, the peptide-based reagent is a "triblock" composition comprising at least one tooth-binding peptide, at least one spacer, and at least one polymer-binding peptides, having the general structure $[[(TBP)_y\text{-}S_q]_m\text{-}[(PBP)_z\text{-}S_r]_n]_p$, where n, m, y, and z independently range from 1 to about 10, p is from 1 to about 5, and where q and r are each independently 0 or 1, provided that both q and r are not 0. Preferably, m and n independently range from 1 to about 3, and y and z range from 1 to about 5.

It should be understood that as used herein "TBP" and "PBP" are generic designations and are not meant to refer to a single tooth-binding peptide or polymer-binding peptide, respectively. Where y or z as used above, is greater than 1, it is well within the scope of the invention to provide for the situation where a series of tooth-binding peptides of same or different sequences and polymer-binding peptides of same or different sequences may form a part of the composition. Additionally, "S" is a generic term and is not meant to refer to a single spacer. Where m and n, as used above for the triblock compositions, are greater than 1, it is well within the scope of the invention to provide for the situation where a series of same or different spacers may form a part of the composition. It should also be understood that these structures do not necessarily represent a covalent bond between the peptides and the optional spacer. As described above, the coupling interaction between the peptides and the optional spacer may be either covalent or non-covalent. In a preferred embodiment, the peptide-based reagent is a linear, recombinantly produced peptide comprising at least one tooth-binding peptide, at least one polymer-binding peptide, and optionally one or more peptide spacers.

Peptide-Based Reagents Comprising at Least One Tooth-Binding Peptide Coupled to a Polymer-Coated White Colorant In another aspect, the peptide based reagent may comprise at least one tooth-binding peptide coupled directly to a polymer-coated white colorant. The tooth-binding peptide is used to couple the polymer-coated white colorant to teeth. The peptide-based reagent may optionally be comprised of one or more spacers. Suitable spacers and suitable coupling chemistry are described above.

In one embodiment, a peptide-based reagent comprising the following structure is also provided:

$(TBP)_k$-PCWC, wherein a) TBP is a tooth-binding peptide;
b) PCWC is a polymer-coated white colorant; and
c) k ranges from 1 to about 10,000.

In another embodiment, the polymer-coated white colorant may be coupled to a tooth-binding peptide through one or more spacers. As such, a peptide-based reagent comprising the following structure is also provided:

$[(TBP)_v\text{-}L]_k$-PCWC, wherein a) TBP is a tooth-binding peptide;
b) PCWC is a polymer-coated white colorant;
c) L is a spacer;
d) v ranges from 1 to about 50; and
e) k ranges from 1 to about 10,000.

It may also be desirable to couple the tooth-binding peptide to the polymer-coated white colorant (PCWC) via a spacer L to form a tooth whitening reagent, provided that spacer L does not adversely affect the binding affinity of the tooth-binding peptide. The spacer L may also provide other desirable properties such as hydrophilicity, hydrophobicity, or a means for cleaving the peptide sequences to facilitate removal of the whitening agent. The spacer L can be an organic spacer or a peptide spacer, which are similarly defined previously for spacer S.

In another embodiment, a peptide-based reagent is also provided comprising a spacer L separating the tooth-binding peptide from the polymer-coated white colorant, as described above. Multiple copies of the tooth-binding peptides may also be used, and the multiple copies of the tooth-binding peptides and the polymer-coated white colorant may be separated from themselves and from each other by different spacers.

Oral Care Compositions

The present invention includes oral care compositions comprising an effective amount of one or more of the present peptide-based reagents and an effective amount of at least one polymer-coated white colorant. As used here, the term "effective amount" is that amount of at least one peptide-based reagent and the amount of at least one polymer-coated white colorant incorporated into the oral care composition to achieve the desired improvement of whiter-appearing teeth.

Methods to apply polymer coating to a particle, such as a white colorant, are well known in the art. Examples of white colorants may include, but are not limited to, white pigments such as titanium dioxide, titanium dioxide nanoparticles and zinc oxide, white minerals such as hydroxyapatite, Zircon (zirconium silicate), and mixtures thereof. However, it may be desirable to further include at least one non-white pigment in an oral care composition to achieve the desired coloration.

The oral care compositions of the invention may be in the form of powder, paste, gel, liquid, ointment, or tablet. Exemplary oral care compositions include, but are not limited to, toothpaste, dental cream, gel or tooth powder, mouth wash, breath freshener, and dental floss. The oral care compositions comprise an effective amount of a peptide-based reagent and a polymer-coated white colorant in an orally acceptable carrier medium. An effective amount of a peptide-based reagent for use in an oral care composition may vary depending on the type of product. Typically, the effective amount of the peptide-based reagent is a proportion from about 0.01% to about 90% by weight relative to the total weight of the composition. Additionally, a mixture of different peptide-based reagents having affinity for different polymer-coated white colorants may be used in the composition. The peptide-based reagents in the mixture need to be chosen so that there is no interaction between the peptides that mitigates the whitening effect. Suitable mixtures of peptide-based reagents may be determined by one skilled in the art using routine experimentation. If a mixture of peptide-based reagents is used in the composition, the total concentration of the reagents is about 0.001% to about 90% by weight relative to the total weight of the composition.

Components of an orally-acceptable carrier medium are described by White et al. in U.S. Pat. No. 6,740,311; Lawler et al. in U.S. Pat. No. 6,706,256; Fuglsang et al. in U.S. Pat. No. 6,264,925; and Ibrahim et al., U.S. App. Pub. No. 2005/0069501, all of which are incorporated herein by reference. For example, the oral care composition may comprise one or more of the following: abrasives, surfactants, antioxidants, chelating agents, fluoride sources, thickening agents, buffering agents, solvents, humectants, carriers, bulking agents, and oral benefit agents, such as enzymes, anti-plaque agents, anti-staining agents, anti-microbial agents, anti-caries agents, anti-inflammatory agents, desensitizing agents, sweetening agents, flavoring agents, breath-freshening agents, coolants, nutrients, and salivating agents.

In another embodiment, the peptide-based reagent is used to detect the presence of a particular surface on teeth (e.g., a diagnostic application). For example, the peptide-based reagent may be used to detect the presence of a pellicle coating on teeth immediately after an abrasive cleaning/polishing procedure (e.g., a dental office cleaning/polishing procedure).

Methods for Whitening a Tooth Surface

The peptide-based reagents may be used in conjunction with a polymer-coated white colorant to whiten teeth. The tooth-binding peptide block of the peptide-based reagent has an affinity for a tooth surface, while the polymer-binding peptide block has an affinity for a polymer-coated white colorant (such as a white pigment). The peptide-based reagent may be present in the same composition as the polymer-coated white colorant, or the peptide-based reagent and the polymer-coated white colorant may be present in two different compositions until use. In one embodiment, an oral care composition comprising at least one peptide-based reagent and at least one polymer-coated white colorant is applied to a tooth surface for a time sufficient for the peptide-based reagent, which is non-covalently coupled to the polymer-coated-white colorant via the polymer-binding peptide block, to bind to the tooth surface. In another embodiment, at least one polymer-coated white colorant is applied to a tooth surface prior to the application of a composition comprising at least one peptide-based reagent. In another embodiment, a composition comprising at least one peptide-based reagent is applied to the tooth surface prior to the application of the polymer-coated white colorant. In another embodiment, at least one polymer-coated white colorant and a composition comprising at least one peptide-based reagent are applied to the tooth surface concomitantly, that is together. Optionally, the composition comprising the peptide-based reagent may be reapplied to the tooth surface after the application of the polymer-coated white colorant and the initial application of the composition comprising the peptide-based reagent. Additionally, a composition comprising a separate polymeric sealant, such as the orally-acceptable GANTREZ® copolymer (copolymers of methyl vinyl ether and maleic anhydride used in commercially-available oral care compositions and available from International Specialty Products, Wayne, N.J.) may be applied to the tooth surface after the application of a composition comprising the polymer-coated white colorant and peptide-based reagent.

In one embodiment, at least one polymer-coated white colorant is applied to the surface of teeth for a time sufficient for the polymer-coated white colorant to bind to the teeth, typically between about 5 seconds to about 60 minutes. Optionally, the teeth may be rinsed to remove the polymer-coated white colorant that has not bound to the teeth. Then, a composition comprising a peptide-based reagent is applied for a time sufficient for the peptide-based reagent to bind to the teeth and the polymer-coated white colorant, typically between about 5 seconds to about 60 minutes. The composition comprising the peptide-based reagent may be rinsed from the teeth or left on the teeth.

In another embodiment, a composition comprising a peptide-based reagent is applied to the teeth for a time sufficient for the tooth-binding peptide block of the peptide-based reagent to bind to the teeth, typically between about 5 seconds to about 60 minutes. Optionally, the teeth may be rinsed to remove the composition that has not bound to the teeth. Then, at least one polymer coated white colorant may be applied to the teeth for a time sufficient for the at least one polymer coated white colorant to bind to the polymer-binding block of the peptide-based reagent, typically between about 5 seconds to about 60 minutes. The unbound polymer-coated white colorant may be rinsed from the teeth or left on the teeth.

In another embodiment, at least one polymer coated white colorant and a composition comprising at least one peptide-based reagent are applied to the teeth concomitantly (or together) for a time sufficient for the peptide-based reagent to bind to teeth and the polymer-coated white colorant, typically between about 5 seconds to about 60 minutes. Optionally, the teeth may be rinsed to remove the unbound polymer coated white colorant and the composition comprising the peptide-based reagent from the teeth.

In another embodiment, at least one polymer coated white colorant is provided as part of a composition comprising at least one peptide-based reagent, for example a tooth whitening composition. The composition comprising the polymer-coated white colorant and the peptide-based reagent is applied to the teeth for a time sufficient for the peptide-based reagent, which is coupled to the polymer-coated white colorant through the polymer-binding peptide block, to bind to the surface of teeth, typically between about 5 seconds to about 60 minutes. The composition comprising the polymer-coated white colorant and the peptide-based reagent may be rinsed from the teeth or left on the teeth.

In any of the methods described above, the composition comprising a peptide-based reagent may be optionally reapplied to the teeth after the application of the polymer coated white colorant and the initial application of the composition comprising the peptide-based reagent in order to further enhance the durability of the colorant.

Additionally, in any of the methods described above, a composition comprising an additional polymeric sealant may be optionally applied to the teeth after the application of the polymer-coated white colorant and the composition comprising a peptide-based reagent in order to further enhance the durability of the colorant. The composition comprising the additional polymeric sealant may be an aqueous solution or an oral care composition, such as a toothpaste or mouthwash, comprising the polymeric sealant (such as GANTREZ® copolymers). Typically, the polymeric sealant is present in the composition at a concentration of about 0.25% to about 10% by weight relative to the total weight of the composition. Additional polymeric sealants well known in the art of personal care products may be used and may include, but are not limited to, poly(allylamine), acrylates, acrylate copolymers, polyurethanes, carbomers, methicones, amodimethicones, polyethylenene glycol, beeswax, siloxanes, PLASDONE® and POLYPLASDONE® (linear and cross linked polyvinylpyrrolidone homopolymers, respectively; available for International Specialty Products), and combinations thereof. The choice of polymeric sealant may be selected based on the particular white colorant and the peptide-based reagent used. The optimum type and amount of additional polymeric sealant may be readily determined by one skilled in the art using routine experimentation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "min" means minute(s), "sec" means second(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "ng" means nanograms, "mg" means milligram(s), "g" means the gravitation constant, "rpm" means revolution(s) per minute, "pfu" means plaque forming unit, "BSA" means bovine serum albumin, "ELISA" means enzyme linked immunosorbent assay, "IPTG" means isopropyl β-D-thiogalactopyranoside, "A" means absorbance, "$A_{450}$" means the absorbance measured at a wavelength of 450 nm, "$OD_{600}$" means the optical density measured at 600 nanometers, "TBS" means Tris-buffered saline, "TBST-X" means Tris-buffered saline containing TWEEN® 20 where "X" is the weight percent of TWEEN® 20, "Xgal" means 5-bromo-4-chloro-3-indolyl-beta-D-galactopyranoside, "SEM" means standard error of the mean, "MW" means molecular weight, "$M_w$," means weight-average molecular weight, "vol %" means volume percent, "wt %" means weight percent, and "RCF" means relative centrifugal field.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma-Aldrich Chemical Company (St. Louis, Mo.), unless otherwise specified.

Example 1

Selection of Tooth Pellicle-Binding Peptides Using Standard Biopanning

The purpose of this Example was to identify phage peptides that bind tooth pellicle using standard phage display biopanning.

The compressed HAP disks (Hydroxyapatite disk, 3 mm diameter) were used to form the pellicles by incubating the disks inside a human mouth for 1.5 hours followed by TBS rinse. The disks were then incubated in SUPERBLOCK® blocking buffer (Pierce Chemical Company, Rockford, Ill.; Prod. #37535) for 1 hour at room temperature, followed by 3 washes with TBST (TBS in 0.05% TWEEN® 20). Libraries of phage containing random peptide inserts ($10^{11}$ pfu) from 7 to 20 amino acids were added to each tube. After 60 minutes of incubation at room temperature and shaking at 50 rpm, unbound phages were removed by aspirating the liquid out of each well followed by 6 washes with 1.0 mL TBS containing the detergent TWEEN® 20 (TBST) at a final concentration of 0.05%.

The sample disks were then transferred to clean tubes and 200 µL of elution buffer consisting of 1 mg/mL BSA in 0.2 M glycine-HCl, pH 2.2, was added to each well and incubated for 10 min to elute the bound phages. Then, 32 µL of neutralization buffer consisting of 1 M Tris-HCl, pH 9.2, was added to each well. The phage particles, which were in the elution buffer as well as on the sample disks, were amplified by incubating with diluted *E. coli* ER2738 cells, from an overnight culture diluted 1:100 in LB medium, at 37° C. for 4.5 h. After this time, the cell culture was centrifuged for 30 seconds and the upper 80% of the supernatant was transferred to a fresh tube, ⅙ volume of PEG/NaCl (20% polyethylene glycol-800, 2.5 M sodium chloride) was added, and the phage was allowed to precipitate overnight at 4° C. The precipitate was collected by centrifugation at 10,000×g at 4° C. and the resulting pellet was resuspended in 1 mL of TBS. This was the first round of amplified stock. The amplified first round phage stock was then tittered according to the standard protocol. For the $2^{nd}$, $3^{rd}$ and $4^{th}$ round of biopanning, more than $2\times10^{11}$ pfu of phage stock from the previous round was used. The biopanning process was repeated for 2 additional rounds under the same conditions as described above. The same biopanning condition was used for the $4^{th}$ round, except the washing solution was TBS with 0.5% TWEEN® 20 instead of 0.05% TWEEN® 20.

After the $4^{th}$ round of biopanning, 95 random single phage plaque lysates were prepared following the manufacture's instructions (New England BioLabs) and the single stranded phage genomic DNA was purified using the QIAprep Spin M13 Kit (Qiagen, Valencia, Calif.) and sequenced at the DuPont Sequencing Facility using –96 gIII sequencing primer (5'-CCCTCATAGTTAGCGTAACG-3'), given as SEQ ID NO: 68. The displayed peptide is located immediately after the signal peptide of gene III. Based on the peptide sequences, 20 phage candidates were selected for further pellicle-binding analysis.

Example 2

Characterization of Tooth Pellicle-Binding Candidates on Pellicle Surface

A total of 20 selected phage candidates (Example 1) were used in a phage ELISA experiment. Purified phage lysates were used for binding to pellicle-coated HAP disks using an anti-M13 phage antibody conjugated to horseradish-peroxidase, followed by the addition of chromogenic agent TMB (3,3',5,5'-tetramethylbenzidine), obtained from Pierce Biotechnology (Item #34021; Rockford, Ill.). The plates were read at $A_{450}$ nm.

For each phage candidate to be tested, the pellicle-coated HAP disks (3 mm diameter) was incubated for 1 h at room temperature with 200 μL of blocking buffer, consisting of 2% non-fat dry milk (Schleicher & Schuell, Inc.) in TBS. The blocking buffer was removed by aspirating the liquid out of each tube. The tube was rinsed 6 times with wash buffer consisting of TBST-0.05%. The wells were filled with 200 μL of TBST-0.5% containing 1 mg/mL BSA (bovine serum albumin) and then 10 μL (over $10^{10}$ pfu) of purified phage stock was added. The samples were incubated at room temperature for 60 min with slow shaking. The non-binding phage were removed by washing 6 times with TBST-0.5%. Then, 100 μL of horseradish peroxidase/anti-M13 antibody conjugate (Amersham USA, Piscataway, N.J.), diluted 1:500 in the blocking buffer, was added and incubated for 1 hour at room temperature. The conjugate solution was removed and was washed 6 times with TBST-0.5%. TMB (3,3',5,5'-tetramethylbenzidine) substrate (200 μL), obtained from Pierce Biotechnology (Rockford, Ill.) was added to each well and the color was allowed to develop for 5 to 30 min, typically for 10 min, at room temperature. Then, stop solution (200 μL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values are given in Table 1.

TABLE 1

Amino Acid Sequences of Pellicle-Binding Peptides

| Phage ID | Amino Acids Sequence | SEQ ID NO. | O.D. at 450 nm |
|---|---|---|---|
| Control | No phage | — | 0.218 |
| Pell 1 | AHPESLGIKYALDGNSDPHA | 69 | 0.739 |
| Pell 2 | ASVSNYPPIHHLATSNTTVN | 70 | 0.75 |
| Pell 3 | DECMEPLNAAHCWR | 71 | 0.49 |
| Pell 4 | DECMHGSDVEFCTS | 72 | 0.664 |
| Pell 5 | DLCSMQMMNTGCHY | 73 | 0.83 |
| Pell 6 | DLCSSPSTWGSCIR | 74 | 0.735 |
| Pell 7 | DPNESNYENATTVSQPTRHL | 75 | 0.831 |
| Pell 8 | EPTHPTMRAQMHQSLRSSSP | 76 | 0.712 |
| Pell 9 | GNTDTTPPNAVMEPTVQHKW | 77 | 0.755 |
| Pell 10 | NGPDMVQSVGKHKNS | 78 | 0.729 |
| Pell 11 | NGPEVRQIPANFEKL | 79 | 0.607 |
| Pell 12 | NNTSADNPPETDSKHHLSMS | 80 | 0.521 |
| Pell 13 | NNTWPEGAGHTMPSTNIRQA | 81 | 0.598 |
| Pell 14 | NPTATPHMKDPMHSNAHSSA | 82 | 0.7 |
| Pell 15 | NPTDHIPANSTNSRVSKGNT | 83 | 0.567 |
| Pell 16 | NPTDSTHMMHARNHE | 84 | 0.578 |
| Pell 17 | QHCITERLHPPCTK | 85 | 0.614 |
| Pell 18 | TPCAPASFNPHCSR | 86 | 0.416 |
| Pell 19 | TPCATYPHFSGCRA | 87 | 0.731 |
| Pell 20 | WCTDFCTRSTPTSTSRSTTS | 88 | 0.715 |

Example 3

Selection of Tooth Enamel-Binding Peptides Using Standard Biopanning

The purpose of this example was to identify phage peptides that bind tooth enamel using standard phage display biopanning.

The unpolished bovine enamel blocks from incisors (3 mm squares) and polished bovine enamel disks from the incisors (3 mm diameter disks) were embedded in wax to form a well with only the intended surfaces exposed. The enamel surfaces were then incubated in SUPERBLOCK® blocking buffer (Pierce Chemical Company, Rockford, Ill.; Prod. #37535) for 1 hour at room temperature, followed by 3 washes with TBST (TBS in 0.05% TWEEN® 20). Libraries of phage containing random peptide inserts ($10^{11}$ pfu) from 7 to 20 amino acids were added to the enamel well for 10 minutes, pre-absorption, to titrate the wax surface, unbound phages were removed by aspirating the liquid out of each well. Then, 100 μL of the same phage library ($10^{11}$ pfu) was added to the enamel well for 60 min incubation at room temperature with slow 50 rpm shaking, followed by 6 washes with 1.0 mL TBS containing the detergent TWEEN® 20 (TBST) at a final concentration of 0.05%.

The enamel blocks (or polished disks) were then cut out of the wax well and transferred to a clean tube and 200 μL of elution buffer consisting of 1 mg/mL BSA in 0.2 M glycine-HCl, pH 2.2, was added to each well and incubated for 10 min to elute the bound phages. Then, 32 μL of neutralization buffer consisting of 1 M Tris-HCl, pH 9.2, was added to each tube. The phage particles, which were in the elution buffer as well as on the enamel blocks, were amplified by incubating with diluted E. coli ER2738 cells, from an overnight culture diluted 1:100 in LB medium, at 37° C. for 4.5 h. After this time, the cell culture was centrifuged for 30 s and the upper 80% of the supernatant was transferred to a fresh tube, ⅙ volume of PEG/NaCl (20% polyethylene glycol-800, 2.5 M sodium chloride) was added, and the phage was allowed to precipitate overnight at 4° C. The precipitate was collected by centrifugation at 10,000×g at 4° C. and the resulting pellet was resuspended in 1 mL of TBS. This was the first round of amplified stock. The amplified first round phage stock was then tittered according to the standard protocol. For the $2^{nd}$ round of biopanning, more than $2×10^{11}$ pfu of phage stock from the previous round was used. The biopanning process was repeated for 1 more rounds under the same conditions as described above. The same biopanning condition was used for the $3^{rd}$ round, except the washing solution was TBS with 0.5% TWEEN® 20 instead of 0.05% TWEEN® 20.

After the $3^{rd}$ round of biopanning, 95 random single phage plaque lysates were prepared following the manufacture's instructions (New England BioLabs) and the single stranded phage genomic DNA was purified using the QIAprep Spin M13 Kit (Qiagen, Valencia, Calif.) and sequenced at the DuPont Sequencing Facility using −96 gIII sequencing primer (5'-CCCTCATAGTTAGCGTAACG-3'), given as SEQ ID NO:68. The displayed peptide is located immediately after the signal peptide of gene III. Based on the peptide sequences, 20 phage candidates were selected for further pellicle binding analysis (Table 2). "BoEn" means bovine enamel and "BoEn P" means polished bovine enamel.

TABLE 2

Tooth Enamel-Binding Peptide Sequences

| Phage ID | Amino Acid Sequence | SEQ ID NO: |
|---|---|---|
| BoEn P1 | APPLKTYMQERELTMSQNKD | 89 |
| BoEn P2 | EPPTRTRVNNHTVTVQAQQH | 90 |
| BoEn P3 | GYCLRGDEPAVCSG | 91 |
| BoEn P4 | LSSKDFGVTNTDQRTYDYTT | 92 |
| BoEn P5 | NFCETQLDLSVCTV | 93 |
| BoEn P6 | NTCQPTKNATPCSA | 94 |
| BoEn P7 | PSEPERRDRNIAANAGRFNT | 95 |
| BoEn P8 | THNMSHFPPSGHPKRTAT | 96 |
| BoEn P9 | TTCPTMGTYHVCWL | 97 |
| BoEn P10 | YCADHTPDPANPNKICGYSH | 98 |
| BoEn 1 | AANPHTEWDRDAFQLAMPPK | 99 |
| BoEn 2 | DLHPMDPSNKRPDNPSDLHT | 100 |

TABLE 2-continued

Tooth Enamel-Binding Peptide Sequences

| Phage ID | Amino Acid Sequence | SEQ ID NO: |
|---|---|---|
| BoEn 3 | ESCVSNALMNQCIY | 101 |
| BoEn 4 | HNKADSWDPDLPPHAGMSLG | 102 |
| BoEn 5 | LNDQRKPGPPTMPTHSPAVG | 103 |
| BoEn 6 | NTCATSPNSYTCSN | 104 |
| BoEn 7 | SDCTAGLVPPLCAT | 105 |
| BoEn 8 | TIESSQHSRTHQQNYGSTKT | 106 |
| BoEn 9 | VGTMKQHPTTTQPPRVSATN | 107 |
| BoEn 10 | YSETPNDQKPNPHYKVSGTK | 108 |

Example 4

Characterization of Tooth Enamel-Binding Peptide Candidates on Enamel Surface

A total of 11 selected phage candidates (Example 3) were used in a phage ELISA experiment. Purified phage lysates were used for binding to the enamel blocks using an anti-M13 phage antibody conjugated to horseradish-peroxidase, followed by the addition of chromogenic agent TMB, obtained from Pierce Biotechnology (Rockford, Ill.). The plates were read at $A_{450}$ nm.

For each phage candidate to be tested, the polished and unpolished enamel blocks were incubated for 1 h at room temperature with 200 μL of blocking buffer, consisting of 2% non-fat dry milk (Schleicher & Schuell, Inc.) in TBS. The blocking buffer was removed by aspirating the liquid out of each tube. The tube was rinsed 6 times with wash buffer consisting of TBST-0.05%. The wells were filled with 200 μL of TBST-0.5% containing 1 mg/mL BSA and then 10 μL (over $10^{10}$ pfu) of purified phage stock was added. The samples were incubated at room temperature for 60 min with slow shaking. The non-binding phage was removed by washing 6 times with TBST-0.5%. Then, 100 μL of horseradish peroxidase/anti-M13 antibody conjugate (Amersham USA, Piscataway, N.J.), diluted 1:500 in the blocking buffer, was added and incubated for 1 h at room temperature. The conjugate solution was removed and was washed 6 times with TBST-0.5%. TMB substrate (200 μL), obtained from Pierce Biotechnology (Rockford, Ill.) was added to each well and the color was allowed to develop for 5 to 30 min, typically for 10 min, at room temperature. Then, stop solution (200 μL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values are given in Tables 3 and 4. "BoEn P" means bovine polished enamel and BoEn means bovine enamel.

TABLE 3

Phage ELISA Results on Polished Enamel-Binding Assay of Selected Phage Candidates

| Phage ID | Amino Acid Sequence | SEQ ID NO: | O.D. at 450 nm |
|---|---|---|---|
| Control | no phage | — | 0.112 |
| BoEn P2 | EPPTRTRVNNHTVTVQAQQH | 90 | 0.641 |
| BoEn P3 | GYCLRGDEPAVCSG | 91 | 0.665 |
| BoEn P5 | NFCETQLDLSVCTV | 93 | 0.797 |
| BoEn P6 | NTCQPTKNATPCSA | 94 | 0.83 |
| BoEn P8 | THNMSHFPPSGHPKRTAT | 96 | 2.02 |

TABLE 4

Phage ELISA Results on Tooth Enamel-Binding Assay of Selected Phage Candidates

| Phage ID | Amino Acid Sequence | SEQ ID NO. | O.D. at 450 nm |
|---|---|---|---|
| Control | no phage | — | 0.193 |
| BoEn 1 | AANPHTEWDRDAFQLAMPPK | 99 | 1.402 |
| BoEn 5 | LNDQRKPGPPTMPTHSPAVG | 103 | 0.944 |
| BoEn 6 | NTCATSPNSYTCSN | 104 | 2.38 |
| BoEn 7 | SDCTAGLVPPLCAT | 105 | 0.892 |
| BoEn 9 | VGTMKQHPTTTQPPRVSATN | 107 | 0.568 |
| BoEn 10 | YSETPNDQKPNPHYKVSGTK | 108 | 3.942 |

Example 5

Preparation of Cellulose Acetate-Coated Metal Oxide Particles

Approximately 20 g of iron oxide pigment (Unipure Red LC381, Sensient Technologies Corp, Milwaukee, Wis.), 10 g of a 10% solution of cellulose acetate in acetone (Eastman Chemical Company, Kingsport, Tenn.; catalog #CA398-10), and 90 g of acetone were mixed in a blender for 50 minutes. The mixture was then transferred to an Erlenmeyer flask with a magnetic stirrer and 50 mL of petroleum ether was slowly added with stirring. The mixture was filtered and the solid was washed with petroleum ether and dried in a vacuum oven at 60° C., yielding 20.2 g of a red solid with a particle size (average equivalent diameter; d50) of 2.5 microns.

Example 6

Selection of Cellulose Acetate-Binding Peptides Using Standard Biopanning

The purpose of this example was to identify phage peptides that bind cellulose acetate coated particles using standard phage display biopanning method.

Commercial iron oxide particles obtained from Sensient Technologies (Unipure Red LC381) were coated with cellulose acetate as described in Example 5. The cellulose acetate-coated iron oxide particles were incubated in SUPER-BLOCK® blocking buffer (Pierce Chemical Company, Rockford, Ill.; Prod. #37535) for 1 hour at room temperature, followed by 3 washes with TBST (TBS in 0.5% TWEEN® 20). Libraries of phage containing random peptide inserts ($10^{11}$ pfu) from 7 to 20 amino acids were added to each tube. After 60 minutes of incubation at room temperature and shaking at 50 rpm, unbound phages were removed by aspirating the liquid out of each well followed by 6 washes with 1.0 mL TBS containing the detergent TWEEN® 20 (TBST, T-0.5%) and 30% of Neutrogena shampoo (Neutrogena Clean Replenishing, Moisturizing Shampoo, Neutrogena Corp., Los Angeles, Calif. 90045).

The particle samples were then transferred to clean tube, and 200 µL of elution buffer consisting of 1 mg/mL BSA in 0.2 M glycine-HCl, pH 2.2, was added to each well and incubated for 10 min at room temperature to elute the bound phages. Then, 32 µL of neutralization buffer consisting of 1 M Tris-HCl, pH 9.2, was added to each tube. The phage particles, which were in the elution buffer as well as on the particles, were amplified by incubating with diluted E. coli ER2738 cells, from an overnight culture diluted 1:100 in LB medium, at 37° C. for 4.5 h. After this time, the cell culture was centrifuged for 30 sec and the upper 80% of the supernatant was transferred to a fresh tube, ⅙ volume of PEG/NaCl (20% polyethylene glyco-800, 2.5 M sodium chloride) was added, and the phage was allowed to precipitate overnight at 4° C. The precipitate was collected by centrifugation at 10,000×g at 4° C. and the resulting pellet was resuspended in 1 mL of TBS. This was the first round of amplified stock. The amplified first round phage stock was then tittered according to the standard protocol. For the $2^{nd}$, $3^{rd}$ and $4^{th}$ round of biopanning, more than $2 \times 10^{11}$ pfu of phage stock from the previous round was used. The biopanning process was repeated under the same conditions as described above.

After the $4^{th}$ round of biopanning, 95 random single phage plaque lysates were prepared following the manufacture's instructions (New England BioLabs) and the single stranded phage genomic DNA was purified using the QIAprep Spin M13 Kit (Qiagen, Valencia, Calif.) and sequenced at the DuPont Sequencing Facility using −96 gIII sequencing primer (5'-CCCTCATAGTTAGCGTAACG-3'), given as SEQ ID NO: 68. The displayed peptide is located immediately after the signal peptide of gene III. Based on the peptide sequences, 30 phage candidates showed significant enrichment were selected for further pellicle binding analysis. The amino acid sequences of selected phage candidates were listed in Table 5.

TABLE 5

Amino Acid Sequences of Cellulose Acetate-Binding Candidates

| Phage ID | Amino Acid Sequence | SEQ ID NO: |
|---|---|---|
| CA-1 | ATTPPSGKAAAHSAARQKGN | 60 |
| CA-2 | DTIHPNKMKSPSSPL | 61 |
| CA-3 | NGNNHTDIPNRSSYTGGSFA | 62 |
| CA-4 | SDETGPQIPHRRPTW | 63 |

Example 7

Characterization of Selected Peptides for Cellulose Acetate-Binding Activities Enzyme-linked immunosorbent assay (ELISA) was used to evaluate the cellulose acetate coated iron oxide particle-binding affinity of the biopanning selected peptide candidates (Example 6; biotinylated peptides phage ID: CA-1 to CA-4). The identified peptides were synthesized using a standard solid-phase synthesis method (see U.S. patent application Ser. No. 11/251/715). All peptides were modified to contain a biotinylated lysine residue at the C-terminus of the amino acid binding sequence for detection purposes (Table 6).

The cellulose acetate-coated iron oxide particles were dispersed in water at 2.5 mg per mL. The dispersion was made by vortex the mix for 1 min, which gave an average particle size of 0.5 µm in diameter. The particle dispersion (1 mL each) was then centrifuged for 2 min at 5000 rpm, the aqueous was removed by aspirating it out of each tube. The tubes were incubated in SUPERBLOCK® blocking buffer (Pierce Chemical Company, Rockford, Ill.; Prod. #37535) for 1 hour at room temperature (~22° C.), followed by 3 washes with TBST (TBS in 0.05% TWEEN® 20). Then tubes were then rinsed 3 times with wash buffer consisting of TBST-0.05% using the same centrifugation and aspiration methods. Peptide binding buffer consisting of 20 µM biotinylated peptides in TBST and 1 mg/mL BSA was added to the particles and incubated for 1 hour at room temperature (~22° C.), followed by 6 TBST washes. Then, the streptavidin-alkaline phosphatase (AP) conjugate (Pierce Chemical Co., Rockford, Ill.) was added to each well at standard concentration and incubated for 1 hour at room temperature, followed by 6 times of washes with TBST. All particles were then transferred to new tubes and then the color development and the absorbance measurements were performed following the manufacturer's standard protocols. The resulting absorbance values, reported as the mean of at least three replicates, and the standard error of the mean (SEM) are given in Table 6.

Example 8

Biological Production of a Triblock Peptide-Based Reagent

The purpose of this Example was to prepare a triblock peptide-based reagent using recombinant DNA and molecular cloning techniques. The method for recombinantly producing the triblock peptide-based reagent is described in United States Patent Application Publication No. 2007-0065387; herein incorporated by reference.

The triblock peptide-based conjugate was comprised of multiple tooth-binding peptide blocks, peptide spacers, and multiple cellulose acetate-binding peptide blocks. The peptides were expressed in *E. coli* as inclusion bodies. Additional amino acid sequences (i.e., peptide tags) were fused to the triblock peptide-based reagent sequence in order to promote inclusion body formation. Acid-labile Asp-Pro (DP) sequences were placed between the peptide tag and the triblock peptide-based reagent sequence to facilitate isolation of the triblock peptide-based reagent from the inclusion body peptide tag.

Construction of Production Strains

The sequence of the triblock peptide-based reagent produced is illustrated in Table 7. DNA sequences were designed to encode the peptide-based reagent using favorable codons for *E. coli* expression and to avoid sequence repeats and mRNA secondary structure. The gene was synthesized by DNA 2.0, Inc. (Menlo Park, Calif.) using proprietary software (Gustafsson et al., *Trends in Biotechnol.* 22(7):346-355 (2004)). The DNA sequence encoding the amino acid sequence was followed by two termination codons and a recognition site for endonuclease AscI. The GS amino acid sequence at the N-terminus was encoded by a recognition site for endonuclease BamHI (GGA/TCC). The C-terminus was designed to include a His-tag.

TABLE 6

Peptide ELISA Results on Cellulose Acetate-Coated Pigment-Binding Activities

| Phage ID | Amino Acid Sequence (SEQ ID NO.) | O.D. at 405 nm | SEM |
| --- | --- | --- | --- |
| No peptide | none | 0.066 | 0.003 |
| CA-1 | ATTPPSGKAAAHSAARQKGN-K-biotin-NH2 (SEQ ID NO: 64) | 0.269 | 0.017 |
| CA-2 | DTIHPNKMKSPSSPL-K-biotin-NH2 (SEQ ID NO: 65) | 0.207 | 0.013 |
| CA-3 | NGNNHTDIPNRSSYTGGSFA-K-biotin-NH2 (SEQ ID NO: 66) | 0.279 | 0.03 |
| CA-4 | SDETGPQIPHRRPTW-K-biotin-NH2 (SEQ ID NO: 67) | 0.141 | 0 |

TABLE 7

Peptide Sequence of Peptide-Based Reagent

| Peptide Reagent | Peptide Sequence | SEQ ID NO: |
|---|---|---|
| DE020 | PHMASMTGGQQMGS (Spacer)-YSETPNDQKPNPHYKVSGTK (tooth-binding peptide)- GPEEAAKKEEAAKKPA (spacer)- YSETPNDQKPNPHYKVSGTK (tooth-binding peptide)- GSGGGGSGSGGGS (spacer)- VRPNLHRKAKAKPDHKQSENRKVPFYSHG SSG (cellulose acetate-binding peptide)- GGG (spacer)- VRPNLHRKAKAKPDHKQSENRKVPFYSHG SSG (cellulose acetate-binding peptide)- GGHHHHHH (spacer/His-tag) | 116 |

The genes were assembled from synthetic oligonucleotides and cloned into a standard plasmid cloning vector by DNA 2.0, Inc. The sequences were then verified by DNA sequencing by DNA 2.0, Inc.

The synthetic gene was excised from the cloning vector with the endonuclease restriction enzymes BamHI and AscI and ligated into an expression vector using standard recombinant DNA methods. The vector pKSI(C4)E-HC77643 (SEQ ID NO: 117) (U.S. provisional patent application No. 60/951,993) was used to express the gene encoding the peptide-based reagent.

The DNA sequence encoding the peptide-based reagent (Table 7) was inserted into pKSI(C4)E-HC77643 by substituting the sequence in the vector between the BamHI and AscI sites. Plasmid DNA containing the peptide encoding sequence and vector DNA was digested with restriction enzymes BamHI and AscI, then the peptide-encoding sequence and vector DNA were mixed and ligated by phage T4 DNA ligase using standard DNA cloning procedures, which are well known to those skilled in the art. The correct construct was identified by restriction analysis and was verified by DNA sequencing.

The coding sequence was operably-linked to the bacteriophage T7 gene 10 promoter and was expressed as a fusion protein, fused with the variant KSI solubility tag.

To test the expression of the peptide-based reagent, the expression plasmid was transformed into the BL21-AI *E. coli* strain (Invitrogen, catalog no. C6070-03). To produce the recombinant peptide, 50 mL of LB-ampicillin broth (10 g/L bacto-tryptone, 5 g/L bacto-yeast extract, 10 g/L NaCl, 100 mg/L ampicillin, pH 7.0) was inoculated with the transformed bacteria and the culture was shaken at 37° C. until the $OD_{600}$ reached 0.6. The expression was induced by adding 0.5 mL of 20 wt % L-arabinose to the culture and shaking was continued for another 4 h.

Growth Conditions

The BL21-AI *E. coli* cells containing the expression plasmid encoding the peptide-based reagent was grown for 20 hours at 37° C. with agitation (200 rpm) in 2.8-L Fernbach flasks containing 1-L of modified ZYP-5052 auto-induction media (Studier, F. William, *Protein Expression and Purification* (2005) 41 L207-234). The media composition per liter was as follows: 10 g/L Tryptone, 5 g/L Yeast Extract, 5 g/L NaCl, 50 mM $Na_2HPO_4$, 50 mM $KH_2PO_4$, 25 mM $(NH_4)_2SO_4$, 3 mM $MgSO_4$, 0.75% glycerol, 0.075% glucose and 0.05% L-arabinose (inducer for BL21 AI T7 system). Under these conditions about 20 g/L wet weight of cells were obtained per liter.

Inclusion Body Isolation

The entire process was performed in one 500-mL bottle. Cells were separated from the growth media by centrifugation and washed with 200-mL (10 g cell paste/100-mL buffer) 20 mM Tris buffer and 10 mM EDTA at pH 8.0. The cell paste was resuspended in 200-mL of 20 mM Tris buffer and 10 mM EDTA at pH 8.0 with added lysozyme (5 mg/200 mL) and taken through at lease one freeze-thaw cycles to facilitate lysis. Lysis was completed by sonication and the inclusion body paste was recovered by centrifugation (9000 RCF 20 minutes at 4° C.). Each additional wash step included resuspension of the inclusion body paste, followed by sonication and centrifugation (9000 RCF 20 minutes at 4° C.). Wash steps included a high pH wash (50 mM Tris HCL pH 9.0) followed by additional washes with 20 mM Tris-HCl pH 8.0. Typically 5 g/L inclusion body paste was recovered.

Acid Cleavage

The recovered inclusion body paste was resuspended in 100 mL of pure water and the pH of the mixture adjusted to 2.2 using HCl. The acidified suspension was heated to 70° C. for 14 hours with agitation to complete cleavage of the DP site separating the fusion peptide from the product peptide.

Oxidative Cross-Linking to Separate the IBT from the Peptide of Interest

The product was cooled to ~5° C. then the pH neutralized to 5.3 using NaOH and cooled for an additional 1 hour at ~5° C. to facilitate precipitation of cysteine cross-linked KSI (C4)E tag. The mixture was then centrifuged at 10000 RCF for 30 minutes at 4° C. The pellet contained the inclusion body fusion partner KSI (C4)E.

Results after Oxidative Cross-Linking:

SDS-PAGE gel analysis of both the precipitate paste and the remaining soluble fraction showed the presence of KSI (C4)E in the insoluble paste with the desired peptide (the peptide-based reagent) remaining in the soluble fraction.

The supernatant contained the peptide of interest (SEQ NO: 116) as confirmed by HPLC analysis. Further analysis of the isolated peptide by LCMS confirmed the absence of contaminating KSI fragments seen with the KSI (C4) version which contains 5 potential internal acid cleavable "D" sequence and 1 preferred acid cleavage site (Asp-Pro).

Example 9

Prophetic

Production of a Peptide-Based Reagent in a 6-L Fermentation

The purpose of this Example is to describe how to produce a peptide-based reagent in a 6-L batch fermentation.

The recombinant *E. coli* strain comprising the expression vector encoding at least one of the present peptide-based reagents is grown in a 6-L fermentation, which is run in batch mode initially, and then in fed-batch mode. The composition of the fermentation medium is given in Table 8. The pH of the fermentation medium is maintained as 6.7. The fermentation medium is sterilized by autoclaving, after which the following sterilized components are added: thiamine hydrochloride (4.5 mg/L), glucose (22.1 g/L), trace elements, see Table 9 (10 mL/L), ampicillin (100 mg/L), and inoculum (seed) (125 mL). The pH is adjusted as needed using ammonium hydroxide (20 vol %) or phosphoric acid (20 vol %). The added components are sterilized either by autoclaving or filtration.

TABLE 8

Composition of Fermentation Medium

| Component | Concentration |
| --- | --- |
| KH$_2$PO$_4$ | 9 g/L |
| (NH$_4$)$_2$HPO$_4$ | 4 g/L |
| MgSO$_4$•7H$_2$O | 1.2 g/L |
| Citric Acid | 1.7 g/L |
| Yeast extract | 5.0 g/L |
| Mazu DF 204 Antifoam | 0.1 mL/L |

TABLE 9

Trace Elements

| Component | Concentration, mg/L |
| --- | --- |
| EDTA | 840 |
| CoCl$_2$•H$_2$O | 250 |
| MnCl$_2$•4H$_2$O | 1500 |
| CuCl$_2$•2H$_2$O | 150 |
| H$_3$BO$_3$ | 300 |
| Na$_2$MoO$_4$•2H$_2$O | 250 |
| Zn(CH$_3$COO)$_2$•H$_2$O | 1300 |
| Ferric citrate | 10000 |

The operating conditions that can be used for the fermentations are summarized in Table 10. The initial concentration of glucose is around 22.1 g/L. When the initial residual glucose is depleted, a pre-scheduled, exponential glucose feed is initiated starting the fed-batch phase of the fermentation run. The glucose feed (see Tables 11 and 12) contains 500 g/L of glucose and is supplemented with 5 g/L of yeast extract. The components of the feed medium are sterilized either by autoclaving or filtration. The goal is to sustain a specific growth rate of 0.13 h$^{-1}$, assuming a yield coefficient (biomass to glucose) of 0.25 g/g, and to maintain the acetic acid levels in the fermentation vessel at very low values (i.e., less than 0.2 g/L). The glucose feed is continued until the end of the run. Induction is initiated with a bolus of 2 g/L of L-arabinose at the selected time (i.e., 15 h of elapsed fermentation time). A bolus to deliver 5 g of yeast extract per liter of fermentation broth is added to the fermentation vessel at the following times: 1 h prior to induction, at induction time, and 1 h after induction time. The fermentation run is terminated after about 20 h of elapsed fermentation time, and about 5 h after the induction time.

TABLE 10

Fermentation Operating Conditions

| Condition | Initial | Minimum | Maximum |
| --- | --- | --- | --- |
| Stirring | 220 rpm | 220 rpm | 1200 rpm |
| Air Flow | 3 SLPM | 3 SLPM | 30 SLPM |
| Temperature | 37° C. | 37° C. | 37° C. |
| pH | 6.7 | 6.7 | 6.7 |
| Pressure | 0.500 atm | 0.500 atm | 0.500 atm |
|  | (50.7 kPa) | (50.7 kPa) | (50.7 kPa) |
| Dissolved O$_2$* | 20% | 20% | 20% |

*Cascade stirrer, then air flow.

TABLE 11

Composition of Feed Medium

| Component | Concentration |
| --- | --- |
| MgSO$_4$•7H$_2$O | 2.0 g/L |
| Glucose | 500 g/L |
| Ampicillin | 150 mg/L |
| (NH$_4$)$_2$HPO$_4$ | 4 g/L |
| KH$_2$PO$_4$ | 9 g/L |
| Yeast extract | 5.0 g/L |
| Trace Elements - Feed (Table 5) | 10 mL/L |

TABLE 12

Trace Elements - Feed

| Component | Concentration, mg/L |
| --- | --- |
| EDTA | 1300 |
| CoCl$_2$•H$_2$O | 400 |
| MnCl$_2$•4H$_2$O | 2350 |
| CuCl$_2$•2H$_2$O | 250 |
| H$_3$BO$_3$ | 500 |
| Na$_2$MoO$_4$•2H$_2$O | 400 |
| Zn(CH$_3$COO)$_2$•H$_2$O | 1600 |
| Ferric citrate | 4000 |

Isolation and Purification of Peptide:

After completion of the fermentation run, the entire fermentation broth is passed three times through an APV model 2000 Gaulin type homogenizer at 12,000 psi (82,700 kPa). The broth is cooled to below 5° C. prior to each homogenization. The homogenized broth is immediately processed through a Westfalia WHISPERFUGE™ (Westfalia Separator Inc., Northvale, N.J.) stacked disc centrifuge at 700 mL/min and 12,000 RCF to separate inclusion bodies from suspended cell debris and dissolved impurities. The recovered paste is re-suspended at 15 g/L (dry basis) in water and the pH is adjusted to a value between 8.0 and 10.0 using Na$_2$CO$_3$/NaOH buffer. The pH is chosen to help remove cell debris from the inclusion bodies without dissolving the inclusion body proteins. The suspension is passed through the APV 2000 Gaulin type homogenizer at 12,000 psi (82,700 kPa) for a single pass to provide rigorous mixing. The homogenized high pH suspension is immediately processed in a Westfalia WHISPERFUGE™ stacked disc centrifuge at 700 mL/min and 12,000 RCF to separate the washed inclusion bodies from suspended cell debris and dissolved impurities. The recovered paste is resuspended at 15 gm/L (dry basis) in pure water. The suspension is passed through the APV 2000 Gaulin type homogenizer at 12,000 psi (82,700 kPa) for a single pass to provide rigorous washing. The homogenized suspension is immediately processed in a Westfalia WHISPERFUGE™ stacked disc centrifuge at 700 mL/min and 12,000 RCF to separate the washed inclusion bodies from residual suspended cell debris and NaOH.

The recovered paste is resuspended in pure water at 25 g/L (dry basis) and the pH of the mixture is adjusted to 2.2 using HCl. The acidified suspension is heated to 70° C. for 5 to 14 h to complete cleavage of the DP site separating the fusion peptide from the product peptide without damaging the target peptide. The product slurry is adjusted to pH 5.1 (note: the pH used here may vary depending on the solubility of the peptide being recovered) using NaOH and then is cooled to 5° C. and held for 12 h. The mixture is centrifuged at 9000 RCF for 30 min and the supernatant is decanted. The supernatant is then filtered with a 0.45 μm membrane. For some low solubility peptides, multiple washes of the pellet may be required to increase peptide recovery.

The filtered product is collected and concentrated by vacuum evaporation by a factor of 2:1 before lyophilization. Spectrophotometric detection at 220 and 278 nm is used to monitor and track elution of the product peptide.

Example 10

Preparation of Cellulose Acetate-Coated Whitening Agent

Rutile titanium dioxide (DuPont, Wilmington, Del.) was first coated with silica by a process described in Iler in U.S. Pat. No. 2,885,366 with a 3% silica loading. Approximately 20 g of the silica-coated pigment was combined with 10 g of cellulose acetate (Eastman Chemical Company, Kingsport, Tenn.; catalog #CA398-10) and 90 g acetone in a stainless steel blender and mixed for 50 minutes. The mixture was transferred to an Erlenmeyer flask and stirred with slow addition of 60 mL petroleum ether. The mixture was filtered and the solid was washed with petroleum ether and dried in a vacuum oven at 60° C., yielding 20.4 g of a white solid with a particle size (average equivalent diameter, d50) of 1.2 microns.

Approximately 10 g of the cellulose acetate-coated titanium dioxide was combined with 25 g 0.5 mm glass beads and 40 g water in a SPEEDMIXER™ DAC150 FVZ-K (FlackTek Inc., Landrum, S.C.). The mixture was processed for a total of 20 minutes. Following mixing, the solution was filtered to remove the glass beads. The resulting pigment dispersion was an opaque white solution with a particle size (average equivalent diameter, d50) of 435 nm.

Example 11

Tooth Whitening Using a Polymer-Coated White Colorant in Conjunction with a Peptide-Based Reagent The purpose of this Example was to demonstrate a process for whitening teeth using a polymer-coated white colorant in conjunction with a peptide-based reagent and to compare the results to the whitening obtained with the polymer-coated white colorant alone. The peptide-based reagent comprising multiple tooth-binding peptides, spacers, and cellulose acetate-binding peptide sequences was prepared as described in Example 8.

The cellulose acetate-coated titanium dioxide was prepared as described in Example 10. The peptide-based reagent described in Example 8 (SEQ ID NO:116) was used. The peptide-based reagent was diluted with 25 mM Tris-HCl buffer including 150 mM NaCl at pH 7.5 to give a final concentration of 5 µM. The cellulose acetate-coated titanium dioxide dispersion described in Example 10 was further diluted from 20% solids to 0.25% solids in 25 mM Tris-HCl buffer at pH 7.5.

Tooth Substrates:

Bovine Teeth (SE Dental, Baton Rouge, La.) were used as model substrate to test with the engineered peptide-based reagent designed to bind to tooth enamel (SEQ ID NO:116). The teeth were prepared by cleaning in detergent and then disinfecting in 70% Ethanol prior to use. Each clean tooth was measured for color using an X-RITE® SP64 Spectrometer to collect a reflectance spectrum and CIELAB color coordinates, L*, a* and b*. A staining solution was made with 100 mL of boiling water exposed to 1 Lipton tea bag for 5 minutes. After the solution cooled to room temperature, each tooth was allowed to incubate in the staining solution for approximately 3 days. The teeth were removed and rinsed with water and dried. Color measurement was obtained for each tooth.

Tooth Whitening

The stained bovine enamel substrates were exposed to either the 5 µM solution of peptide or as a control, the buffer used to make the peptide solution. This exposure was for 30 minutes with gentle agitation in a vortex mixer. Following peptide binding, the teeth were removed and rinsed in buffer and placed in a 0.25% solution of cellulose acetate coated titanium dioxide for 30 minutes. The teeth were removed, rinsed in buffer, blotted dry and measured for color using the X-RITE® spectrometer. The teeth were placed back in the same pigment solutions for an additional 2.5 hr and removed, rinsed and measured again. Results are reported in Table 13.

Measurement of Color Intensity

The color intensity at each step mentioned above (e.g., to determine the change in tooth whitening) was measured using a X-RITE® SP64™ Sphere Spectrophotometer (X-Rite, Inc., Grandville, Mich.), by placing the front of the bovine tooth (treated or control) sample into a sample holder and calculating L*, a* and b* parameters representing the photometer response using a standard D65 illuminant. An initial baseline values of L*, a* and b* were measured prior to peptide treatment for the tea-stained bovine samples. All measurements are the average of three individual determinations. Delta E values are calculated using equation 1 below:

$$\text{Delta } E = ((L^*_1 - L^*_2)^2 + (a_1 - a_2)^2 + (b_1 - b_2)^2)^{1/2} \qquad (1)$$

where L*=the lightness variable and a* and b* are the chromaticity coordinates of CIELAB colorspace as defined by the International Commission of Illumination (CIE) (Minolta, *Precise Color Communication—Color Control From Feeling to Instrumentation*, Minolta Camera Co., 1996). Larger Delta E value is indicative of an increase in whiteness. In one embodiment, a larger Delta E for the treatment group (peptide-based reagent+polymer coated white colorant) versus the Delta E of the peptide-free control is used to determine the relative increase in whiteness.

In another aspect, the measurement of the whiteness of teeth may also be reported as a whiteness index wherein an increase in the whiteness after treatment with the present compositions is indicative of increased whitening. The whiteness index (WI) is defined by the International Commission on Illumination (CIE) and described in ASTM method E313-05 and calculated for D65/10 incident light as:

$$WI = Y + 800 * (0.3138 - x) + 1700 * (0.3310 - y)$$

where Y, x, and y are the luminance factor and the chromaticity coordinates respectively of the enamel substrate.

TABLE 13

Whitening of Bovine Enamel using Engineered Peptide and Cellulose Acetate-coated $TiO_2$.

|  | Control | Treated |
|---|---|---|
| Tea stain 3 days | | |
| L* | 71.6364 | 67.0271 |
| a* | 2.93059 | 3.96396 |
| b* | 20.7223 | 22.7952 |
| ΔE | 0.00 | 0.00 |
| Peptide/buffer (30 min) + CA-$TiO_2$ (30 min) | | |
| L* | 73.336 | 71.1068 |
| a* | 1.69143 | 1.63501 |
| b* | 18.2412 | 18.0418 |
| ΔE | 3.25 | 6.68 |

TABLE 13-continued

Whitening of Bovine Enamel using Engineered
Peptide and Cellulose Acetate-coated $TiO_2$.

| | Control | Treated |
|---|---|---|
| | $CA-TiO_2$ (2.5 hr) | |
| L* | 73.7424 | 73.9558 |
| a* | 1.62671 | 1.49585 |
| b* | 17.8343 | 18.0851 |
| ΔE | 3.80 | 8.73 |

Example 12

Selection of Tooth (Pellicle)-Binding Peptides Using Biopanning

The purpose of this Example was to identify phage peptides that bind to tooth pellicle formed in vivo on bovine enamel.

Bovine enamel incisors were obtained from SE Dental (Baton Rouge, La.). The teeth were cut to approximately 5 mm squares and polished to remove surface debris. Enamel blocks were sterilized and sewn into intra-oral retainers in order to expose the enamel surface to the human oral environment. A retainer with 2 to 4 enamel blocks was worn in the human mouth for 30 min to form a pellicle layer on the enamel. After incubation, the enamel blocks were removed from the retainer, rinsed with water and embedded in a well plate contained molding material so as to only expose the pellicle-coated enamel surface in the well. The plate was sterilized with UV light for 10 minutes.

The substrates were then incubated in blocking buffer for 1 hour at room temperature (1 mg/mL bovine serum albumin in phosphate buffered saline pH 7.2 (Pierce BUPH™ #28372) with 0.1% TWEEN® 20 (PBST), followed by 2 washes with PBST. Libraries of phage containing random peptide inserts ($10^{11}$ pfu) from 15 to 20 amino acids were added to each well. After 30 minutes of incubation at 37° C. and shaking at 50 rpm, unbound phage were removed by aspirating the liquid out of each well followed by 6 washes with 1.0 mL PBST.

The enamel blocks were then transferred to clean tubes and 1 mL of elution buffer consisting of 1 mg/mL BSA in 0.2 M glycine-HCl, pH 2.2, was added to each well and incubated for 10 min at room temperature to elute the bound phages. Then, 167 μL of neutralization buffer consisting of 1 M Tris-HCl, pH 9.1, was added to each well. The phage particles, which were in the elution buffer as well as on the enamel blocks, were amplified by incubating with 20 mL diluted *E. coli* ER2738 cells, from an overnight culture diluted 1:100 in LB medium, at 37° C. for 4.5 h. After this time, the cell culture was centrifuged for 2 min and the upper 15 mL of the supernatant was transferred to a fresh tube, 2.5 mL of PEG/NaCl (20% polyethylene glycol-800, 2.5 M sodium chloride) was added, and the phage were allowed to precipitate overnight at 4° C. The precipitate was collected by centrifugation at 10,000×g at 4° C. and the resulting pellet was resuspended in 1 mL of PBS. This was the first round of amplified stock. The amplified first round phage stock was then tittered according to the standard protocol. For subsequent rounds of biopanning, more than $2 \times 10^{11}$ pfu of phage stock from the previous round was used. Each additional round after the first also included additional washes with 0.5% sodium lauryl sulfate in water (Spectrum), two washes with carbonate buffer pH 9.4 (Pierce BUPH™ Carbonate-Bicarbonate Buffer #28382) and 2 washes with 50 mM phosphate buffer, pH 2.5.

The biopanning process was repeated an additional 3 more rounds under the same conditions as described above with an additional exposure of the phage stock to oral soft tissue. The phage stock amplified from the $2^{nd}$ round was exposed first to EPIORAL™ and EPIGINGIVAL™ soft tissues (MatTek Corp, Ashland, Mass.) by incubating 8 μL of the $2^{nd}$ round phage stock+42 μL of blocking buffer (PBST+1 mg/mL BSA) for 60 min. The solution was removed from the tissue and an additional 50 μL of PBS was incubated with the tissue for 30 min. The solutions were combined and used in additional rounds of biopanning as described above.

After the 3rd round of biopanning and each subsequent round, 95 random single phage plaques were isolated and the single stranded phage genomic DNA was prepared using the Illustra TempliPhi 500 Amplification Kit (GE Healthcare, Piscataway, N.J.) and sequenced at the DuPont Sequencing Facility using −96 gIII sequencing primer (5'-CCCTCAT-AGTTAGCGTAACG-3'; SEQ ID NO: 68). The displayed peptide was located immediately after the signal peptide of gene III. Based on the peptide sequences, 31 phage candidates were identified for further pellicle binding analysis (Table 14).

TABLE 14

Tooth-binding Peptides Identified from Biopanning on 30 min in vivo Pellicle

| Peptide ID | Amino Acid Sequence | SEQ ID NO |
|---|---|---|
| DenP 01 | NGNNHTDIPNRSSYTGGSFA | 119 |
| DenP 02 | TMTNHVYNSYTEKHSSTHRS | 120 |
| DenP 03 | TTYHYKNIYQESYQQRNPAV | 121 |
| DenP 04 | VEPATKNMREARSSTQMRRI | 122 |
| DenP 05 | YLLPKDQTTAPQVTPIVQHK | 123 |
| DenP 06 | ASNLDSTFTAINTPACCT | 124 |
| DenP 07 | EFPYYNDNPPNPERHTLR | 125 |
| DenP 08 | GMPTRYYHNTPPHLTPKF | 126 |
| DenP 09 | HKNAIQPVNDATTLDTTM | 127 |
| DenP 10 | AVVPADLNDHANHLS | 128 |
| DenP 11 | DLGTFPNRTLKMAAH | 129 |
| DenP 12 | FDGIGLGTATRHQNR | 130 |
| DenP 13 | QAAQVHMMQHSRPTT | 131 |
| DenP 14 | SEARARTFNDHTTPMPII | 132 |
| DenP 15 | ELDHDSRHYMNGLQRKVT | 133 |
| DenP 16 | GPQHVLMQDTHQGYAFDN | 134 |
| DenP 17 | TTGSSSQADTSASMSIVPAH | 135 |
| DenP 18 | KAPIANMLQPHSYQYSVA | 136 |
| DenP 19 | TYQGVPSWPAVIDDAIRR | 137 |
| DenP 20 | VNPNWVETQALHQPPGNT | 138 |
| DenP 21 | DHNNRQHAVEVRENKTHTAR | 139 |
| DenP 22 | IYPNESMSTSNVRGPYHP | 140 |
| DenP 23 | HDPNHLTHQARTIYRNANHT | 141 |

TABLE 14-continued

Tooth-binding Peptides Identified from Biopanning on 30 min in vivo Pellicle

| Peptide ID | Amino Acid Sequence | SEQ ID NO |
|---|---|---|
| DenP 24 | SNATMYNIQSHSHHQ | 142 |
| DenP 25 | ANELSTYAQTNPGSG | 143 |
| DenP 26 | DTIHPNKMKSPSSPL | 144 |
| DenP 28 | APPTYQTASYPHNLPSKRKM | 145 |
| DenP 29 | QVPDYLSPTHQKKAFLEIPT | 146 |
| DenP 30 | TNDLHANPFTGTYIAPDPTS | 147 |
| DenP 32 | HKNENIMQYNVNDRWHITPA | 148 |
| DenP 33 | IDGPHHSPVHRYHTPSIT | 149 |

Example 13

Characterization of Tooth (Pellicle)-Binding Candidates on Pellicle Surface

A total of 29 selected phage candidates from Table 14 were used in phage ELISA Experiment to determine binding affinity and coverage of each phage on pellicle substrates. Purified phage lysates were used for binding to pellicle coated bovine enamel using an anti-M13 phage antibody conjugated to horseradish-peroxidase, followed by the addition of chromogenic agent TMB, obtained from Pierce Biotechnology (Rockford, Ill.). The plates were read at $A_{450nm}$.

Enamel substrates were cut to approximately 7 mm squares and mounted on wax mounting for incubation in the mouth for 30 min to form a pellicle-coated surface. The pellicle-coated enamel substrates were removed from the wax backing and placed in well plates with the pellicle surface exposed as in Example 12. Each pellicle-coated substrate was incubated for 1.5 h at room temperature with 1 mL of blocking buffer, consisting of 1 mg/mL BSA in PBST (Pierce BUPH™ #28372 with 0.1% TWEEN®20). The blocking buffer was removed by aspirating the liquid out of each well. The tube was rinsed 2 times with wash buffer consisting of PBST. The wells were filled with 1 mL of $10^{11}$ pfu purified phage stock which was prepared by diluting in blocking buffer. The samples were incubated for 30 min with slow shaking at 37° C. The non-binding phage was removed by washing 5 times with PBST. Then, 500 µL of horseradish peroxidase/anti-M13 antibody conjugate (Amersham USA, Piscataway, N.J.), diluted 1:500 in the blocking buffer, was added and incubated for 1 h at room temperature (~22° C.). The conjugate solution was removed and was washed 3 times with PBST. Each enamel substrate was removed from the well and washed again in a 15-mL test tube with 5 mL of PBST. Each enamel substrate was then mounted in a clean well plate with only the enamel surface exposed. A 1:1 solution of TMB substrate and $H_2O_2$ (200 µL), obtained from Pierce Biotechnology (Rockford, Ill.) was added to each well and the color was allowed to develop for between 5 to 30 min, typically for 10 min, at room temperature (approximately 22° C.). Then, stop solution (100 µL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values, are given in Table 15. The analysis of all 30 pellicle-binding candidates was completed over the course of two days and the results were normalized to an internal control.

TABLE 15

Phage ELISA Results for Pellicle-binding Peptide Candidates Obtained from Biopanning

| Peptide ID | Amino Acid Sequences | SEQ ID NO: | O.D. at 450 nm (normalized) |
|---|---|---|---|
| Control | IPWWNIRAPLNAGGG | 150 | 1.000 |
| DenP 01 | NGNNHTDIPNRSSYTGGSFA | 119 | 1.002 |
| DenP 02 | TMTNHVYNSYTEKHSSTHRS | 120 | 1.951 |
| DenP 03 | TTYHYKNIYQESYQQRNPAV | 121 | 2.495 |
| DenP 04 | VEPATKNMREARSSTQMRRI | 122 | 1.421 |
| DenP 05 | YLLPKDQTTAPQVTPIVQHK | 123 | 1.087 |
| DenP 07 | EFPYYNDNPPNPERHTLR | 125 | 1.500 |
| DenP 08 | GMPTRYYHNTPPHLTPKF | 126 | 1.182 |
| DenP 09 | HKNAIQPVNDATTLDTTM | 127 | 1.364 |
| DenP 10 | AVVPADLNDHANHLS | 128 | 1.619 |
| DenP 11 | DLGTFPNRTLKMAAH | 129 | 1.663 |
| DenP 12 | FDGIGLGTATRHQNR | 130 | 2.079 |
| DenP 13 | QAAQVHMMQHSRPTT | 131 | 0.845 |
| DenP 14 | SEARARTFNDHTTPMPII | 132 | 2.498 |
| DenP 15 | ELDHDSRHYMNGLQRKVT | 133 | 1.112 |
| DenP 16 | GPQHVLMQDTHQGYAFDN | 134 | 2.190 |
| DenP 17 | TTGSSSQADTSASMSIVPAH | 135 | 0.971 |
| DenP 18 | KAPIANMLQPHSYQYSVA | 136 | 1.143 |
| DenP 19 | TYQGVPSWPAVIDDAIRR | 137 | 1.052 |
| DenP 20 | VNPNWVETQALHQPPGNT | 138 | 1.298 |
| DenP 21 | DHNNRQHAVEVRENKTHTAR | 139 | 0.728 |
| DenP 22 | IYPNESMSTSNVRGPYHP | 140 | 1.420 |
| DenP 23 | HDPNHLTHQARTIYRNANHT | 141 | 1.236 |
| DenP 24 | SNATMYNIQSHSHHQ | 142 | 0.979 |
| DenP 25 | ANELSTYAQTNPGSG | 143 | 0.909 |
| DenP 26 | DTIHPNKMKSPSSPL | 144 | 1.039 |
| DenP 28 | APPTYQTASYPHNLPSKRKM | 145 | 1.203 |
| DenP 29 | QVPDYLSPTHQKKAFLEIPT | 146 | 0.976 |
| DenP 30 | TNDLHANPFTGTYIAPDPTS | 147 | 1.082 |
| DenP 32 | HKNENIMQYNVNDRWHITPA | 148 | 1.441 |

Example 14

Characterization of Tooth Pellicle-Binding Candidates on Pellicle Surface

The purpose of this example was to confirm the binding of peptide compositions on pellicle surfaces using synthetically produced peptides.

A total of 20 synthetic peptides were manufactured using sequences obtained from Table 14. Peptides were obtained from Synbiosci (Livermore, Calif.) and included an additional SSRP sequence (SEQ ID NO: 151) at the N-terminus and biotin labeled lysine at the C-terminus.

Enamel substrates were cut to approx. 7 mm squares and mounted on wax mounting for incubation in the mouth for 30 min to form a pellicle coated surface. The pellicle-coated enamel substrates were removed from the wax backing and placed in well plates with the pellicle surface exposed as in Example 1. Each pellicle-coated substrate was incubated for 1 h at room temperature (~22° C.) with 1 mL of blocking buffer, consisting of 1 mg/mL BSA in PBST (Pierce BupH™ #28372 with 0.1% TWEEN® 20). The blocking buffer was removed by aspirating the liquid out of each well. The tube was rinsed 2 times with wash buffer consisting of PBST. The wells were filled with 500 µL of 20 µM peptide solution which was prepared by diluting in blocking buffer. The samples were incubated for 30 min with slow shaking at 37° C. The non-binding peptide was removed by washing 6 times with PBST. Then, 500 µL of horseradish peroxidase/streptavidin conjugate (Pierce #22127), diluted 1:2000 in PBST, was added and incubated for 1 h at room temperature. The conjugate solution was removed and was washed 4 times with PBST.

Each enamel substrate was removed from the well and washed again in a 15-mL test tube with 10 mL of PBST. Each enamel substrate was then mounted in a clean well plate with only the enamel surface exposed. A 1:1 solution of TMB substrate and $H_2O_2$ (200 µL), obtained from Pierce Biotechnology (Rockford, Ill.) was added to each well and the color was allowed to develop for between 10 to 20 min, typically for 15 min, at room temperature (~22° C.). Then, 100 µL of solution from each well was transferred to a 96-well reading plate containing stop solution (100 µL of 2 M $H_2SO_4$) in each well. The $A_{450}$ was measured using a microplate spectrophotometer (Molecular Devices, Sunnyvale, Calif.). The resulting absorbance values,) are given in Table 16. The analysis of 20 pellicle-binding candidates was completed over the course of two days and the results were normalized to the best binding candidate from day 1 (DenP03). Each sequence was tested with three replicate enamel coated pellicle substrates.

TABLE 16

Synthetic Peptide ELISA Results for Pellicle-binding Candidates Obtained from Biopanning.

| Pellicle binding peptide ID | Amino Acid Sequence | O.D. at 450 nm (normalized) | SEQ ID NO |
|---|---|---|---|
| No peptide | — | −0.001 | — |
| DenP1-A | SSRPNGNNHTDIPNRSSYTGGSFAK(biotin) | 0.154 | 152 |
| DenP2-A | SSRPTMTNHVYNSYTEKHSSTHRSK(biotin) | 0.273 | 153 |
| DenP3-A | SSRPTTYHYKNIYQESYQQRNPAVK(biotin) | 1.000 | 154 |
| DenP4-A | SSRPVEPATKNMREARSSTQMRRIK(biotin) | 0.803 | 155 |
| DenP5-A | SSRPYLLPKDQTTAPQVTPIVQHKK(biotin) | 0.462 | 156 |
| DenP7-A | SSRPEFPYYNDNPPNPERHTLRK(biotin) | 0.356 | 157 |
| DenP11-A | SSRPDLGTFPNRTLKMAAHK(biotin) | 0.454 | 158 |
| DenP12-A | SSRPFDGIGLGTATRHQNRK(biotin) | 0.475 | 159 |
| DenP13-A | SSRPQAAQVHMMQHSRPTTK(biotin) | 0.699 | 160 |
| DenP14-A | SSRPSEARARTFNDHTTPMPIIK(biotin) | 0.269 | 161 |
| DenP15-A | SSRPELDHDSRHYMNGLQRKVTK(biotin) | 0.460 | 162 |
| DenP16-A | SSRPGPQHVLMQDTHQGYAFDNK(biotin) | 0.309 | 163 |
| DenP17-A | SSRPTTGSSSQADTSASMSIVPAHK(biotin) | 0.143 | 164 |
| DenP19-A | SSRPTYQGVPSWPAVIDDAIRRK(biotin) | 0.712 | 165 |
| DenP20-A | SSRPVNPNWVETQALHQPPGNTK(biotin) | 0.590 | 166 |
| DenP22-A | SSRPIYPNESMSTSNVRGPYHPK(biotin) | 0.354 | 167 |
| DenP23-A | SSRPHDPNHLTHQARTIYRNANHTK(biotin) | 0.850 | 168 |
| DenP28-A | SSRPAPPTYQTASYPHNLPSKRKMK(biotin) | 0.811 | 169 |

TABLE 16-continued

Synthetic Peptide ELISA Results for Pellicle-binding
Candidates Obtained from Biopanning.

| Pellicle binding peptide ID | Amino Acid Sequence | O.D. at 450 nm (normalized) | SEQ ID NO |
|---|---|---|---|
| DenP29-A | SSRPQVPDYLSPTHQKKAFLEIPTK(biotin) | 0.468 | 170 |
| DenP32-A | SSRPHKNENIMQYNVNDRWHITPAK(biotin) | 1.135 | 171 |

Example 15

Determination of the Peptide Binding Affinity on Pellicle Surface

The purpose of this Example was to determine the affinity and specificity of the pellicle-binding peptides and peptide compositions comprising the pellicle-binding peptides identified in Example 14, measured as $MB_{50}$ values, using an ELISA assay.

Pellicle-binding peptides, DenP3-A and DenP32-A as described in Table 16, were synthesized using standard solid phage synthesis method and were biotinylated at the C-terminus lysine residue of binding sequence for detection purposes.

Enamel substrates were cut to approx. 4 mm squares and mounted on wax mounting for incubation in the mouth for 30 min to form a pellicle coated surface. The pellicle-coated enamel substrates were removed from the wax backing and placed in well plates with the pellicle surface exposed as in Example 1. Each pellicle-coated substrate was incubated for 1 h at room temperature (2° C.) with 1 mL of blocking buffer, consisting of 1 mg/mL BSA in PBST (Pierce BupH™ #28372 with 0.1% TWEEN® 20). The blocking buffer was removed by aspirating the liquid out of each well. The tube was rinsed 2 times with wash buffer consisting of PBST. The wells were filled with 500 μL of peptide solution which was prepared by diluting in blocking buffer across a range of concentrations. The samples were incubated for 2 h with slow shaking at 37° C. The non-binding peptide was removed by washing 6 times with PBST. Then, 500 μL of alkaline phosphatase/streptavidin conjugate (Pierce), diluted 1:2500 in PBST, was added and incubated for 1 h at room temperature. The conjugate solution was removed and was washed 4 times with PBST.

Each enamel substrate was removed from the well and washed again in a 15-mL test tube with 10 mL of PBST. Each enamel substrate was then mounted in a clean well plate with only the enamel surface exposed. 150 μL of Methyl umbelliferone 4-phosphate (4-MUP) substrate (Sigma) was added to each well and incubated at room temperature for 30 min protected from ambient light. Then, 100 uL of solution from each well was transferred to a 96-well reading plate. Fluorescence was read using a microplate spectrophotometer (Molecular Devices, Sunnyvale, Calif.). The results were plotted as relative fluorescence units versus the concentration of peptide using GraphPad Prism 4.0 (GraphPad Software, Inc., San Diego, Calif.). The $MB_{50}$ values were calculated from Scatchard plots and are shown Table 17.

TABLE 17

Summar of $MB_{50}$ Values for Pellicle-Binding Peptides Against Pellicle Surface

| Peptide ID | SEQ ID NO | Sequence | $MB_{50}$ (M) |
|---|---|---|---|
| DenP3-A | 154 | SSRPTTYHYKNIYQESYQQRNPAVK(biotin) | $2.8 \times 10^{-5}$ |
| DenP32-A | 171 | SSRPHKNENIMQYNVNDRWHITPAK(biotin) | $2.5 \times 10^{-5}$ |

Example 16

Selection of Additional Pellicle-Binding Peptides Using Standard Biopanning

The purpose of this Example was to identify phage peptides that bind tooth pellicle created with long term exposure in the mouth using standard phage display biopanning.

Bovine enamel incisors were obtained from SE Dental (Baton Rouge, La.). The teeth were cut to approx. 7 mm squares and polished to remove surface debris. Enamel blocks were sterilized and sewn into intra-oral retainers in order to expose the enamel surface to the human oral environment. A retainer with 4 enamel blocks was worn in a human mouth for approximately 8 hours. The retainer was removed from the subject and each enamel block was manually brushed with toothpaste and a soft bristle brush under water. The retainer was reinserted into the subject's mouth for an additional 1 min. The enamel blocks were removed from the retainer, rinsed with water and embedded in a well plate contained molding material so as to only expose the pellicle coated enamel surface in the well. The plate was sterilized with UV light for 10 minutes.

The substrates were then incubated in blocking buffer for 1 hour at room temperature (1 mg/mL bovine serum albumin in phosphate buffered saline pH 7.2 (Pierce BupH™ #28372) with 0.1% TWEEN® 20 (PBST)), followed by 2 washes with PBST (PBS in 0.1% TWEEN® 20). Libraries of phage containing random peptide inserts ($10^{11}$ pfu) from 16 to 20 amino acids were added to each well. After 30 minutes of incubation at 37° C. and shaking at 50 rpm, unbound phage were removed by aspirating the liquid out of each well followed by 2 washes with 1.0 mL PBST.

The enamel blocks were then transferred to a clean tube and 1 mL of elution buffer consisting of 1 mg/mL BSA in 0.2

M glycine-HCl, pH 2.2, was added to each well and incubated for 10 min to elute the bound phages. Then, 167 µL of neutralization buffer consisting of 1 M Tris-HCl, pH 9.1, was added to each well. The phage particles, which were in the elution buffer as well as on the enamel blocks, were amplified by incubating with 20 mL diluted E. coli ER2738 cells, from an overnight culture diluted 1:100 in LB medium, at 37° C. for 4.5 h. After this time, the cell culture was centrifuged for 2 min and the upper 15 mL of the supernatant was transferred to a fresh tube, 2.5 mL of PEG/NaCl (20% polyethylene glyco-800, 2.5 M sodium chloride) was added, and the phage was allowed to precipitate overnight at 4° C. The precipitate was collected by centrifugation at 10,000×g at 4° C. and the resulting pellet was resuspended in 1 mL of PBS. This was the first round of amplified stock. The amplified first round phage stock was then titered according to the standard protocol. For the $2^{nd}$, $3^{rd}$ $4^{th}$ and $5^{th}$ rounds of biopanning, more than $2 \times 10^{11}$ pfu of phage stock from the previous round was used. In these subsequent rounds, additional washes processes were included after the initial incubation of the phage. These washes included a 0.5% sodium lauryl sulfate in water (Spectrum), two washes with carbonate buffer pH 9.4 (Pierce BupH™ Carbonate-Bicarbonate Buffer #28382) and 2 washes with 50 mM phosphate buffer, pH 2.5 followed by 5 washes with PBST.

After the 3rd round of biopanning and each subsequent round, 95 random single phage plaques were isolated and the single stranded phage genomic DNA was prepared using the Illustra Templiphi 500 Amplification Kit (GE Healthcare, Piscataway, N.J.) and sequenced at the DuPont Sequencing Facility using −96 gIII sequencing primer (5'-CCCTCAT-AGTTAGCGTAACG-3'; SEQ ID NO: 68). The displayed peptide was located immediately after the signal peptide of gene III. Based on the peptide sequences, 23 phage candidates were selected for further pellicle binding analysis. These candidates included 3 sequences previously discovered in panning in Example 12.

TABLE 18

Binding Sequences Identified from Biopanning on Brushed, 8-hour in vivo Pellicle.

| ID | Amino Acid Sequence | SEQ ID NO |
|---|---|---|
| DenP101 | AIEYQHSATTPWTMRTRLPP | 172 |
| DenP102 | EFYPFAEVPPEKSGIGRQVF | 173 |
| DenP103 | GVHQYSRPTVPSYLWTSGQH | 174 |
| DenP104 | GYQPHYVDHTIGWQPMIRPN | 175 |
| DenP105 | QFNQTSHSFMHGTSGYVPGK | 176 |
| DenP106 | SFSWHRGDWELGHQSKTMGM | 177 |
| DenP107 | SMWHDITKRYRNPSEMVSAY | 178 |
| DenP108 | THGNKHQSWTYPSEINHKNY | 179 |
| DenP109 | WHEPHQFSGENTDYSSSMGT | 180 |
| DenP110 | THGNKHQSWTYPSEINHKNY | 181 |
| DenP111 | DGYKLQTSLDWQMWNP | 182 |
| DenP112 | FPSKWYNHHRHITGHV | 183 |
| DenP113 | GGMGALESYRQWNHLA | 184 |
| DenP114 | GINKGQRPPWESWHEN | 185 |

TABLE 18-continued

Binding Sequences Identified from Biopanning on Brushed, 8-hour in vivo Pellicle.

| ID | Amino Acid Sequence | SEQ ID NO |
|---|---|---|
| DenP115 | GYGQYVSQQTWAHSNK | 186 |
| DenP116 | HDHLSWWGQFDRQNLL | 187 |
| DenP117 | MPGHQESIKVQNWNRV | 188 |
| DenP118 | NLHSPWPSHAAHHWST | 189 |
| DenP119 | NQQMKLVPQHWHRAQP | 190 |
| DenP120 | SEKWFNPGPWPKLATQ | 191 |
| DenP11 | DLGTFPNRTLKMAAH | 129 |
| DenP07 | EFPYYNDNPPNPERHTLR | 125 |
| DenP08 | GMPTRYYHNTPPHLTPKF | 126 |

Example 17

Characterization of Tooth Pellicle-Binding Candidates on Pellicle Surface

A total of 18 selected phage candidates were used in a phage ELISA Experiment. Purified phage lysates were used for binding to pellicle-coated bovine enamel using an anti-M13 phage antibody conjugated to horseradish-peroxidase, followed by the addition of chromogenic agent TMB, obtained from Pierce Biotechnology (Rockford, Ill.). The plates were read at $A_{450nm}$.

Enamel substrates were cut to approx. 4 mm squares, cleaned, sterilized and mounted on wax mounting for incubation in the mouth for 30 min to form a pellicle coated surface. The pellicle coated enamel substrates were removed from the wax backing and placed in well plates with the pellicle surface exposed as in Example 1. Each pellicle-coated substrate was incubated for 1 h at room temperature with 0.5 mL of blocking buffer, consisting of 1 mg/mL BSA in PBST pH 7.2 (Pierce BupH™ #28372 with 0.1% TWEEN® 20). The blocking buffer was removed by aspirating the liquid out of each well. The wells were rinsed 2 times with wash buffer consisting of PBST. The wells were filled with 1 mL of $10^{11}$ pfu purified phage stock which was prepared by diluting in blocking buffer. The samples were incubated for 30 min with slow shaking at 37° C. The non-binding phage was removed by washing 5 times with PBST. Then, 500 µL of horseradish peroxidase/anti-M13 antibody conjugate (Amersham USA, Piscataway, N.J.), diluted 1:500 in the blocking buffer, was added and incubated for 45 min at room temperature. The conjugate solution was removed and was washed 5 times with PBST. Each enamel substrate was removed from the well and washed again in a 15-mL test tube with 10 mL of PBST. Each enamel substrate was then mounted in a clean well plate with only the enamel surface exposed. A 1:1 solution of TMB substrate and $H_2O_2$ (200 µL), obtained from Pierce Biotechnology (Rockford, Ill.) was added to each well and the color was allowed to develop for between 5 to 30 min, typically for 10 min, at room temperature. Then, stop solution (100 µL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values, are given in Table 8. The analysis of all 18 pellicle binding candidates was completed over the course of two days and the results were normalized to the result of DenP3 which was measured on both days.

TABLE 19

Phage ELISA Results for Pellicle-binding Peptide Candidates obtained from Biopanning on Brushed 8 hr Pellicle, Screened with 30 min in vivo Pellicle

| ID | Amino Acid Sequences | SEQ ID NO | O.D. at 450 nm (normalized) |
|---|---|---|---|
| Control | No Phage | — | 0.094 |
| DenP3 | TTYHYKNIYQESYQQRNPAV | 121 | 1.000 |
| DenP101 | AIEYQHSATTPWTMRTRLPP | 172 | 0.467 |
| DenP102 | EFYPFAEVPPEKSGIGRQVF | 173 | 0.520 |
| DenP103 | GVHQYSRPTVPSYLWTSGQH | 174 | 0.879 |
| DenP104 | GYQPHYVDHTIGWQPMIRPN | 175 | 0.790 |
| DenP105 | QFNQTSHSFMHGTSGYVPGK | 176 | 0.470 |
| DenP106 | SFSWHRGDWELGHQSKTMGM | 177 | 1.524 |
| DenP107 | SMWHDITKRYRNPSEMVSAY | 178 | 0.726 |

TABLE 19-continued

Phage ELISA Results for Pellicle-binding Peptide Candidates obtained from Biopanning on Brushed 8 hr Pellicle, Screened with 30 min in vivo Pellicle

| ID | Amino Acid Sequences | SEQ ID NO | O.D. at 450 nm (normalized) |
|---|---|---|---|
| DenP108 | THGNKHQSWTYPSEINHKNY | 179 | 1.149 |
| DenP109 | WHEPHQFSGENTDYSSSMGT | 180 | 0.716 |
| DenP111 | DGYKLQTSLDWQMWNP | 182 | 1.051 |
| DenP112 | FPSKWYNHHRHITGHV | 183 | 0.413 |
| DenP113 | GGMGALESYRQWNHLA | 184 | 1.348 |
| DenP114 | GINKGQRPPWESWHEN | 185 | 0.703 |
| DenP115 | GYGQYVSQQTWAHSNK | 186 | 0.501 |
| DenP116 | HDHLSWWGQFDRQNLL | 187 | 1.055 |
| DenP117 | MPGHQESIKVQNWNRV | 188 | 0.433 |
| DenP118 | NLHSPWPSHAAHHWST | 189 | 0.641 |
| DenP119 | NQQMKLVPQHWHRAQP | 190 | 1.051 |

What is claimed is:

1. A peptide-based reagent having the general structure:

$$[[(TBP)_y\text{-}S_q]_m\text{-}[(PBP)_z\text{-}S_r]_n]_p;$$

wherein
   i) TBP is a tooth-binding peptide comprising amino acid SEQ ID NO: 121;
   ii) PBP is a polymer-binding peptide comprising amino acid SEQ ID NO: 118;
   iii) S is a peptide spacer comprising 1 to about 50 amino acids;
   iv) m, n, y and z independently range from 1 to about 10;
   v) p is from 1 to 5; and
   vi) q an r are each independently 0 or 1, provided that both q and r may not be 0.

2. The peptide-based reagent of claim 1 wherein the peptide spacer comprises amino acids selected from the group consisting of proline, lysine, glycine, alanine, serine, threonine, and combinations thereof.

3. A method for whitening teeth comprising:
   (a) providing at least one polymer-coated white colorant;
   (b) providing a composition comprising the peptide-based reagent according to claim 1; and
   (c) contacting a tooth surface with the at least one polymer-coated white colorant of (a) and the composition of (b) whereby said tooth surface is whitened.

4. The method according to claim 3 further comprising the step (d): applying a composition comprising a polymeric sealant; wherein the polymeric sealant is selected from the group consisting of poly(allylamine), acrylates, acrylate copolymers, polyurethanes, carbomers, methicones, amodimethicones, polyethylenene glycol, beeswax, siloxanes, copolymers of methyl vinyl ether and maleic anhydride, linear and cross linked polyvinylpyrrolidone homopolymers, and combinations thereof.

5. An oral care composition comprising the peptide based-reagent of claim 1 and at least one polymer-coated white colorant.

6. A tooth-binding peptide comprising amino acid sequence SEQ ID NO: 121.

7. A peptide-based reagent comprising the tooth-binding peptide of claim 6.

8. An oral care composition comprising the tooth-binding peptide of claim 6 or the peptide-based reagent of claim 7.

9. The oral care composition of claim 8 further comprising at least one polymer coated white colorant.

* * * * *